(12) United States Patent
Harding et al.

(10) Patent No.: US 11,932,670 B2
(45) Date of Patent: Mar. 19, 2024

(54) GLYCOSYLATED COMP PILIN VARIANTS, METHODS OF MAKING AND USES THEREOF

(71) Applicant: VaxNewMo LLC, St. Louis, MO (US)

(72) Inventors: Christian Harding, St. Louis, MO (US); Mario Feldman, St. Louis, MO (US)

(73) Assignee: VaxNewMo LLC, St. Louis, MO (US)

( * ) Notice: Subject to any disclaimer, the term of this patent is extended or adjusted under 35 U.S.C. 154(b) by 0 days.

(21) Appl. No.: 17/251,994

(22) PCT Filed: Jun. 14, 2019

(86) PCT No.: PCT/US2019/037251
§ 371 (c)(1),
(2) Date: Dec. 14, 2020

(87) PCT Pub. No.: WO2019/241672
PCT Pub. Date: Dec. 19, 2019

(65) Prior Publication Data
US 2021/0324017 A1 Oct. 21, 2021

Related U.S. Application Data

(60) Provisional application No. 62/685,970, filed on Jun. 16, 2018, provisional application No. 62/783,971, filed on Dec. 21, 2018.

(51) Int. Cl.
*C07K 14/195* (2006.01)
*A61K 39/00* (2006.01)
*A61K 39/05* (2006.01)
*A61K 39/09* (2006.01)
*A61K 39/108* (2006.01)
*A61P 31/04* (2006.01)

(52) U.S. Cl.
CPC ........ *C07K 14/195* (2013.01); *A61K 39/0266* (2013.01); *A61K 39/05* (2013.01); *A61K 39/092* (2013.01); *A61P 31/04* (2018.01); *A61K 2039/575* (2013.01); *A61K 2039/6037* (2013.01); *C07K 2319/55* (2013.01); *C07K 2319/91* (2013.01)

(58) Field of Classification Search
None
See application file for complete search history.

(56) References Cited

U.S. PATENT DOCUMENTS 9,499,614 B2 11/2016 Hossler et al.
2011/0243980 A1 10/2011 Feldman et al.
2018/0050101 A1 2/2018 Feldman et al.
2018/0194812 A1 7/2018 Simon et al.

FOREIGN PATENT DOCUMENTS

| JP | 2010515430 A | 5/2010 | |
|---|---|---|---|
| WO | 2008093165 A2 | 8/2008 | |
| WO | 2011109600 A1 | 9/2011 | |
| WO | 2013067523 A1 | 5/2013 | |
| WO | 2014057109 A1 | 4/2014 | |
| WO | 2014072405 A1 | 5/2014 | |
| WO | 2016107819 A1 | 7/2016 | |
| WO | WO-2016134485 A1 * | 9/2016 | ............. A61K 39/09 |
| WO | 2019241672 A2 | 12/2019 | |
| WO | 2020131236 A1 | 6/2020 | |

OTHER PUBLICATIONS

Riddle et al., "Safety and Immunogenicity of a Candidate Bioconjugate Vaccine against Shigella flexneri 2a Administered to Healthy Adults: a Single-Blind, Randomized Phase I Study", Clin Vaccine Immunol, Dec. 5, 2016, pp. 908-917, vol. 23, No. 12.
Schaffer et al., "Emerging Facets of Prokaryotic Glycosylation", FEMS Microbiology Review, 2017, pp. 49-91, vol. 41, No. 1.0
Schulz et al., "Identification of Bacterial Protein O-Oligosaccharyltransferases and Their Glycoprotein Substrates", PLoS One, May 3, 2013, p. e62768, vol. 8, No. 5.
Schwarz et al., "A Combined Method of Producing Homogeneous Glycoproteins with Eukaryotic N-glycosylation", Nature Chemical Biology, Apr. 2010, pp. 264-266, vol. 6, No. 4.
Scott et al., "Diversity Within the O-Linked Protein Glycosylation Systems of Acinetobacter Species", Molecular & Cellular Proteomics, 2014, pp. 2354-2370, vol. 13, No. 9.
Search Report and Written Opinion for PCT/CA2016/050208 dated Sep. 1, 2016.
Soininen et al., "IgG Subclass Distribution of Antibodies after Vaccination of Adults with Pneumococcal Conjugate Vaccines", Vaccine, Apr. 9, 1999, pp. 1889-1897, vol. 17, No. 15-16.
Stimson et al., "Meningococcal Pilin: A Glycoprotein Substituted with Digalactosyl 2,4-diacetamido-2,4,6-trideoxyhexose", Mol Microbiol, Sep. 1995, pp. 1201-1214, vol. 17, No. 6.
Supplementary Partial European Search Report for EP16754717 dated Jul. 6, 2018.
Terra et al., "Recent Developments in Bacterial Protein Glycan Coupling Technology and Glycoconjugate Vaccine Design", Journal of Medical Microbiology, Jul. 2012, pp. 919-926, vol. 61, No. 7.
Vaneechoutte et al., "Naturally Transformable *Acinetobacter* sp. Strain ADP1 Belongs to the Newly Described Species *Acinetobacter baylyi*", Applied and Environmental Microbiology, Jan. 2006, pp. 932-936, vol. 72, No. 1.
Vella et al., "Glycoconjugate Vaccines: An Update", Expert Opin Biol Ther, Apr. 2015, pp. 529-546, vol. 15, No. 4.
Vik et al., "Broad Spectrum O-Linked Protein Glycosylation in the Human Pathogen Neisseria gonorrhoeae", Proceedings of the National Academy of Sciences USA, Mar. 2009, pp. 4447-4452, vol. 106, No. 11.

(Continued)

*Primary Examiner* — Brian Gangle
(74) *Attorney, Agent, or Firm* — Thompson Coburn LLP; William A. Holtz

(57) ABSTRACT

Provided herein are glycosylated ComP proteins, fragments and fusion proteins thereof, and methods of making, for example, for use in the production of conjugate vaccines. Also provided herein are conjugate vaccines against diseases including bacterial diseases.

55 Claims, 42 Drawing Sheets
Specification includes a Sequence Listing.

(56) References Cited

OTHER PUBLICATIONS

Wacker et al., "N-linked Glycosylation in Campylobacter Jejuni and its Functional Transfer into *E. coli*", Science, Nov. 29, 2002, pp. 1790-1793, vol. 298, No. 5599.

Wacker et al., "Substrate Specificity of Bacterial Oligosaccharyltransferase Suggests a Common Transfer Mechanism for the Bacterial and Eukaryotic Systems", Proceedings of the National Academy of Sciences USA, 2006, pp. 7088-7093, vol. 103, No. 18.

Wu et al., "Genome Sequencing and Comparative Analysis of Klebsiella pneumoniae NTUH-K2044, a Strain Causing Liver Abscess and Meningitis", Journal of Bacteriology, Jul. 2009, pp. 4452-4501, vol. 191, No. 14.

Wuorimaa et al., "Avidity and Subclasses of IgG after Immunization of Infants with an 11-Valent Pneumococcal Conjugate Vaccine with or without Aluminum Adjuvant", The Journal of Infectious Diseases, 2001, pp. 1211-1215, vol. 184, No. 9.

Yeh et al., "Capsular Serotype K1 or K2, Rather than magA and rmpA, Is a Major Virulence Determinant for Klebsiella pneumoniae Liver Abscess in Singapore and Taiwan", Journal of Clinical Microbiology, Feb. 2007, pp. 466-471, vol. 45, No. 2.

Cerqueira et al., "Hypothetical Protein F951_00736 [Acinetobacter soli CIP 110264]", GenBank: ENV58402.1, Nov. 25, 2019, 2 pages.

Harding et al., "Acinetobacter Strains Carry Two Functional Oligosaccharyltransferases, One Devoted Exclusively to Type IV Pilin, and the Other One Dedicated to O-glycosylation of Multiple Proteins", Molecular Microbiology, 2015, pp. 1023-1041, vol. 96, No. 5.

Porstendoerfer et al., "A Novel Competence Gene, comP, Is Essential for Natural Transformation of *Acinetobacter* sp. Strain BD413", Applied and Environmental Microbiology, Nov. 1997, pp. 4150-4157, vol. 63, No. 11.

Porstendoerfer et al., "Comp [Acinetobacter baylyi]", Oct. 14, 2019, 1 page.

Ravenscroft et al., "Purification and Characterization of a Shigella Conjugate Vaccine, Produced by Glycoengineering *Escherichia coli*", Glycobiology, 2016, pp. 51-62, vol. 26, No. 1.

"Pneumococcal Vaccination", Centers for Disease Control and Prevention—Vaccines and Preventable Diseases, <https://www.cdc.gov/vaccines/vpd/pneumo/index.html>, 2022.

Apweiler et al., "On the Frequency of Protein Glycosylation, as Deduced from Analysis of the SWISS-PROT Database", Biochim Biophys Acta, Dec. 6, 1999, pp. 4-8, vol. 1473, No. 1.

Arakawa et al., "Biosynthesis of Klebsiella K2 Capsular Polysaccharide in *Escherichia coli* HB101 Requires the Functions of rmpA and the Chromosomal cps Gene Cluster of the Virulent Strain Klebsiella pneumoniae Chedid (O1: K2)," Infection and Immunity, Jun. 1991, pp. 2043-2050, vol. 59, No. 6.

Avci et al., "A Novel Mechanism for Glycoconjugate Vaccine Activation of the Adaptive Immune System", Nature Medicine, 2011, pp. 1602-1609, vol. 17, No. 12.

Bentley et al., "Genetic Analysis of the Capsular Biosynthetic Locus from All 90 Pneumococcal Serotypes", PLoS Genetics, Mar. 2006, pp. 0262-0269, vol. 2, No. 3.

Bernatchez et al., "A Single Biofunctional UDP-GlcNAc/Glc 4-epimerase Supports the Synthesis of Three Cell Surface Glycoconjugates in Campylobacter Jejuni", Journal of Biological Chemistry, American Society for Biochemistry and Molecular Biology, Feb. 11, 2005, pp. 4792-4802, vol. 280, No. 6.

Berti et al., "Antimicrobial Glycoconjugate Vaccines: An Overview of Classic and Modern Approaches for Protein Modification", Chemical Society Reviews, 2018, pp. 9015-9025, vol. 47, No. 24.

Carboni et al., "Structure of a Protective Epitope of Group B Streptococcus Type III Capsular Polysaccharide", Proceedings of the National Academy of Sciences USA, May 2017, pp. 5017-5022, vol. 114, No. 19.

Castric, "pilO, a Gene Required for Glycosylation of Pseudomonas aeruginosa 1244 pilin", Microbiology, 1995, pp. 1247-1254, vol. 141, Part 5.

Ciocchini et al., "A Bacterial Engineered Glycoprotein as a Novel Antigen for Diagnosis of Bovine Brucellosis", Vet Microbiol, Aug. 27, 2014, pp. 455-465, vol. 172, No. 3-4.

Comer et al., "Identification of the Pseudomonas aeruginosa 1244 Pilin Glycosylation Site", Infection and Immunity, Jun. 2002, pp. 2837-2845, vol. 70, No. 6.

Comstock et al., "Bacterial Glycans: Key Mediators of Diverse Host Immune Responses", Cell, Sep. 2006, pp. 847-850, vol. 126, No. 5.

De Gregrio et al., "From Empiricism to Rational Design: A Personal Perspective of the Evolution of Vaccine Development", Nature Reviews, Jul. 2014, pp. 505-514, vol. 14, No. 7.

Dykxhoorn et al., "A Set of Compatible Tac Promoter Expression Vectors", Gene, Oct. 24, 1996, pp. 133-136, vol. 177, No. 1-2.

Faridmoayer et al., "Functional Characterization of Bacterial Oligosaccharyltransferases Involved in O-Linked Protein Glycosylation", Journal of Bacteriology, Nov. 2007, pp. 8088-8098, vol. 189, No. 22.

Feldman et al., "A Promising Bioconjugate Vaccine Against Hypervirulent Klebsiella pneumoniae", Proceedings of the National Academy of Sciences USA, Sep. 2019, pp. 18655-18663, vol. 116, No. 37.

Feldman et al., "Engineering N-linked Protein Glycosylation with Diverse O Antigen Lipopolysaccharide Structures in *Escherichia coli*", Proceedings of the National Academy of Sciences USA, Feb. 2005, pp. 3016-3021, vol. 102, No. 8.

Frasch, "Preparation of Bacterial Polysaccharide-Protein Conjugates: Analytical and Manufacturing Challenges", Vaccine, Oct. 30, 2009, pp. 6468-6470, vol. 27, No. 46.

Garcia-Quintanilla et al., "Production of a Recombinant Vaccine Candidate Against Burkholderia Pseudomallei Exploiting the Bacterial N-glycosylation Machinery", Front Microbiol, Jul. 29, 2014, vol. 5, No. 381.

Geno et al., "Pneumococcal Capsules and Their Types: Past, Present, and Future", Clinical Microbiology Reviews, Jul. 2015, pp. 871-899, vol. 28, No. 3.

Giltner et al., "Type IV Pilin Proteins: Versatile Molecular Modules", Microbiology and Molecular Biology Review, Dec. 2012, pp. 740-772, vol. 76, No. 4.

Harding et al, "Acinetobacter Strains Carry Two Functional Oligosaccharyltransferases, One Devoted Exclusively to Type IV Pilin, and the Other One Dedicated to O-glycosylation of Multiple Proteins", Molecular Microbiology, Jun. 2015, pp. 1023-1041, vol. 96, No. 5.

Harding et al., "A Platform for Glycoengineering a Polyvalent Pneumococcal Bioconjugate Vaccine Using *E. coli* as a Host", Nature Communications, 2019, pp. 1-11, vol. 10, No. 891.

Huttner et al., "Safety, Immunogenicity, and Preliminary Clinical Efficacy of a Vaccine Against Extraintestinal Pathogenic *Escherichia coli* in Women with a History of Recurrent Urinary Tract Infection: A Randomised, Single-Blind, Placebo-Controlled Phase 1b Trial", Lancet Infect Dis, May 2017, pp. 528-537, vol. 17, No. 5.

Huttner et al., "The Development and Early Clinical Testing of the ExPEC4V Conjugate Vaccine Against Uropathogenic *Escherichia coli*", Clin Microbiol Infect, Oct. 2018, pp. 1046-1050, vol. 10.

Ihssen et al., "Increased Efficiency of Campylobacter jejuni N-oligosaccharyltransferase PglB by Structure-Guided Engineering", Open Biology, 2015, pp. 1-10, vol. 5.

Iwashkiw et al., "Exploiting the Campylobacter Jejuni Protein Glycosylation System for Glycoengineering Vaccines and Diagnostic Tools Directed Against Brucellosis", Microb Cell Fact, Jan. 25, 2012, vol. 11, No. 13.

Iwashkiw et al., "Identification of a General O-Linked Protein Glycosylation System in Acinetobacter baumannii and Its Role in Virulence and Biofilm Formation", PLoS Pathogens, Jun. 2012, pp. 1-14, vol. 8, No. 6.

Iwashkiw et al., "Identification of General O-Linked Protein Glycosylation System in Acinetobacter Baumannii and Its Role in Virulence and Biofilm Formation", PLOS Pathogens, Jun. 2012, vol. 8, No. 6.

Iwashkiw et al., "Pour Some Sugar on it: The Expanding World of Bacterial Protein O-Linked Glycosylation", Molecular Microbiology, 2013, pp. 14-28, vol. 89, No. 1.

Kay et al., "Recombinant Epression of *Streptococcus pneumoniae* Capsular Polysaccharides in *Escherichia coli*", Open Biol, Apr. 13, 2016, vol. 6, No. 4.

(56) References Cited

OTHER PUBLICATIONS

Kovach et al., "Four New Derivatives of the Broad-Host-Range Cloning Vector pBBR1MCS, Carrying Different Antibiotic-Resistance Cassettes", Gene, Dec. 1, 1995, pp. 175-176, vol. 166, No. 1.
Kowarik et al., "Definition of the Bacterial N-Glycosylation Site Consensus Sequence", The EMBO Journal, 2006, pp. 1957-1966, vol. 25, No. 9.
Lery et al., "Comparative Analysis of Klebsiella pneumoniae Genomes Identifies a Phospholipase D Family Protein as a Novel Virulence Factor", BMC Biology, 2014, pp. 1-15, vol. 12, No. 41.
Malik, "Protein Fusion Tags for Efficient Expression and Purification of Recombinant Proteins in the Periplasmic Space of *E. coli*", 3 Biotech, 2016, pp. 1-7, vol. 6, No. 44.
Nothaft et al., "Protein Glycosylation in Bacteria: Sweeter than Ever", Nature Reviews, Nov. 2010, pp. 765-778, vol. 8, No. 11.
O'Brien et al., "Burden of Disease Caused by *Streptococcus pneumoniae* in Children Younger than 5 Years: Global Estimates", Lancet, Sep. 12, 2009, pp. 893-902, vol. 374, No. 9693.
Pace, "Glycoconjugate Vaccines", Expert Opin Biol Ther, Jan. 2013, pp. 11-33, vol. 13, No. 1.
Pan et al., "Biosynthesis of Conjugate Vaccines Using an O-Linked Glycosylation System", mBio, Mar./Apr. 2016, pp. 1-11, vol. 7, No. 2.
Pan et al., "Genetic Analysis of Capsular Polysaccharide Synthesis Gene Clusters in 79 Capsular Types of *Klebsiella* spp", Scientific Reports, 2015, pp. 1-10, vol. 5, No. 15573.
Pelicic, "Type IV Pili: e pluribus unum?", Molecular Microbiology, 2008, pp. 827-837, vol. 68, No. 4.
Pfizer, "Prevnar 13 Prescribing Information—Package Insert", FDA, Aug. 2017, 43 pages, retrieved from <https://www.fda.gov/downloads/BiologicsBloodVaccines/Vaccines/ApprovedProducts/UCM201669.pdf>.
Pilishvili et al., "Sustained Reductions in Invasive Pneumococcal Disease in the Era of Conjugate Vaccine", The Journal of Infectious Diseases, 2010, pp. 32-41, vol. 201, No. 1.
Pollard et al., "Maintaining Protection Against Invasive Bacteria with Protein-Polysaccharide Conjugate Vaccines", Nat Rev Immunol, Mar. 2009, pp. 213-220, vol. 9, No. 3.
Porstendorfer et al., "ComP, A Pilin-Like Protein Essential for Natural Competence in *Acinetobacter* sp. Strain BD413: Regulation, Modification, and Cellular Localization", Journal of Bacteriology, Jul. 2000, pp. 3673-3680, vol. 182, No. 13.
Power et al., "Genetic Characterization of Pilin Glycosylation and Phase Variation in Neisseria meningitidis", Molecular Microbiology, 2003, pp. 833-847, vol. 49, No. 3.
Price et al., "Glycoengineered Outer Membrane Vesicles: A Novel Platform for Bacterial Vaccines", Sci Rep, Apr. 22, 2016, vol. 6, No. 24931.
Rappuoli et al., "On the Mechanisms of Conjugate Vaccines", Proceedings of the National Academy of Sciences USA, Jan. 2019, pp. 14-16, vol. 116, No. 1.
Schulz et al., "Identification of Bacterial Protein O-Oligosaccharyltransferases and Their Glycoprotein Substrates", PLOS One, May 2013, pp. 1-11, vol. 8, Issue 5.
Ding et al., "Effects of N-Glycosylation Site Removal in Archaellins on the Assembly and Function of Archaella in Methanococcus Maripaludis", PLoS One, Feb. 2015, pp. 1-23, vol. 10 No. 2.
Geourjon et al., "Identification of Related Proteins with Weak Sequence Identity Using Secondary Structure Information", Protein Science, 2001, pp. 788-797, vol. 10.

\* cited by examiner

Figure 1A-C

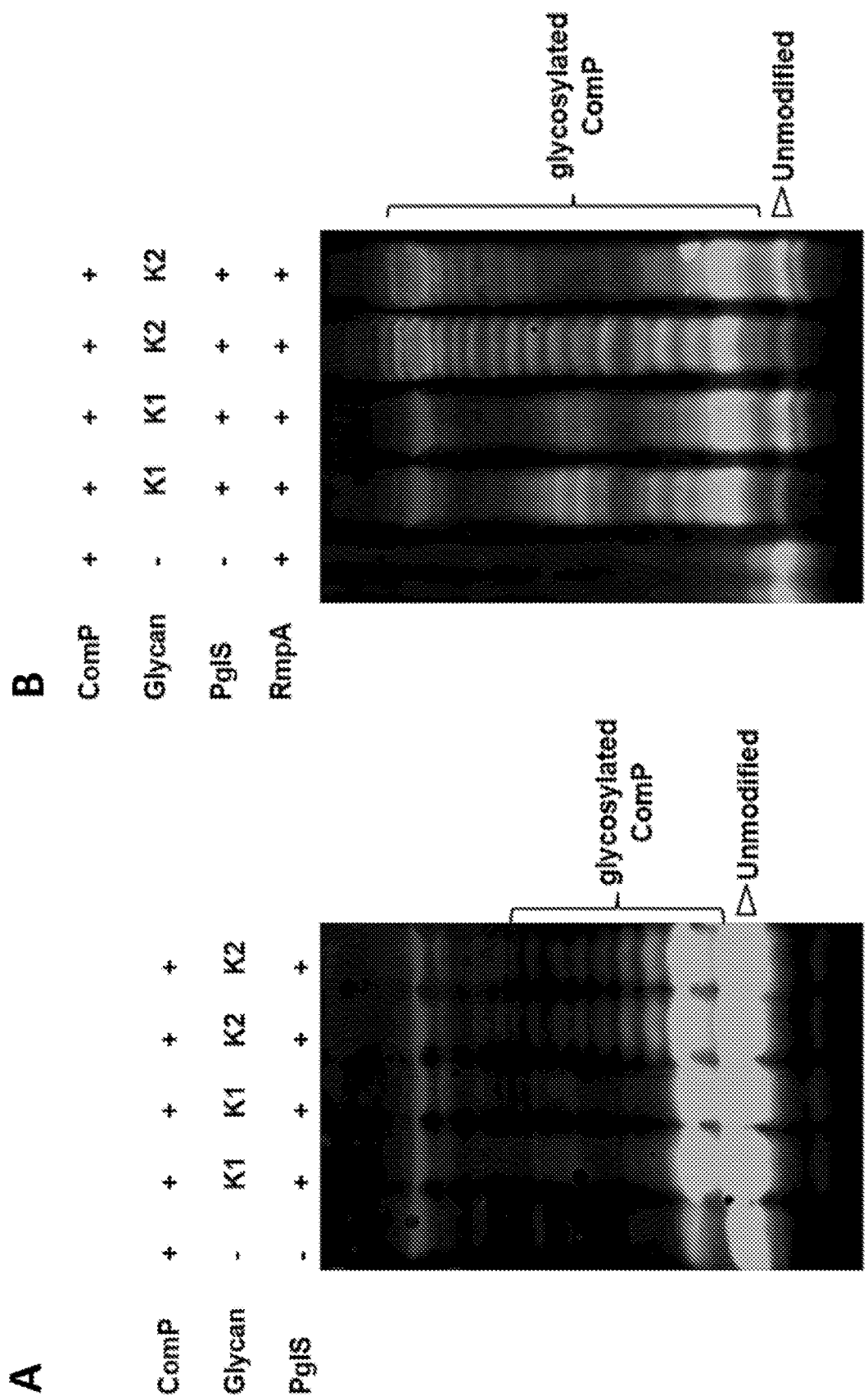
Figure 3A,B

>AAC45886.1 ComP [*Acinetobacter* sp. ADP1]
MNAQKGFTLIELMIVIAIIGILAAIAIPAYTDYTVRAR
VSEGLTAASSMKTTVSENILNAGALVAGTPSTAG
SS<u>CVGVQEISASNATTNVATATC</u>GASSAGQIIVTM
DTTKAKGANITLTPTYASGAVTWKCTTTSDKKYV
PSECRG (SEQ ID NO: 1)

>ENV58402.1 hypothetical protein F951_00736
[*Acinetobacter soli* CIP 110264]
MNAQKGFTLIELMIVIAIIGILAAIAIPAYTDYTVRSR
VTEGLTTASAMKATVSENIMNAGGTSMPSSGN<u>C
TGVTQIASGASAATTNVASAQC</u>SDSDGVITVTMT
DKAKGVSIKLTPSFSSTGSVGWKCTTSSDKKYV
PSECRGT (SEQ ID NO: 2)

>APV36638.1 competence protein [*Acinetobacter
soli* GFJ-2]
MNAQKGFTLIELMIVIAIIGILAAIAIPAYTDYTVRAR
VSEGLTTASAMKATVSENILSAGQIVTGTPSTANS
<u>SCVGVQEINASSSTSNVATATC</u>SGLGVITVTMDS
TKAKGVNLTLTPTYTTSNAVTWKCTTTSDKKYVP
SECRN (SEQ ID NO: 3)

Figure 6

>PKD82822.1 competence protein [*Acinetobacter radioresistens* 50v1]
MNTQKGFTLIELMIVIAIIGILAAIAIPAYTDYTVRAR
VTEAVSTASSMKATVSENIMNAGGTQIPTSGN<u>CV
GVQTIAASNATKNVATATC</u>TDSTGVIVVTTTPAAK
SVPLTLTPTYTGGNVKWACSTTANFKNYVPSEC
RS (SEQ ID NO: 4)

>SNX44537.1 type IV pilus assembly protein PilA [*Acinetobacter puyangensis* ANC 4466]
MNAQKGFTLIELMIVIAIIGILAAIAIPAYTDYTVRAR
VTEALTTASAMKATVSENIMSAGGTTIASSA<u>CNG
VISASATTNVASSAC</u>SGSGVISVTTTAAAKGIVLTL
TPKYTGGNVAWQCTTTSGDAQKYVPSECRTTS
(SEQ ID NO: 5)

>OAL75955.1 competence protein [*Acinetobacter* sp. SFC]
MNTQKGFTLIELMIVIAIIGILAAIAIPAYTDYTVRAK
VTEAISTASAMKATVSENLMSAGGTSIVSTNAN<u>C
AGVETIGASNKTKNVESAAC</u>TAATGVILVTTTAEA
KSVPLTLKPTYGSNVQWKCGTTAAAFKYVPSE
CRNDSSGTGF (SEQ ID NO: 6)

Figure 6 Cont.

>DsbA-GGGS-ComPΔ28$_{110264}$-His
MKKIWLALAGLVLAFSASAAQYEDGKQYTTLEKPVA
GAPQVLEFFSFFCPHCYQFEEVLHISDNVKKKLPEGV
KMTKYHVNFMGGDLGKDLTQAWAVAMALGVEDKVT
VPLFEGVQKTQTIRSASDIRDVFINAGIKGEEYDAAWN
SFVVKSLVAQQEKAAADVQLRGVPAMFVNGKYQLNP
QGMDTSNMDVFVQQYADTVKYLSEKK*GGGS*AYTDY
TVRSRVTEGLTTASAMKATVSENIMNAGGTSMPSSG
NCTGVTQIASGASAATTNVASAQCSDSDGVITVTMTD
KAKGVSIKLTPSFSSTGSVGWKCTTSSDKKYVPSECR
GT<u>HHHHHH</u> (SEQ ID NO: 18)

Legend
DsbA – thiol disulfide oxidoreductase protein (*dsbA* gene)
MBP – maltose binding protein (*malE* gene)
DsbA$_{SP}$ – signal seuqnce of DsbA (first 19 amino acids)
EPA – exotoxin A from *Pseudomonas aeruginosa*
AAA – triple alanine linker
GGGS – glycine-glycine-glycine-serine linker
ComPΔ28$_{110264}$ – ComP from *A. soli* CIP 110264 without the first 28 amino acids
His – hexa-histidine tag

Figure 11

\>MBP-AAA-ComPΔ28₁₁₀₂₆₄-His
MKIKTGARILALSALTTMMFSASALAKIEEGKLVIWING
DKGYNGLAEVGKKFEKDTGIKVTVEHPDKLEEKFPQV
AATGDGPDIIFWAHDRFGGYAQSGLLAEITPDKAFQD
KLYPFTWDAVRYNGKLIAYPIAVEALSLIYNKDLLPNPP
KTWEEIPALDKELKAKGKSALMFNLQEPYFTWPLIAA
DGGYAFKYENGKYDIKDVGVDNAGAKAGLTFLVDLIK
NKHMNADTDYSIAEAAFNKGETAMTINGPWAWSNIDT
SKVNYGVTVLPTFKGQPSKPFVGVLSAGINAASPNKE
LAKEFLENYLLTDEGLEAVNKDKPLGAVALKSYEEEL
AKDPRIAATMENAQKGEIMPNIPQMSAFWYAVRTAVIN
AASGRQTVDEALKDAQTN*AAA*AYTDYTVRSRVTEGL
TTASAMKATVSENIMNAGGTSMPSSGNCTGVTQIASG
ASAATTNVASAQCSDSDGVITVTMTDKAKGVSIKLTPS
FSSTGSVGWKCTTSSDKKYVPSECRGT<u>HHHHHH</u>
(SEQ ID NO: 19)

Figure 11 Cont.

>DsbA_SP-EPA-GGGS-ComPΔ28_110264-His
MKKIWLALAGLVLAFSASAAEEAFDLWNECAKACVL
DLKDGVRSSRMSVDPAIADTNGQGVLHYSMVLEGGN
DALKLAIDNALSITSDGLTIRLEGGVEPNKPVRYSYTR
QARGSWSLNWLVPIGHEKPSNIKVFIHELNAGNQLSH
MSPIYTIEMGDELLAKLARDATFFVRAHESNEMQPTL
AISHAGVSVVMAQAQPRREKRWSEWASGKVLCLLD
PLDGVYNYLAQQRCNLDDTWEGKIYRVLAGNPAKHD
LDIKPTVISHRLHFPEGGSLAALTAHQACHLPLETFTR
HRQPRGWEQLEQCGYPVQRLVALYLAARLSWNQVD
QVIRNALASPGSGGDLGEAIREQPEQARLALTLAAAE
SERFVRQGTGNDEAGAASADVVSLTCPVAAGECAGP
ADSGDALLERNYPTGAEFLGDGGDISFSTRGTQNWT
VERLLQAHRQLEERGYVFVGYHGTFLEAAQSIVFGGV
RARSQDLDAIWRGFYIAGDPALAYGYAQDQEPDARG
RIRNGALLRVYVPRSSLPGFYRTGLTLAAPEAAGEVE
RLIGHPLPLRLDAITGPEEEGGRLTILGWPLAERTVVIP
SAIPTDPRNVGGDLDPSSIPDKEQAISALPDYASQPGK
PPREDLK*GGGS*AYTDYTVRSRVTEGLTTASAMKATVS
ENIMNAGGTSMPSSGNCTGVTQIASGASAATTNVASA
QCSDSDGVITVTMTDKAKGVSIKLTPSFSSTGSVGWK
CTTSSDKKYVPSECRGT*HHHHHH* (SEQ ID NO: 20)

Figure 11 Cont.

\>AAC45886.1 ComPΔ28 [*Acinetobacter* sp. ADP1]
AYTDYTVRARVSEGLTAASSMKTTVSENILNAGA
LVAGTPSTAGSSCVGVQEISASNATTNVATATCG
ASSAGQIIVTMDTTKAKGANITLTPTYASGAVTWK
CTTTSDKKYVPSECRG (SEQ ID NO: 7)

\>ENV58402.1 hypothetical protein F951_00736
Δ28 [*Acinetobacter soli* CIP 110264]
AYTDYTVRSRVTEGLTTASAMKATVSENIMNAGG
TSMPSSGNCTGVTQIASGASAATTNVASAQCSD
SDGVITVTMDKAKGVSIKLTPSFSSTGSVGWKC
TTSSDKKYVPSECRGT (SEQ ID NO: 8)

\>APV36638.1 competence protein Δ28
[*Acinetobacter soli* GFJ-2]
AYTDYTVRARVSEGLTTASAMKATVSENILSAGQI
VTGTPSTANSSCVGVQEINASSSTSNVATATCSG
LGVITVTMDSTKAKGVNLTLTPTYTTSNAVTWKC
TTTSDKKYVPSECRN (SEQ ID NO: 9)

Figure 14

\>PKD82822.1 competence protein Δ28
[*Acinetobacter radioresistens* 50v1]
AYTDYTVRARVTEAVSTASSMKATVSENIMNAGG
TQIPTSGN<u>CVGVQTIAASNATKNVATATC</u>DSTG
VIVVTTTPAAKSVPLTLTPTYTGGNVKWACSTTA
NFKNYVPSECRS (SEQ ID NO: 10)

\>SNX44537.1 type IV pilus assembly protein PilA
Δ28 [*Acinetobacter puyangensis* ANC 4466]
AYTDYTVRARVTEALTTASAMKATVSENIMSAGG
TTIASSA<u>CNGVISASATTNVASSAC</u>SGSGVISVTT
TAAAKGIVLTLTPKYTGGNVAWQCTTTSGDAQKY
VPSECRTTS (SEQ ID NO: 11)

\>OAL75955.1 competence protein Δ28
[*Acinetobacter* sp. SFC]
AYTDYTVRAKVTEAISTASAMKATVSENLMSAGG
TSIVSTNAN<u>CAGVETIGASNKTKNVESAAC</u>TAAT
GVILVTTTAEAKSVPLTLKPTYTGSNVQWKCGTT
AAAFKYVPSECRNDSSGTGF (SEQ ID NO: 12)

Figure 14 Cont.

| | | |
|---|---|---|
| ADP1 | CVGVQEIS--AS NATTNVATATC | (SEQ ID NO: 13) |
| 110264 | CTGVTQIASGAS AATTNVASAQC | (SEQ IS NO: 14) |
| GFJ_2 | CVGVQEIN--AS SSTSNVATATC | (SEQ ID NO: 15) |
| SFC | CAGVETIG--AS NKTKNVESAAC | (SEQ ID NO: 16) |
| P50v1 | CVGVQTIA--AS NATKNVATATC | (SEQ ID NO: 17) |

Figure 15

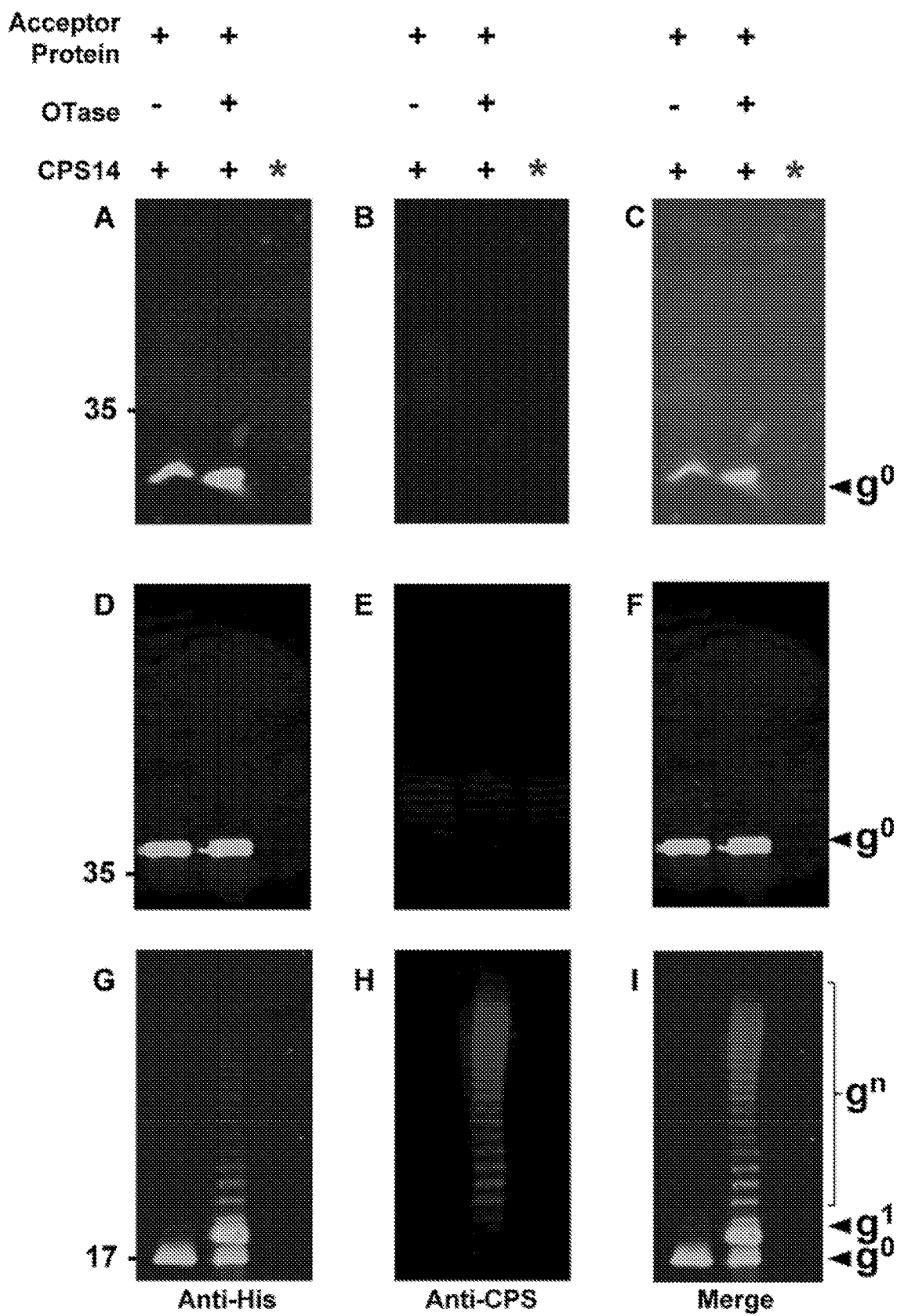
Figure 19A-I

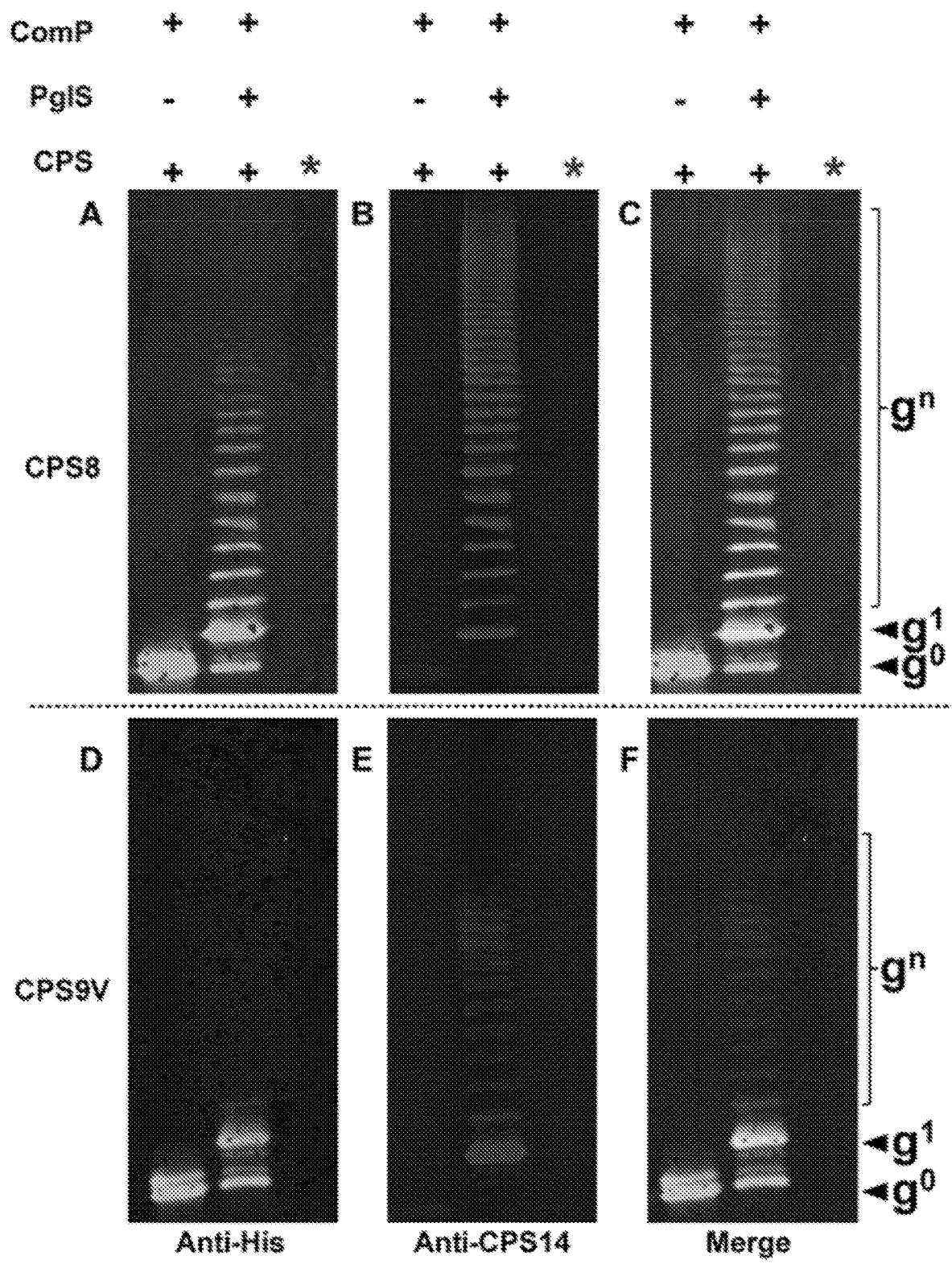
Figure 21A-F

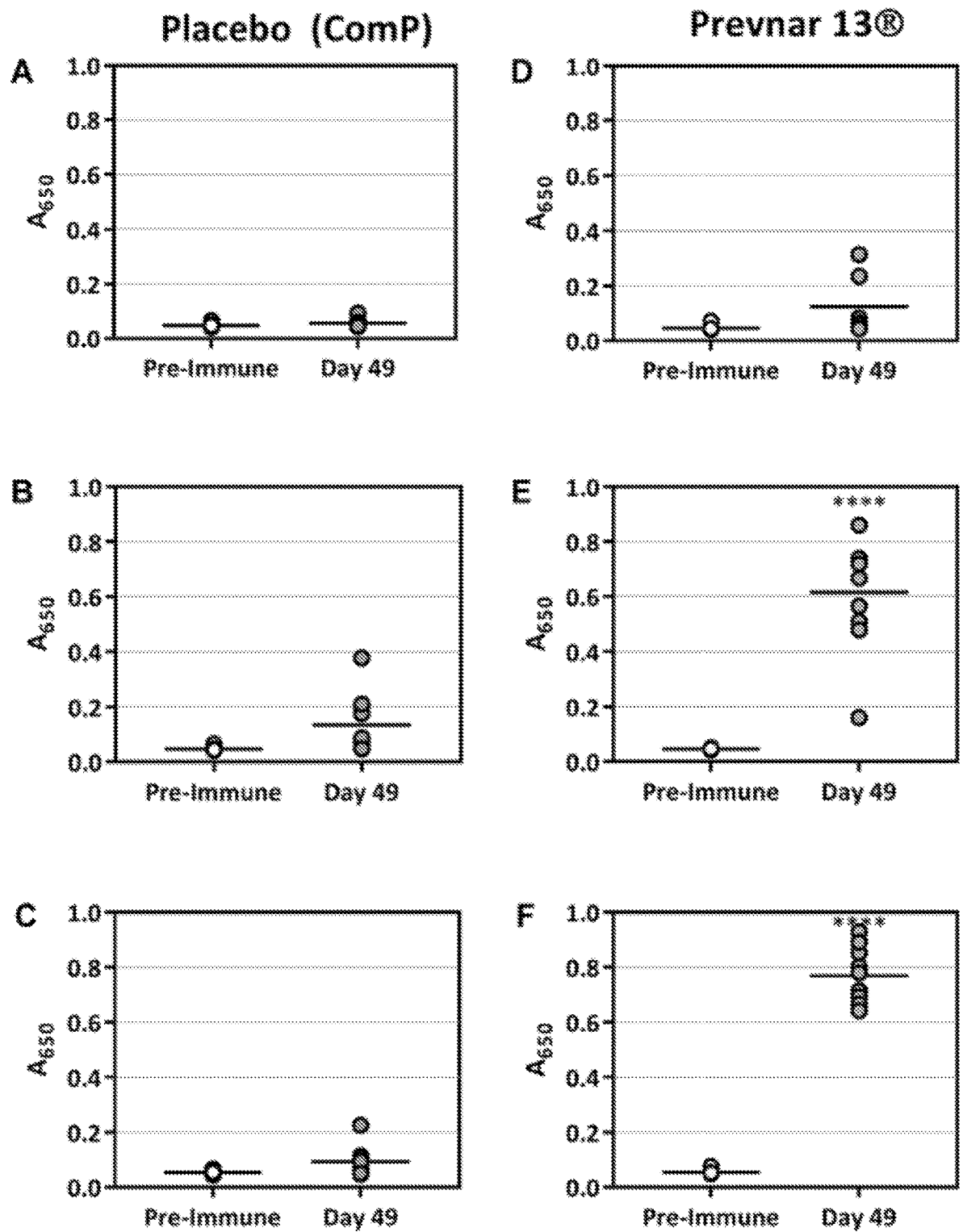
Figure 22A-F

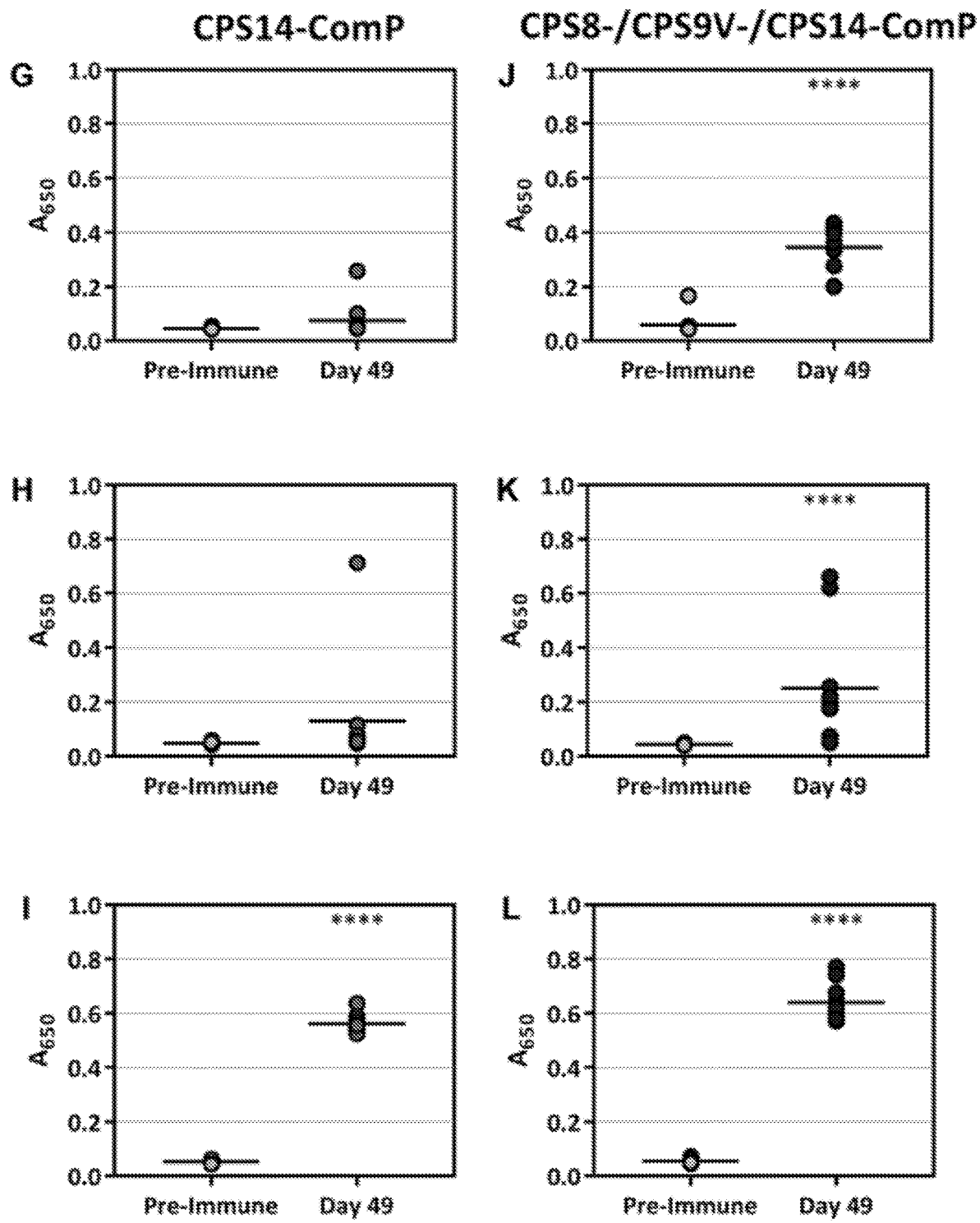
Figure 22G-L

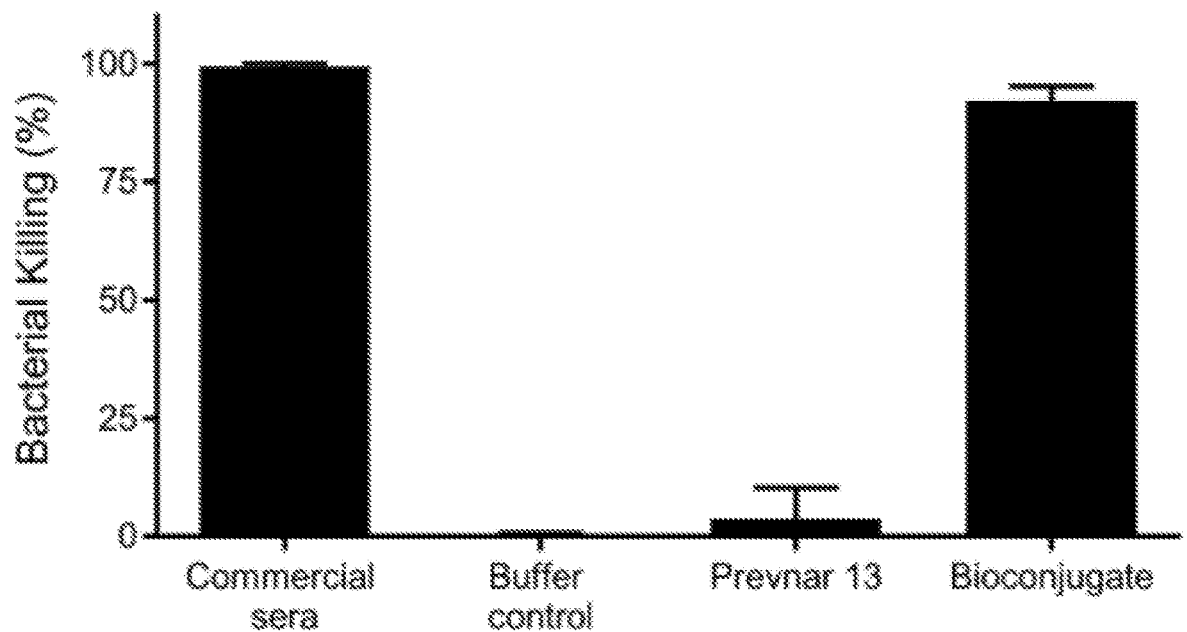
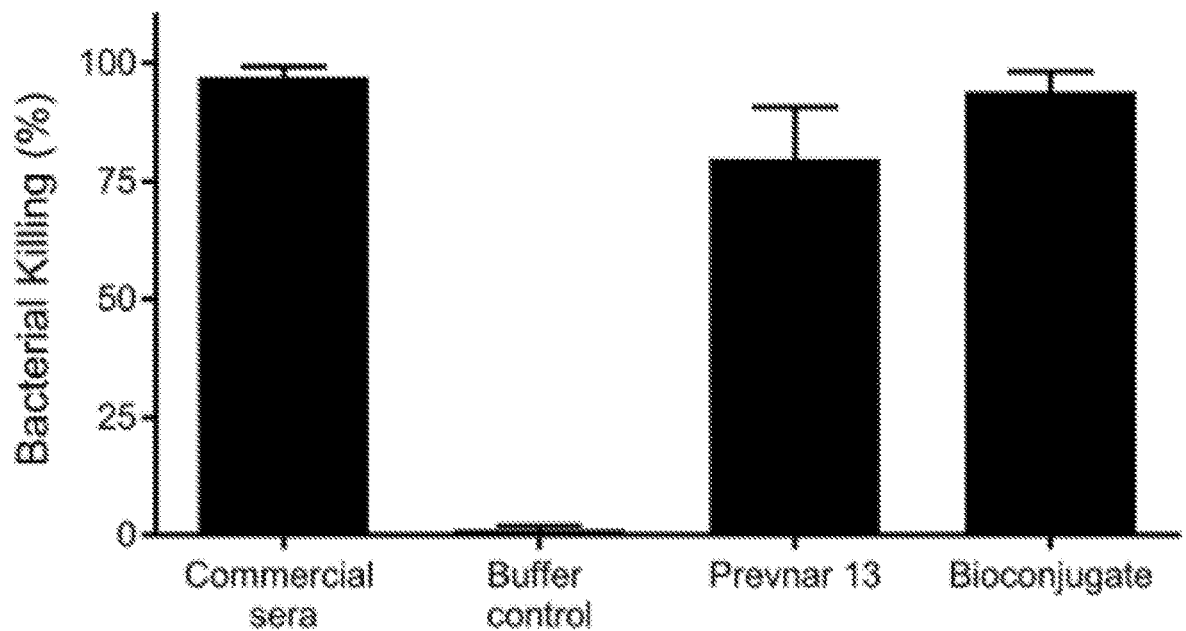
Figure 23A,B

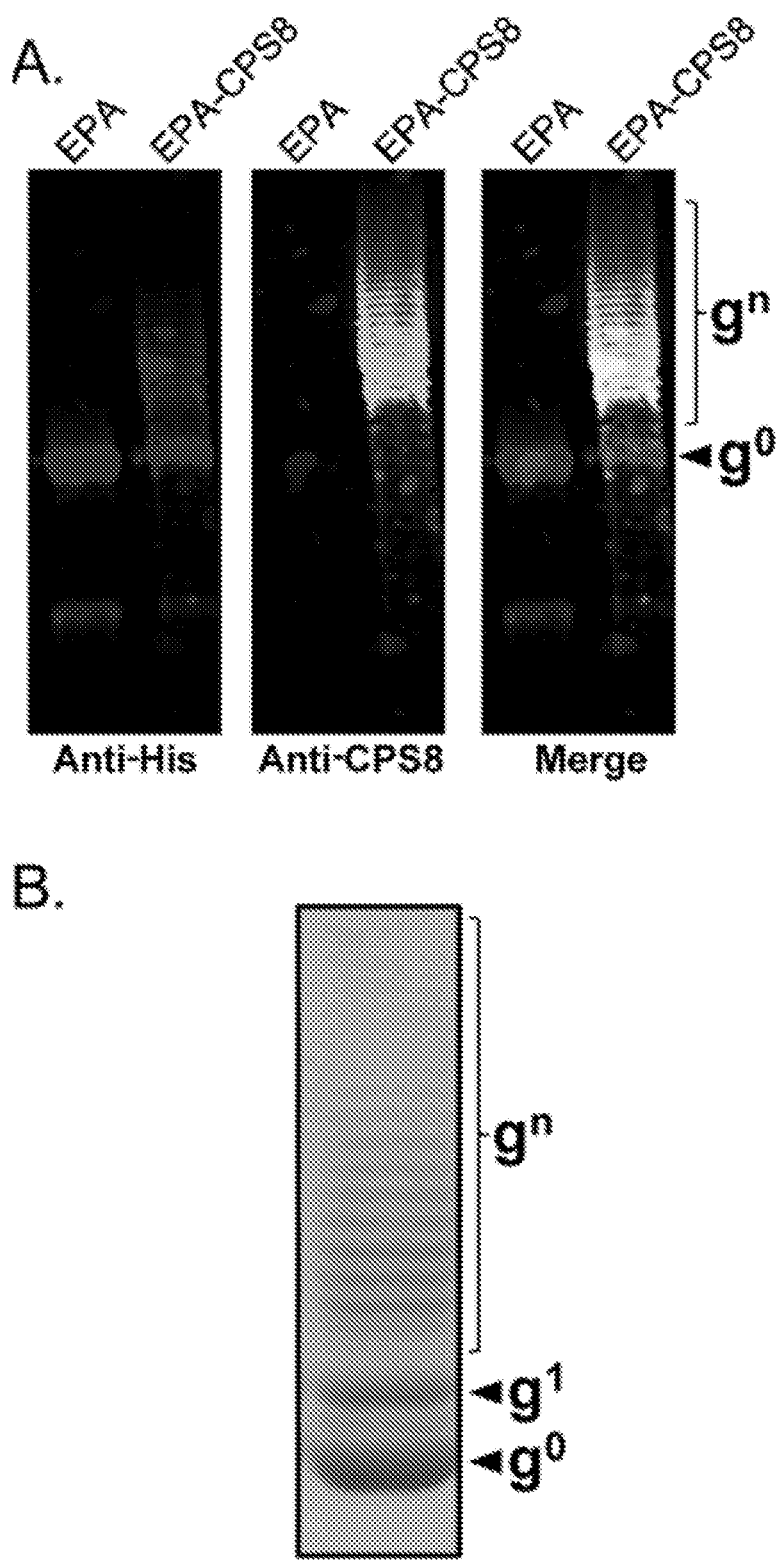
Figure 24A,B

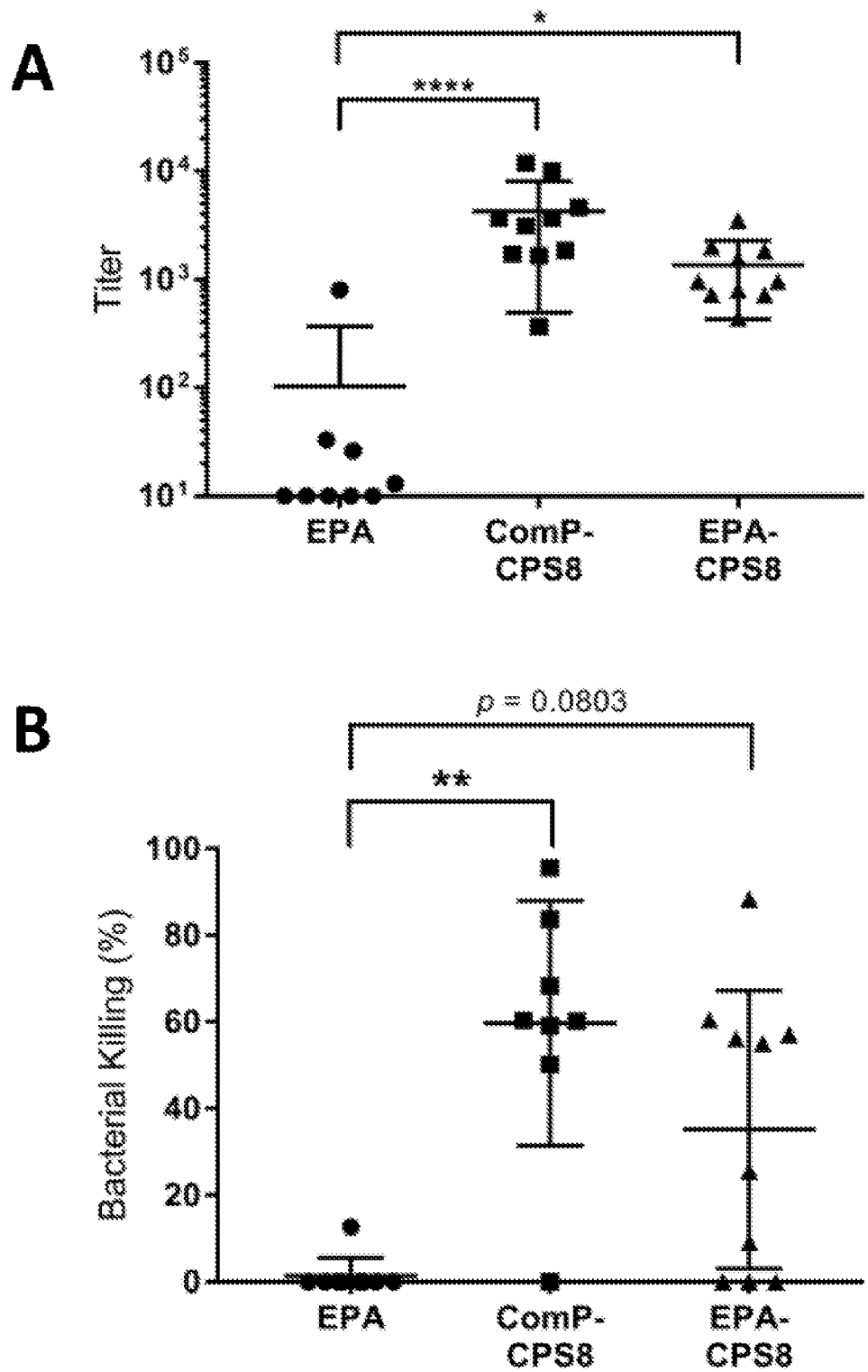
Figure 25A,B

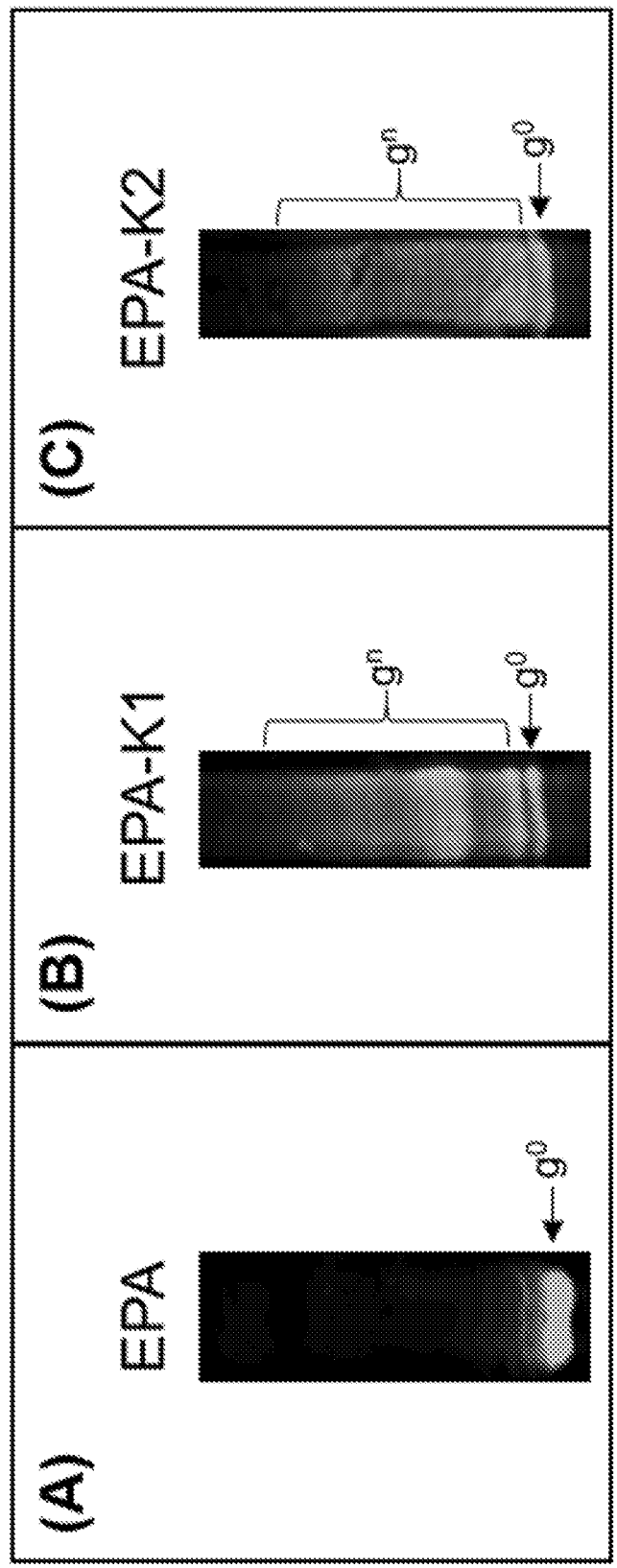
Figure 27A,B,C

GLYCOSYLATED COMP PILIN VARIANTS, METHODS OF MAKING AND USES THEREOF

CROSS-REFERENCE TO RELATED APPLICATIONS

This application is a 35 U.S.C. § 371 National Phase application of International Patent Application No. PCT/US2019/037251, filed Jun. 14, 2019, which claims the benefit of U.S. Provisional Application 62/685,970, filed on Jun. 16, 2018 and U.S. Provisional Application 62/783,971, filed on Dec. 21, 2018, all of which are incorporated herein in their entireties.

This application is related to U.S. application Ser. No. 15/553,733, filed Aug. 25, 2017, which is a U.S. national stage application of PCT/CA2016/050208, filed Feb. 26, 2016, which claims the benefit of U.S. Provisional Appl. No. 62/121,439, filed on Feb. 26, 2015.

GOVERNMENT FUNDING STATEMENT

This invention was made with government support under the R41 AI131742, and R41 AI142928 awarded by the National Institutes of Health. The Government has certain rights in the invention.

BACKGROUND

*Streptococcus pneumoniae* (*S. pneumoniae*) is a leading cause of pneumonia globally, particularly, afflicting children five years of age or younger (O'Brien, K. L. et al. *Lancet* 374, 893-902 (2009)). Estimates indicate that ~1.5 million people die each year as a result of *S. pneumoniae* infection, almost one million of those deaths are among children (Pneumococcal conjugate vaccine for childhood immunization—WHO position paper. *Wkly Epidemiol Rec* 82, 93-104 (2007)). The recommended prophylactic treatments comprise multiple commercially licensed vaccines (Prevention, C.f.D.C.a. Pneumococcal Vaccination, on the world wide web at cdc.gov/vaccines/vpd/pneumo/index.html). PNEUMOVAX 23®, a 23-valent polysaccharide vaccine, is used in elderly populations as polysaccharide vaccines usually act as T cell independent antigens, do not elicit high avidity IgG responses or B cell memory, and are not effective in children (Pace, D. *Expert Opin Biol Ther* 13, 11-33 (2013); Vella, M. & Pace, D. *Expert Opin Biol Ther* 15, 529-546 (2015)). On the other hand, pneumococcal conjugate vaccines, comprised of pneumococcal capsular polysaccharide covalently attached to a carrier protein, have been shown to be effective and generate immunological memory across all age groups due to their ability to act as T-cell dependent antigens (Pollard, A. J., Perrett, K. P. & Beverley, P. C. *Nat Rev Immunol* 9, 213-220 (2009); Avci, F. Y., Li, X., Tsuji, M. & Kasper, D. L. *Nat Med* 17, 1602-1609 (2011)).

Three pneumococcal conjugate vaccines have been commercially licensed since the year 2000: PREVNAR®; SYNFLORIX; and PREVNAR 13®, the most broadly protecting pneumococcal conjugate vaccine, is comprised of 13 protein-polysaccharide conjugates consisting of pneumococcal serotypes 1, 3, 4, 5, 6A, 6B, 7F, 9V, 14, 18C, 19A, 19F, and 23F, each individually linked to the genetically inactivated diphtheria toxoid $CRM_{197}$ (Package Insert—PREVNAR 13®—FDA, on the world wide web at fda.gov/downloads/BiologicsBloodVaccinesNaccines/ApprovedProducts/UCM201669.pdf). Although highly protective in a three dose primary schedule, Prevnar 13 is one of the most expensive vaccines produced due to its complex manufacturing process resulting in a price tag of ~$600 US dollars for primary and booster immunizations (Prevention, C.f.D.C.a. Vaccines for Children Program (VFC), on the world wide web at cdc.gov/vaccines/programs/vfc/awardees/vaccine-management/price-list/index.html> (2018)). In fact, PREVNAR 13® has been Pfizer's leading revenue generating product from 2015-2017 with total revenues exceeding 17.5 billion U.S. dollars (Pfizer Inc. 2017 Financial Report, on the world wide web at sec.gov/Archives/edgar/data/78003/000007800318000027/pfe-exhibit13x12312017x10k.htm (2018)). Although pneumococcal conjugate vaccines, namely PREVNAR 13® and SYNFLORIX, have significantly reduced the burden of invasive pneumococcal disease, variations in global serotype distributions as well as serotype replacement and displacement events necessitate the introduction of a broader PCV providing additional protection to vulnerable patient populations.

Currently licensed pneumococcal conjugate vaccines are synthesized chemically, which is a tedious process plagued with technical challenges, low yields, and batch-to-batch variations; highlighting the need for improved conjugate vaccine synthetic methodologies (Frasch, C. E. *Vaccine* 27, 6468-6470 (2009)). Over the last 15 years, in vivo conjugation using bacterial protein glycosylation systems has emerged as a feasible alternative to chemical conjugations, with multiple bioconjugate vaccine candidates now in various stages of development and clinical trials (Huttner, A. & Gambillara, V. *Clin Microbiol Infect* (2018); Huttner, A. et al. *Lancet Infect Dis* 17, 528-537 (2017); Riddle, M. S. et al. *Clin Vaccine Immunol* 23, 908-917 (2016)). Protein glycosylation is a ubiquitous post-translational modification in which carbohydrates, also known as sugars or glycans, are covalently linked to proteins (aka polypeptides) (Apweiler, R., Hermjakob, H. & Sharon, N. *Biochim Biophys Acta* 1473, 4-8 (1999)). In bacteria, glycans are commonly bound to proteins via N- or O-linkages on asparagine and serine/threonine residues respectively (Nothaft, H. & Szymanski, C. M. *Nat Rev Microbiol* 8, 765-778 (2010)). Several pathways for bacterial glycosylation have been characterized, and one of the best described is the oligosaccharyltransferase (OTase)-dependent glycosylation pathway in Gram negative bacteria (Iwashkiw, J. A., Vozza, N. F., Kinsella, R. L. & Feldman, M. F. *Mol Microbiol* 89 (2013)). In this system, generally a lipid-linked oligosaccharide is assembled sequentially at the cytoplasmic leaflet of the inner membrane, flipped to the periplasmic leaflet, and then transferred to acceptor proteins by either N- or O-OTases depending on the site of glycan attachment generating a variety of glycoproteins (Iwashkiw, J. A., Vozza, N. F., Kinsella, R. L. & Feldman, M. F. *Mol Microbiol* 89, 14-28 (2013)).

Glycoproteins have been recombinantly synthesized in *Escherichia coli* (*E. coli*) for use as vaccines and/or diagnostics by co-expressing three components: (1) a genetic cluster encoding for the proteins required to synthesize a glycan of interest; (2) an OTase; and (3) an acceptor protein (Ciocchini, A. E. et al. *Vet Microbiol* 172, 455-465 (2014); Garcia-Quintanilla, F., Iwashkiw, J. A., Price, N. L., Stratilo, C. & Feldman, M. F. *Front Microbiol* 5, 381 (2014); Iwashkiw, J. A. et al. *Microb Cell Fact* 11, 13 (2012)). One drawback of this process is the apparent substrate specificity of the known OTases, which has been suggested to be regulated by the reducing end sugar (Wacker, M. et al. *Proc Natl Acad Sci USA* 103, 7088-7093 (2006)) (i.e., the first monosaccharide in the growing polysaccharide chain). Although OTases are able to transfer many different oligoand polysaccharide structures, some sugars are not efficiently conjugated by the known OTases to acceptor proteins. Therefore, characterizing novel OTases is paramount for developing the next generation of conjugate vaccines.

OTases currently used for commercially synthesizing glycoconjugates are the *Campylobacter jejuni* N-OTase PglB and the *Neisseria meningitidis* O-OTase PglL, both of which exhibit a great deal of promiscuity towards glycan substrates (Feldman, M. F. et al. *Proc Natl Acad Sci USA* 102, 3016-3021 (2005); Faridmoayer, A., Fentabil, M. A., Mills, D. C., Klassen, J. S. & Feldman, M. F. *J Bacteriol* 189, 8088-8098 (2007)). However, neither enzyme has been experimentally demonstrated to conjugate *Streptococcus pneumoniae* capsular polysaccharides (CPSs) containing glucose as the reducing end sugar to proteins (Geno, K. A. et al. *Clin Microbiol Rev* 28, 871-899 (2015)), to proteins. More than 90 CPS serotypes have been characterized for pneumococcus, each possessing a structurally distinct capsular polysaccharide structure; however, more than 70% of *S. pneumoniae* CPSs contain glucose as the reducing end sugar (Geno, K. A. et al. *Clin Microbiol Rev* 28, 871-899 (2015)). Therefore, to complement and/or replace existing manufacturing pipelines in order to more rapidly generate the next generation of pneumococcal conjugate vaccine, novel methods of pneumococcal vaccine synthesis are needed.

SUMMARY

Provide for herein is a bioconjugate, for example certain aspects and features of which are described in this paragraph, comprising an oligo- or polysaccharide covalently linked to a fusion protein, wherein the fusion protein comprises a ComP protein (ComP) or a glycosylation tag fragment thereof. In certain aspects, the fusion protein is glycosylated with the oligo- or polysaccharide on the ComP protein or glycosylation tag fragment thereof at a serine residue corresponding to the conserved serine residue at position 84 of SEQ ID NO: 1 ($ComP_{ADP1}$: AAC45886.1). In certain aspects, the ComP protein comprises an amino acid sequence that is at least 50%, 60%, 70%, 75%, 80%, 85%, 90%, 95%, 96%, 97%, 98%, 99%, or 100% identical to SEQ ID NO: 7 ($ComP\Delta28_{ADP1}$), and contains a serine residue corresponding to the conserved serine residue at position 84 of SEQ ID NO: 1 ($ComP_{ADP1}$: AAC45886.1). In certain aspects, the ComP protein comprises SEQ ID NO: 7 ($ComP\Delta28_{ADP1}$), SEQ ID NO: 8 ($ComP\Delta28_{110264}$), SEQ ID NO: 9 ($ComP\Delta28_{GFJ-2}$), SEQ ID NO: 10 ($ComP\Delta28_{P50v1}$), SEQ ID NO: 11 ($ComP\Delta28_{4466}$), or SEQ ID NO: 12 ($ComP\Delta28_{SFC}$). In certain aspects, the ComP protein comprises an amino acid sequence that is at least 50%, 60%, 70%, 75%, 80%, 85%, 90%, 95%, 96%, 97%, 98%, 99%, or 100% identical to SEQ ID NO: 1 ($ComP_{ADP1}$: AAC45886.1), and contains a serine residue corresponding to the conserved serine residue at position 84 of SEQ ID NO: 1 ($ComP_{ADP1}$: AAC45886.1). In certain aspects, the ComP protein comprises SEQ ID NO: 1 ($ComP_{ADP1}$: AAC45886.1), SEQ ID NO: 2 ($ComP_{110264}$: ENV58402.1), SEQ ID NO: 3 ($ComP_{GFJ-2}$: APV36638.1), SEQ ID NO: 4 ($Com_{P50v1}$: PKD82822.1), SEQ ID NO: 5 ($ComP_{4466}$: SNX44537.1), or SEQ ID NO: 6 ($ComP_{SFC}$: OAL75955.1). In certain aspects, the glycosylation tag fragment of the ComP protein is a ComPΔ28 polypeptide lacking amino acid residues corresponding to amino acid residues 1 to 28 of SEQ ID NO: 1 ($ComP_{ADP1}$: AAC45886.1). In certain aspects, the ComPΔ28 polypeptide is selected from the group consisting of SEQ ID NO: 7, SEQ ID NO: 8, SEQ ID NO: 9, SEQ ID NO: 10, SEQ ID NO: 11, and SEQ ID NO: 12. In certain aspects, the glycosylation tag fragment of the ComP protein comprises a region corresponding to the region of SEQ ID NO: 2 ($ComP_{110264}$: ENV58402.1) comprising the serine residue at position 82 of SEQ ID NO: 2 ($ComP_{110264}$: ENV58402.1) flanked by a disulfide bond connecting the alpha beta loop to the beta strand region. In certain aspects, the glycosylation tag fragment of the ComP protein comprises an amino acid sequence that is at least 70%, 75%, 80%, 85%, 90%, 95%, 96%, 97%, 98%, 99%, or 100% identical to an amino acid selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and NGVISASATTNVASSA (SEQ ID NO: 44), wherein said glycosylation tag fragment comprises the serine residue corresponding to the conserved serine residue at position 84 of SEQ ID NO: 1 ($ComP_{ADP1}$: AAC45886.1). In certain aspects, the glycosylation tag fragment of the ComP protein comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and NGVISASATTNVASSA (SEQ ID NO: 44), or a variant thereof having one, two, three, four, five, six, or seven amino acid substitutions, additions, and/or deletions, wherein the variant maintains the serine residue corresponding to the conserved serine residue at position 84 of SEQ ID NO: 1 (ComPADP1: AAC45886.1). In certain aspects, the glycosylation tag fragment of the ComP protein comprises the amino acid consensus sequence of SEQ ID NO: 37, or a fragment of at least 5, 10, 15, 20, 30, 35, or 40 consecutive amino acids thereof, wherein said glycosylation tag fragment comprises the serine residue corresponding to the conserved serine residue at position 84 of SEQ ID NO: 1 ($ComP_{ADP1}$: AAC45886.1), or a variant thereof having one, two, three, four, five, six, or seven amino acid substitutions, additions, and/or deletions, wherein the variant maintains the serine residue corresponding to the conserved serine residue at position 84 of SEQ ID NO: 1 (ComPADP1: AAC45886.1). In certain aspects, the glycosylation tag fragment of the ComP protein comprises the amino acid consensus sequence of SEQ ID NO: 38 or 45, or a fragment of at least 5, 6, 7, 8, 9, 10, 11, 12, 13, 14, 15, 16, 17, 18, 19, or 20 consecutive amino acids thereof, wherein said glycosylation tag fragment comprises the serine residue corresponding to the conserved serine residue at position 84 of SEQ ID NO: 1 ($ComP_{ADP1}$: AAC45886.1), or a variant thereof having one, two, three, four, five, six, or seven amino acid substitutions, additions, and/or deletions, wherein the variant maintains the serine residue corresponding to the conserved serine residue at position 84 of SEQ ID NO: 1 (ComPADP1: AAC45886.1). In certain aspects, the oligo- or polysaccharide is produced by a bacteria from the genus *Streptococcus*. In certain aspects, the polysaccharide is a *S. pneumoniae, S. agalactiae,* or *S. suis* capsular polysaccharide. In certain aspects, the capsular polysaccharide is CPS14, CPS8, CPS9V, or CPS15b. In certain aspects, the capsular polysaccharide is CPS8. In certain aspects, the oligo- or polysaccharide is produced by a bacteria from the genus *Klebsiella*. In certain aspects, the oligo- or polysaccharide is a *Klebsiella pneumoniae, Klebsiella varricola, Klebsiella michinganenis,* or *Klebsiella oxytoca* capsular polysaccharide. In certain aspects, the polysaccharide is a *Klebsiella pneumoniae* capsular polysaccharide. In certain aspects, the polysaccharide is a serotype K1 or serotype K2 capsular polysaccharide of *Klebsiella pneumoniae*. In certain aspects, the oligo- or polysaccharide comprises a glucose at its reducing end. In certain aspects, the bioconjugate is produced in vivo. In certain aspects, the bioconjugate is produced in a bacterial cell. In certain aspects, the fusion protein comprises a carrier protein selected from the group consisting of diphtheria toxoid CRM197, tetanus toxoid, *Pseudomonas aeruginosa* Exotoxin A (EPA), tetanus toxin C fragment, cholera toxin B subunit, and *Haemophilus influenza* protein D, or a fragment thereof. In certain aspects, the ComP protein or glycosylation tag fragment thereof is located at the N-terminal end of the fusion protein, at the C-terminal end of the fusion protein, and/or internally within the fusion protein In certain aspects, the carrier protein or fragment thereof is linked to the ComP protein or glycosylation tag fragment thereof via an amino acid linker. In certain aspects, the fusion protein comprises two or more, three or more, four or more, five or more, six or more, eight or more, ten or more, fifteen or more, or twenty or more glycosylation tag fragments of a ComP protein. In certain aspects, the fusion protein comprises any of 2, 3, 4, 5, 6, 7, 8, 9, 10, 11, 12, 13, 14, 15, or 20 to any of 3, 4, 5, 6, 7, 8, 9, 10, 11, 12, 13, 14, 15, 20, or 25 glycosylation tag fragments of a ComP protein. In certain aspects, the bioconjugate is a conjugate vaccine. In certain aspects, the conjugate vaccine is a vaccine against *Streptococcus pneumoniae* serotype 8. In certain aspects, the conjugate vaccine is administered to a subject, it induces an immune response. In certain aspects, the immune response elicits long term memory (memory B and T cells), is an antibody response. In certain aspects, the antibody response is a serotype-specific antibody response. In certain aspects, the antibody response is an IgG or IgM response. In certain aspects, the antibody response is an IgG response. In certain aspects, the IgG response is an IgG1 response. In certain aspects, the conjugate vaccine generates immunological memory in a subject administered the vaccine.

Provided herein is a ComP glycosylation tag, for example certain aspects and features of which are described in this paragraph, comprising an isolated fragment of a ComP protein, wherein the fragment comprises a serine residue corresponding to the conserved serine residue at position 84 in SEQ ID NO: 1 (ComP$_{ADP1}$: AAC45886.1). In certain aspects, the fragment comprises at least 5, 6, 7, 8, 9, 10, 11, 12, 13, 14, 15, 16, 17, 18, 19, 20, 21, 22, 23, 24, 25, 26, 27, 28, 29, 30, 35, or 40 amino acids of the ComP protein. In certain aspects, the ComP protein is a ComP protein as described above. In certain aspects, the glycosylation tag is attached to a heterologous carrier protein. In certain aspects, the heterologous carrier protein is selected from the group consisting of diphtheria toxoid CRM197, tetanus toxoid, *Pseudomonas aeruginosa* Exotoxin A (EPA), tetanus toxin C fragment, cholera toxin B subunit, and *Haemophilus influenza* protein D, or a fragment thereof. In certain aspects, the glycosylation tag is a ComPΔ28 polypeptide lacking amino acid residues corresponding to amino acid residues 1 to 28 of SEQ ID NO: 1 (ComP$_{ADP1}$: AAC45886.1). In certain aspects, the ComPΔ28 polypeptide is selected from the group consisting of SEQ ID NO: 7 (ComPΔ28$_{ADP1}$), SEQ ID NO: 8 (ComPΔ28$_{110264}$), SEQ ID NO: 9 (ComPΔ28$_{GFJ-2}$), SEQ ID NO: 10 (ComPΔ28$_{P50v1}$), SEQ ID NO: 11 (ComPΔ28$_{4466}$), and SEQ ID NO: 12 (ComPΔ28$_{SFC}$). In certain aspects, the glycosylation tag comprises a region corresponding to the region of SEQ ID NO: 2 (ComP$_{110264}$: ENV58402.1) comprising the serine residue at position 82 of SEQ ID NO: 2 (ComP$_{110264}$: ENV58402.1) flanked by a disulfide bond connecting the alpha beta loop to the beta strand region. In certain aspects, the glycosylation tag comprises an amino acid sequence that is at least 80%, 85%, 90%, 95%, 96%, 97%, 98%, 99%, or 100% identical to an amino acid selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and NGVISASATTNVASSA (SEQ ID NO: 44), wherein said glycosylation tag comprises the serine residue corresponding to the conserved serine residue at position 84 of SEQ ID NO: 1 (ComP$_{ADP1}$: AAC45886.1). In certain aspects, the glycosylation tag comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and NGVISASATTNVASSA (SEQ ID NO: 44), or a variant thereof having one, two, three, four, five, six, or seven amino acid substitutions, additions, and/or deletions, wherein the variant maintains the serine residue corresponding to the conserved serine residue at position 84 of SEQ ID NO: 1 (ComPADP1: AAC45886.1). In certain aspects, the glycosylation tag comprises the amino acid consensus sequence of SEQ ID NO: 37, or a fragment of at least 5, 10, 15, 20, 30, 35, or 40 consecutive amino acids thereof, wherein said glycosylation tag fragment comprises the serine residue corresponding to the conserved serine residue at position 84 of SEQ ID NO: 1 (ComP$_{ADP1}$: AAC45886.1), or a variant thereof having one, two, three, four, five, six, or seven amino acid substitutions, additions, and/or deletions, wherein the variant maintains the serine residue corresponding to the conserved serine residue at position 84 of SEQ ID NO: 1 (ComPADP1: AAC45886.1). In certain aspects, the glycosylation tag comprises the amino acid consensus sequence of SEQ ID NO: 38 or 45, or a fragment of at least 5, 6, 7, 8, 9, 10, 11, 12, 13, 14, 15, 16, 17, 18, 19, or 20 consecutive amino acids thereof, wherein said glycosylation tag fragment comprises the serine residue corresponding to the conserved serine residue at position 84 of SEQ ID NO: 1 (ComP$_{ADP1}$: AAC45886.1), or a variant thereof having one, two, three, four, five, six, or seven amino acid substitutions, additions, and/or deletions, wherein the variant maintains the serine residue corresponding to the conserved serine residue at position 84 of SEQ ID NO: 1 (ComPADP1: AAC45886.1). In certain aspects, the glycosylation tag comprises a ComP protein amino acid sequence that corresponds to any of amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, or 82 of SEQ ID NO: 1 (ComP$_{ADP1}$: AAC45886.1) to any of amino acid residues 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, or 147 of SEQ ID NO: 1 (ComP$_{ADP1}$: AAC45886.1). In certain aspects, the glycosylation tag comprises an amino acid sequence comprising any of amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, or 82 of SEQ ID NO: 1 (ComP$_{ADP1}$: AAC45886.1) to any of amino acid residues 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, or 147 of SEQ ID NO: 1 (ComP$_{ADP1}$: AAC45886.1). In certain aspects, the glycosylation tag is not more than 124, 120, 115, 110, 100, 90, 80, 75, 70, 60, 50, 40, 30, 25, 20, 15, 10, or 5 amino acids in length. In certain aspects, the glycosylation tag is covalently linked to an oligo- or polysaccharide at a serine residue corresponding to the conserved serine residue at position 84 of SEQ ID NO: 1 (ComP$_{ADP1}$: AAC45886.1). In certain aspects, the oligo- or polysaccharide is produced by a bacteria from the genus *Streptococcus*. In certain aspects, the polysaccharide is a *S. pneumoniae, S. agalactiae*, or *S. suis* capsular polysaccharide. In certain aspects, the capsular polysaccharide is CPS14, CPS8, CPS9V, or CPS15b. In certain aspects, the capsular polysaccharide is CPS8. In certain aspects, the oligo- or polysaccharide is produced by a bacteria from the genus *Klebsiella*. In certain aspects, the oligo- or polysaccharide is a *Klebsiella pneumoniae, Klebsiella varricola, Klebsiella michinganenis*, or *Klebsiella oxytoca* capsular polysaccharide. In certain aspects, the polysaccharide is a *Klebsiella pneumoniae* capsular polysaccharide. In certain aspects, the polysaccharide is a serotype K1 or serotype K2 capsular polysaccharide of *Klebsiella pneumoniae*. In certain aspects, the oligo- or polysaccharide comprises a glucose at its reducing end.

Provided for herein is a fusion protein, for example certain aspects and features of which are described in this paragraph, comprising a ComP glycosylation tag as described above. In certain aspects, the fusion protein is glycosylated at a serine residue on the glycosylation tag corresponding to the serine residue at position 84 of SEQ ID NO: 1 (ComP$_{ADP1}$: AAC45886.1). In certain aspects, the fusion protein comprises a carrier protein selected from the group consisting of diphtheria toxoid CRM197, tetanus toxoid, *Pseudomonas aeruginosa* Exotoxin A (EPA), tetanus toxin C fragment, cholera toxin B subunit, and *Haemophilus influenza* protein D, or a fragment thereof. In certain aspects, the fusion protein comprises an amino acid linker sequence.

Provided herein is a method of in vivo conjugation of an oligo- or polysaccharide to an acceptor polypeptide, for example certain aspects and features of which are described in this paragraph, the method comprising covalently linking the oligo- or polysaccharide to the acceptor polypeptide with a PglS oligosaccharyltransferase (OTase), wherein the acceptor polypeptide comprises a ComP protein or a glycosylation tag fragment thereof. In certain aspects, the ComP protein or glycosylation tag fragment thereof is linked to a heterologous carrier protein. In certain aspects, the PglS OTase is PglS$_{110264}$, PglS$_{ADP1}$, PglS$_{GFJ-2}$, PglS$_{50v1}$, PglS$_{4466}$, or PglS$_{SFC}$. In certain aspects, the ComP protein is ComP$_{110264}$, ComP$_{ADP1}$, ComP$_{GFJ-2}$, ComP$_{50v1}$, ComP$_{4466}$, or ComP$_{SFC}$. In certain aspects, the PglS OTase is PglS$_{ADP1}$. In certain aspects, the PglS OTase is PglS$_{ADP1}$ but the ComP protein is not ComP$_{ADP1}$. In certain aspects, the PglS OTase is PglS$_{ADP1}$ and the ComP protein is ComP$_{110264}$. In certain aspects, the oligo- or polysaccharide is linked to the ComP protein or glycosylation tag fragment thereof at a serine residue corresponding to the serine residue at position 84 of SEQ ID NO: 1 (ComP$_{ADP1}$: AAC45886.1). In certain aspects, the in vivo conjugation occurs in a host cell. In certain aspects, the host cell is a bacterial cell. In certain aspects, the host cell is *E. coli*. In certain aspects, the method comprises culturing a host cell that comprises: (a) a genetic cluster encoding for the proteins required to synthesize the oligo- or polysaccharide; (b) a PglS OTase; and (3) the acceptor polypeptide. In certain aspects, production of the oligo- or polysaccharide is enhanced by the *K. pneumoniae* transcriptional activator rmpA (*K. pneumoniae* NTUH K-2044) or a homolog of the *K. pneumoniae* transcriptional activator rmpA (*K. pneumoniae* NTUH K-2044). In certain aspects, the carrier protein is selected from the group consisting of diphtheria toxoid CRM197, tetanus toxoid, *Pseudomonas aeruginosa* Exotoxin A (EPA), tetanus toxin C fragment, cholera toxin B subunit, and *Haemophilus influenza* protein D, or a fragment thereof. In certain aspects, the method produces a conjugate vaccine.

Provided for herein is a host cell, for example certain aspects and features of which are described in this paragraph, comprising (a) a genetic cluster encoding for the proteins required to synthesize an oligo- or polysaccharide; (b) a PglS OTase; and (3) an acceptor polypeptide comprising a ComP protein or a glycosylation tag fragment thereof. In certain aspects, the acceptor polypeptide is a fusion protein. In certain aspects, the host cell comprises a nucleic acid encoding the PglS OTase. In certain aspects, the host cell comprises a nucleic acid encoding the acceptor polypeptide.

Provided for herein is an isolated nucleic acid, for example certain aspects and features of which are described in this paragraph, encoding a Comp glycosylation tag described above and/or a fusion protein described above. In certain aspects, the nucleic acid is a vector. Also provide for is a host cell comprising the isolated nucleic acid.

Provided for herein is a composition comprising a conjugate vaccine described above or a fusion protein described above, and an adjuvant.

Provided for herein is a method of inducing a host immune response against a bacterial pathogen, for example certain aspects and features of which are described in this paragraph, the method comprising administering to a subject in need of the immune response an effective amount of a conjugate vaccine described above, the fusion protein described above, or the composition described above. In certain aspects, the immune response is an antibody response. In certain aspects, the immune response is selected from the group consisting of an innate response, an adaptive response, a humoral response, an antibody response, cell mediated response, a B cell response, a T cell response, cytokine upregulation or downregulation, immune system cross-talk, and a combination of two or more of said immune responses. In certain aspects, the immune response is selected from the group consisting of an innate response, a humoral response, an antibody response, a T cell response, and a combination of two or more of said immune responses.

Provided for herein is a method of preventing or treating a bacterial disease and/or infection in a subject, for example certain aspects and features of which are described in this paragraph, comprising administering to a subject in need thereof a conjugate vaccine described above, a fusion protein described above, or a composition described above. In certain aspects, the infection is a localized or systemic infection of skin, soft tissue, blood, or an organ, or is auto-immune in nature. In certain aspects, the disease is pneumonia. In certain aspects, the infection is a systemic infection and/or an infection of the blood. In certain aspects, the subject is a human. In certain aspects, the composition is administered via intramuscular injection, intradermal injection, intraperitoneal injection, subcutaneous injection, intravenous injection, oral administration, mucosal administration, intranasal administration, or pulmonary administration.

Provided for herein is a method of producing a pneumococcal conjugate vaccine against pneumococcal infection, the method comprising: (a) isolating a bioconjugate described above or a glycosylated fusion protein described above; and (b) combining the isolated conjugate vaccine or isolated glycosylated fusion protein with an adjuvant.

BRIEF DESCRIPTION OF THE DRAWINGS

FIGS. 1A, 1B, and 1C show that PglS (1C), but not PglB (1B) or PglL (1A), can conjugate pneumococcal CPS14 to its cognate acceptor/carrier protein. Western blot analysis on E. coli whole cell lysates probing for hexa-histidine tagged acceptor protein variants.

FIG. 2 shows that PglS from A. baylyi ADP1 ($PglS_{ADP1}$) can transfer multiple pneumococcal capsular polysaccharides to ComP from A. baylyi ADP1 ($ComP_{ADP1}$). Western blot analysis on purified $ComP_{ADP1}$ variants probing for hexa-histidine tagged $ComP_{ADP1}$ variants and either pneumococcal CPS8 (left), CPS9V (middle), or CPS14 (right). Co-localization of the anti-His signals with the anti-glycan signals indicates that $ComP_{ADP1}$ was glycosylated with the correct pneumococcal polysaccharide. The asterisk indicates samples that were treated with proteinase K for 2 hours.

FIG. 3A,B. FIGS. 3A and 3B show that $PglS_{ADP1}$ can transfer the K1 and K2 capsular polysaccharides of K. pneumoniae to $ComP_{ADP1}$. Western blot analysis on E. coli whole cell lysates probing for hexa-histidine tagged $ComP_{ADP1}$ variants and RNA polymerase. RNA polymerase was used as a loading control.

FIG. 4A shows mass spectrometry of CPS14-$ComP_{ADP1}$ identified a single glycosylated peptide. ISASNATTNVATAT (SEQ ID NO: 22).

FIG. 4B shows mass spectrometry of CPS14-$ComP_{ADP1}$ identified a single glycosylated peptide.

FIG. 5 shows Serine 84 of $ComP_{ADP1}$ is the site of PglS dependent glycosylation. Western blot analysis on E. coli whole cell lysates probing for hexa-histidine tagged $ComP_{ADP1}$ variants and the Campylobacter jejuni heptasaccharide. The ComP[S84A]$_{ADP1}$ variant was expressed; however, was not glycosylated as indicated by the absence of any reactive bands probing with the anti-hR6 heptasaccharide antisera.

FIG. 6. FIG. 6 lists ComP ortholog amino acid sequences. The site of predicted glycosylation is bolded, flanked by a predicted disulfide bond (underlined) linking the predicted alpha beta loop to the beta strand region.

FIG. 7 shows that $PglS_{ADP1}$, but not $PglS_{110264}$, efficiently glycosylates both its cognate $ComP_{ADP1}$ as well as $ComP_{110264}$ from A. soli CIP 110264. Western blot analysis on E. coli whole cell lysates probing for hexa-histidine tagged ComP variants and RNA polymerase. RNA polymerase was used as a loading control.

FIG. 8 shows that $PglS_{ADP1}$ efficiently glycosylates DsbA-ComPΔ28$_{110264}$ fusions but not DsbA-ComPΔ28$_{ADP1}$ fusions. All fusions either had a triple alanine peptide (AAA; SEQ ID NO: 24) or glycine-glycine-glycine-serine peptide (GGGS; SEQ ID NO: 23) linking DsbA to either a hexa-histidine tagged ComPΔ28$_{110264}$ or ComPΔ28$_{ADP1}$. Western blot analysis on E. coli whole cell lysates probing for hexa-histidine tagged ComP variants and RNA polymerase. RNA polymerase was used as a loading control.

FIG. 9 shows that $PglS_{ADP1}$ efficiently glycosylates MBP-ComPΔ28$_{110264}$ fusions but not MBP-ComPΔ28$_{ADP1}$ fusions. All fusions either had a triple alanine peptide (AAA; SEQ ID NO: 24) or glycine-glycine-glycine-serine peptide (GGGS; SEQ ID NO: 23) linking maltose binding protein (MBP) to either a hexa-histidine tagged ComPΔ28$_{110264}$ or ComPΔ28$_{ADP1}$. Western blot analysis on E. coli whole cell lysates probing for hexa-histidine tagged ComP variants and RNA polymerase. RNA polymerase was used as a loading control.

FIG. 10 $PglS_{ADP1}$, but not $PglS_{110264}$, efficiently EPA-GGGS-ComPΔ28$_{110264}$ fusions. Western blot analysis on E. coli whole cell lysates or periplasmic extracts probing for hexa-histidine tagged ComP variants. EPA-GGGS—exotoxin A with a glycine-glycine-glycine-serine peptide (GGGS; SEQ ID NO: 23) linking a hexa-histidine tagged ComPΔ28$_{110264}$ variant.

FIG. 11. FIG. 11 shows amino acid sequences of representative ComPΔ28$_{110264}$ fusion proteins.

FIGS. 12A, 12B, and 12C show that a monovalent CPS14-$ComP_{ADP1}$ bioconjugate vaccine induces serotype specific IgG antibodies.

FIG. 13 shows that a trivalent bioconjugate vaccine against serotypes 8, 9V, and 14 induces serotype specific IgG titers at comparable levels to Prevnar 13.

FIG. 14. FIG. 14 lists ComP A78 ortholog amino acid sequences in which the amino acids corresponding to the 28 N-terminal amino acids of SEQ ID NO: 1 ($ComP_{ADP1}$: AAC45886.1) have been removed. The site of predicted glycosylation is bolded, flanked by a predicted disulfide bond (underlined) linking the predicted alpha beta loop to the beta strand region.

FIG. 15. FIG. 15 shows an alignment of a region ComP sequences including the serine (S) residue (boxed) corresponding to the serine residue at position 84 of SEQ ID NO: 1 ($ComP_{ADP1}$: AAC45886.1).

FIG. 16 shows higher energy collisional dissociation (HCD) fragmentation spectra of GluC digested CPS14-ComP bioconjugates. GluC digested CPS14-ComP was subjected to HCD fragmentation enabling the confirmation of a semi-GluC derived single peptide attached to a glycan with the CPS14 repeating subunit. Additional glycopeptides were also observed decorated with extended glycans corresponding to up to four tetrasaccharide repeat units.

FIG. 17 shows higher energy collisional dissociation (HCD) fragmentation spectra of GluC digested ComP glycosylated with the C. jejuni heptasaccharide (ComP-Glycan$_{Cj}$). GluC digested ComP-Glycan$_{Cj}$ was subjected to HCD fragmentation enabling the confirmation of a single peptide attached to a glycan with the CPS14 repeating subunit. Low collision energies regimes were undertaken to confirm the glycosylation of the peptide ISASNATTN-VATAT (SEQ ID NO: 22) with a 1380.53 Da glycan corresponding to 6*HexNAc,1*Hexose.

FIG. 18 shows higher energy collisional dissociation (HCD) fragmentation spectra of GluC digested ComP glycosylated with the C. jejuni heptasaccharide (ComP-Glycan$_{Cj}$). GluC digested ComP-Glycan$_{Cj}$ was subjected to HCD fragmentation enabling the confirmation of a single peptide attached to a glycan with the CPS14 repeating subunit. High collision energies regimes were undertaken to confirm the glycosylation of the peptide ISASNATTN-VATAT (SEQ ID NO: 22) with a 1380.53 Da glycan corresponding to 6*HexNAc,1*Hexose.

FIG. 19A-I. FIG. 19A-I shows that the oligosaccharyl-transferase PglS can glycosylate the acceptor protein ComP with the pneumococcal CPS14 polysaccharide. *E. coli* SDB1 cells co-expressing an acceptor protein (DsbA, AcrA, or ComP), an OTase (PglL, PglB, or PglS), and the CPS14 polysaccharide were analyzed for protein glycosylation via western blot analysis of the affinity purified acceptor proteins. (A-C): DsbA purified from SDB1 cells in the presence or absence of PglL. (A): Anti-His channel probing for hexa-histidine tagged DsbA. (B): Anti-glycan channel probing for CPS14. (C): Merged images for panels A and B. (D-F): AcrA purified from SDB1 cells in the presence or absence of PglB. (D): Anti-His channel probing for hexa-histidine tagged AcrA. (E): Anti-glycan channel probing for CPS14. (F): Merged images for panels D and E. (G-I): ComP purified from SDB1 cells in the presence or absence of PglS. (G): Anti-His channel probing for hexa-histidine tagged ComP. (H): Anti-glycan channel probing for CPS14. (I): Merged images for panels G and H. The asterisk indicates samples that were proteinase K treated for 1 h at 55° C.

FIG. 20A,B shows higher energy collisional dissociation (HCD) fragmentation spectra of GluC digested CPS14-ComP bioconjugates. GluC digested CPS14-ComP was subjected to HCD fragmentation enabling the confirmation of a single peptide attached to a glycan with the CPS14 repeating subunit. High collision energies (A) and low collision energies (B) regimes were undertaken to confirm the glycosylation of the peptide ISASNATTN-VATAT (SEQ ID NO: 22) with a 1378.47 Da glycan corresponding to HexNAc2Hexose6.

FIG. 21A-F. FIG. 21A-F shows Western blot analysis of CPS8-ComP and CPS9V-ComP glycoproteins. *E. coli* SDB1 cells were prepared co-expressing ComP, PglS, and either the pneumococcal CSP8 or CPS9V. Affinity purified glycosylated ComP from each strain was analyzed for protein glycosylation via western blot analysis. (A-C): Western blot analysis of CPS8-ComP bioconjugates compared against ComP alone (A): Anti-His channel probing for hexa-histidine tagged ComP purified from SDB1 expressing CPS8 in the presence or absence of PglS. (B): Anti-glycan channel probing for CPS8. (C): Merged images for panels A and B. (D-F): Western blot analysis of CPS9V-ComP bioconjugates compared against ComP alone (D): Anti-His channel probing for hexa-histidine tagged ComP purified from SDB1 expressing CPS9V in the presence or absence of PglS. (E): Anti-glycan channel probing for CPS9V. (F): Merged images for panels D and E. The asterisk indicates samples that were proteinase K treated for 1 h at 55° C.

FIG. 22A-F. FIG. 22A-F shows IgG responses of mice vaccinated with ComP, PREVNAR 13®, a monovalent CPS14-ComP bioconjugate and a trivalent CPS8-/CPS9V-/CPS14-ComP bioconjugate. Groups of mice were vaccinated with ComP alone, PREVNAR 13®, a monovalent CPS14-ComP bioconjugate vaccine, or a CPS8-/CPS9V-/CPS14-ComP bioconjugate vaccine. Sera were as collected on day 49 and analyzed for serotype specific IgG responses via ELISA compared against sera collected on day 0. (A-C): No detectable increases in IgG responses were detected in placebo vaccinated mice for serotypes 8 (A), 9V (B), or 14 (C). (D-F): PREVNAR 13® vaccinated mice did not have detectable IgG responses titer increases to serotype 8 (D), but did have IgG responses increases in IgG titers specific to serotype 9V (E) and 14 (F). Unpaired t-tests (Mann-Whitney) were performed to statistically analyze pre-immune sera from day 49 sera. P values for each case tested were **** p=0.0001. Each dot represents a single vaccinated mouse. Error bars indicate the standard deviation of the mean.

FIG. 22G-L. FIG. 22G-L shows IgG responses of mice vaccinated with ComP, PREVNAR 13®, a monovalent CPS14-ComP bioconjugate and a trivalent CPS8-/CPS9V-/CPS14-ComP bioconjugate. Groups of mice were vaccinated with ComP alone, PREVNAR 13®, a monovalent CPS14-ComP bioconjugate vaccine, or a CPS8-/CPS9V-/CPS14-ComP bioconjugate vaccine. Sera were as collected on day 49 and analyzed for serotype specific IgG responses via ELISA compared against sera collected on day 0. (G-I): Mice vaccinated with a CPS14-ComP bioconjugate vaccine did not have IgG responses detectable increases in IgG titers specific to serotypes 8 (G) or 9V (H), but did have IgG responses statistically significant IgG titer increases to serotype 14 (I). (J-L): Trivalent CPS8-/CPS9V-/CPS14-ComP bioconjugate vaccinated mice all had statistically significant IgG responses increases in IgG titers to serotypes 8 (J), 9V (K), and 14 (L). Unpaired t-tests (Mann-Whitney) were performed to statistically analyze pre-immune sera from day 49 sera. P values for each case tested were **** p=0.0001. Each dot represents a single vaccinated mouse. Error bars indicate the standard deviation of the mean.

FIG. 23A,B. FIG. 23A,B shows bactericidal activity of sera from vaccinated mice against *S. pneumoniae* serotypes 8 and 14. Opsonophagocytosis assays (OPA) of sera from mice vaccinated with either buffer control, PREVNAR 13®, or bioconjugate vaccine against both *S. pneumoniae* serotypes 8 (A) and 14 (B). Serotype-specific commercial rabbit anti-*S. pneumoniae* sera were used as positive controls. A 5% (v/v) sample serum and a bacterial MOT of 0.01 were added to fresh whole blood from naive mice to perform the assay. Viable bacterial counts were performed after 4 h of incubation. To determine bacterial killing, viable bacterial counts from tubes incubated with sample sera were compared to those incubated with control naive mouse sera. Results are expressed as percent bacterial killing for individual mice, with horizontal bars representing the standard deviation of the mean.

FIG. 24A,B. FIG. 24A,B shows analysis of EPA glycosylation with the CPS8 capsular polysaccharide. Western blot analysis of EPA-CPS8 bioconjugates compared against EPA alone. (A—Left panel) Anti-His channel probing for hexa-histidine tagged EPA purified from SDB1 expressing CPS8 in the presence or absence of PglS. (A—Middle panel) Anti-glycan channel probing for CPS8. (A—Right panel) Merged images for left and middle panels. (B): EPA-CPS8 separated on a SDS polyacrylamide gel stained with Coomassie.

FIG. 24C shows intact protein mass spectrometry analysis showing the MS1 mass spectra for purified EPA-CPS8. The EPA fusion protein has a theoretical mass of 79,526.15 Daltons and can be observed as the peak at 79,514.76. The EPA fusion protein was also observed in multiple states of increasing mass corresponding to the CPS8 repeating subunit, which has a theoretical mass of 662 Daltons. Varying glycoforms of the EPA-CPS8 were observed and are denoted by "g$^{numeric}$" where "g" stands for glycoform and the "numeric" corresponds to the number of repeating CPS8 subunits. The EPA fusion protein was modified with up to 11 repeating subunits of the CPS8 glycan. Panel D provides a zoomed in view of the varying EPA-CPS8 glycoforms.

FIG. 24D provides a zoomed in view of the varying EPA-CPS8 glycoforms from FIG. 24C.

FIG. 25A,B. FIG. 25A,B shows analysis of immune responses to ComP-CPS8 and EPA-CPS8 bioconjugates in mice. (A): Titers of CPS8 IgG antibodies in mice immunized with CPS8 bioconjugate vaccines. Mouse groups were as follows: EPA (n=9, mice vaccinated with 5 μg of total protein), ComP-CPS8 (n=10, mice vaccinated with 5 μg total polysaccharide), and EPA-CPS8 (n=10, mice vaccinated with 100 ng of total polysaccharide). All mice were immunized with 100 μL of a vaccine diluted 1:1 with Imject Alum Adjuvant on days 1, 14, and 28. Sera were collected on day 4. For the titration, ELISA plates were coated with whole cell serotype 8 pneumococci and incubated with 2-fold serial dilutions of sera. Titers for individual mice are shown, with horizontal bars representing the standard error of the mean. Statistically significant titers compared to the EPA placebo group are denoted with asterisk and were determined using Kruskal-Wallis one-way Anova. , P=0.0223 and , P<0.0001. For analysis and representation purposes, negative titer values (<100) were given an arbitrary value of 10. (B): Opsonophagocytosis killing of S. pneumoniae serotype 8 by day 42 sera from mice immunized with ComP-CPS8 and EPA-CPS8 bioconjugate vaccines. The same mouse groups described for the IgG titers were employed for the OPA. A 40% (vol/vol) sample of serum and bacterial MOT of 0.01 were added to fresh whole blood from naïve mice to perform the assay. Results are expressed as percent bacterial killing for individual mice, with horizontal bars representing the standard error of the mean. Statistically significant killing compared to the EPA placebo group is denoted with asterisk and were determined using Kruskal-Wallis one-way Anova. , P=0.0015.

FIG. 26A,B,C shows that a conserved and homologous serine is believed to be the site of glycosylation in ComP proteins from *A. baylyi* ADP1 and *A. soli* 110264. Serines 82 and 84 of ComP$_{ADP1}$ and the homologous serines 79 and 82 of ComP$_{110264}$ were mutated to an alanine and probed for glycosylation in the presence of PglS and the serotype 8 capsular polysaccharide. (A-C) SDB1 cells expressing ComP variants in the presence of PglS and CPS8 were probed via western blotting for protein glycosylation. (A) Anti-His channel probing for ComP expression and glycosylation. (B) Anti-glycan channel probing for CPS8. (C) Merged image for panels A and B.

FIG. 27A,B,C. FIG. 27A,B,C shows an analysis of EPA glycosylation with the *Klebsiella pneumoniae* K1 and K2 capsular polysaccharides. Western blot analysis of purified the (A) non-glycosylated EPA, (B) EPA glycosylated with the *K. pneumoniae* K1 capsular polysaccharide, or (C) EPA glycosylated with the *K. pneumoniae* K2 capsular polysaccharide. The "g$^0$" denotes the non-glycosylated EPA fusion and "g'''" denotes the EPA fusion glycosylated with different sized K1 or K2 repeating subunits as depicted in panel B or C, respectively.

FIG. 28A,B shows intact protein mass spectrometry analysis showing the MS1 mass spectra for purified EPA-K2. The EPA fusion protein has a theoretical mass of 79,526.15 Daltons and can be observed as the peak at 79,518.73. The EPA fusion protein was also observed in multiple states of increasing mass corresponding to the *K. pneumoniae* K2 capsular polysaccharide repeating subunit, which has a theoretical mass of 662 Daltons. (A) Varying glycoforms of the EPA-K2 were observed and are denoted by "g$^{numeric}$" where "g" stands for glycoform and "numeric" corresponds to the number of repeating K2 subunits. The EPA fusion protein was modified with up to 11 repeating subunits of the K2 capsule. (B) A zoomed in view of A is also provided.

DETAILED DESCRIPTION

Figure 1:
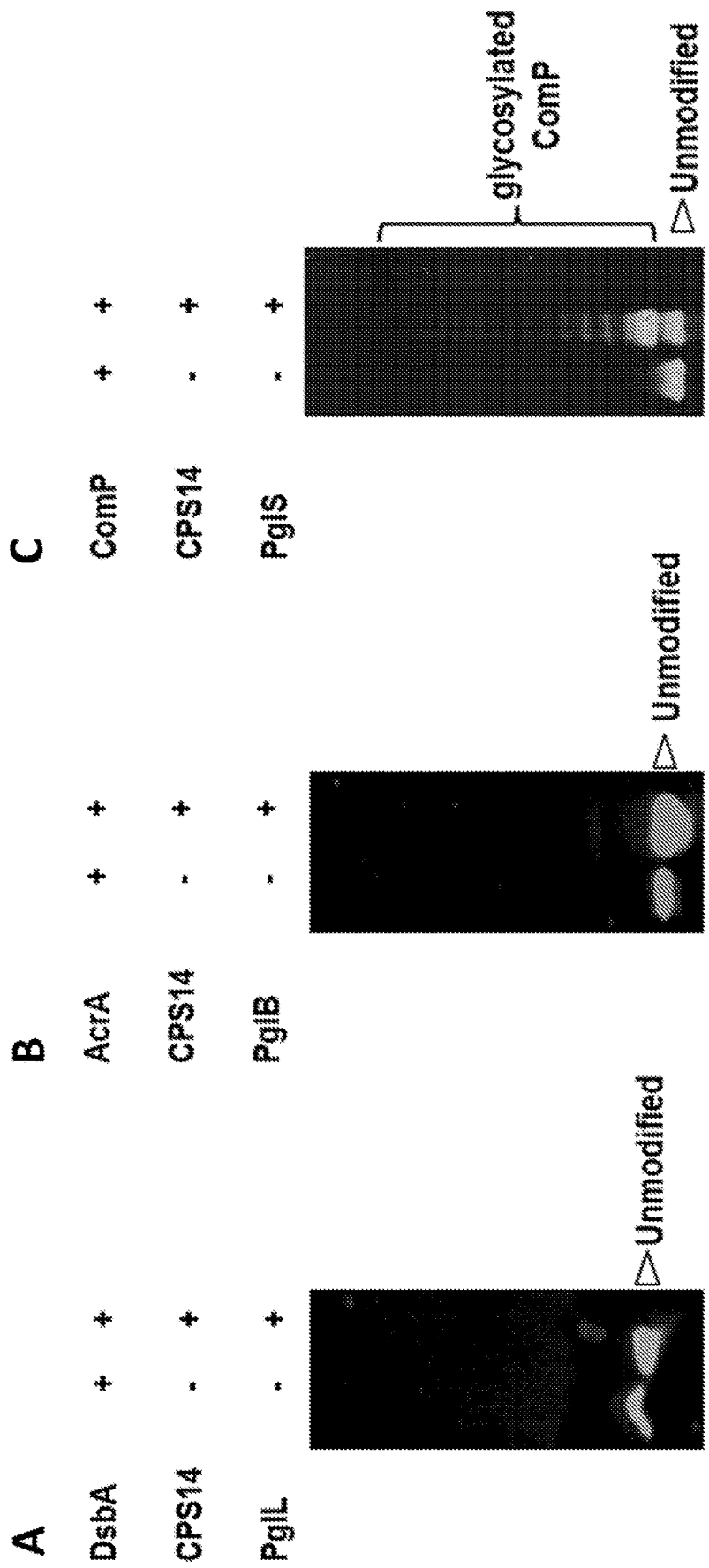
FIG. 1A-C.

To the extent necessary to provide descriptive support, the subject matter and/or text of the appended claims is incorporated herein by reference in their entirety.

It will be understood by all readers of this written description that the exemplary aspects and embodiments described and claimed herein may be suitably practiced in the absence of any recited feature, element or step that is, or is not, specifically disclosed herein.

It is to be noted that the term "a" or "an" entity refers to one or more of that entity; for example, "a polysaccharide," is understood to represent one or more polysaccharides. As such, the terms "a" (or "an"), "one or more," and "at least one" can be used interchangeably herein.

Furthermore, "and/or" where used herein is to be taken as specific disclosure of each of the specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising" or "comprises" otherwise analogous aspects described in terms of "consisting of," "consists of," "consisting essentially of," and/or "consists essentially of," and the like are also provided.

Unless defined otherwise, technical and scientific terms used herein have the same meaning as commonly understood by one of ordinary skill in the art to which this disclosure is related. Numeric ranges are inclusive of the numbers defining the range. Even when not explicitly identified by "and any range in between," or the like, where a list of values is recited, e.g., 1, 2, 3, or 4, unless otherwise stated, the disclosure specifically includes any range in between the values, e.g., 1 to 3, 1 to 4, 2 to 4, etc.

The headings provided herein are solely for ease of reference and are not limitations of the various aspects or aspects of the disclosure, which can be had by reference to the specification as a whole.

As used herein, the term "non-naturally occurring" condition, substance, polypeptide, polynucleotide, composition, entity, organism, individual, and/or any combination thereof, or any grammatical variants thereof, is a conditional term that explicitly excludes, but only excludes, those forms that are well-understood by persons of ordinary skill in the art as being "naturally-occurring," or that are, or might be at any time, determined or interpreted by a judge or an administrative or judicial body to be, "naturally-occurring."

As used herein, the term "bioconjugate" is a molecule comprising a peptide, oligopeptide, polypeptide, etc. covalently linked to a sugar (saccharide, oligosaccharide, polysaccharide, etc.).

As used herein, an "oligo- or polysaccharide" refers to a carbohydrate consisting of more than one monosaccharide unit bonded together.

As used herein, the term "lipid-linked oligo- or polysaccharide" refers to any isoprenoid moiety linked by a pyrophosphate to an oligo- or polysaccharide.

As used herein, the term "fusion protein" refers to a polypeptide comprising two or more amino acid sequences that are covalently linked in an arrangement that they would not naturally occur. Such amino acid sequences can include sequences from heterologous proteins, from different regions of the same protein, and/or repeated sequences from the same protein.

As used herein, the term "identity" or "identical" e.g., "percent (%) identity" or "percent (%) identical" to an amino acid sequence or to a nucleotide sequence disclosed herein refers to a relationship between two or more nucleotide sequences or between two or more amino acid sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window of the entire length of a reference sequence. In order to optimally align sequences for comparison, the portion of a nucleotide or amino acid sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using, e.g., the program "BLAST" which is available from the National Center for Biotechnology Information, and which program incorporates the programs BLASTN (for nucleotide sequence comparison) and BLASTP (for amino acid sequence comparison), which programs are based on the algorithm of Karlin and Altschul (*Proc. Natl. Acad. Sci. USA* 90(12):5873-5877, 1993).

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-standard amino acids. While a polypeptide can be derived from a natural biological source or produced by recombinant technology, is not necessarily translated from a designated nucleic acid sequence. It can be generated in any manner, including by chemical synthesis.

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein.

By an "isolated" polypeptide or a fragment, variant, or derivative thereof or the like is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are recombinant polypeptides that have been separated, fractionated, or partially or substantially purified by any suitable technique. An isolated polypeptide or fragment, variant, or derivative thereof or the like can be associated, bound, etc., with a cofactor. Likewise, a purified or purified and isolated polypeptide or fragment, variant, or derivative thereof or the like can be associated, bound, etc., with a cofactor.

Other polypeptides disclosed herein are fragments, derivatives, analogs, or variants of the polypeptides disclosed herein, and any combination thereof. The terms "fragment," "variant," "derivative" and "analog" when referring to polypeptide subunit or multimeric protein as disclosed herein can include any polypeptide or protein that retain at least some of the activities of the complete polypeptide or protein (for example retain the ability to be glycosylated), but which is structurally different. Fragments of polypeptides include, for example, proteolytic fragments, as well as deletion fragments. Variants include fragments as described above, and also polypeptides with altered amino acid sequences due to amino acid substitutions, deletions, or insertions. Variants can occur spontaneously or be intentionally constructed. Intentionally constructed variants can be produced using art-known mutagenesis techniques. Variant polypeptides can comprise conservative or non-conservative amino acid substitutions, deletions or additions (one of ordinary skill in the art would understand that a "conservative amino acid substitution" is not the same as a "conserved amino acid residue/position"). Variant polypeptides can also be referred to herein as "polypeptide analogs." Derivatives are variants of polypeptides that have been altered so as to exhibit additional features not found on the native polypeptide. Examples include fusion proteins. As used herein a "derivative" also refers to a subject polypeptide having one or more amino acids chemically derivatized by reaction of a functional side group. Also included as "derivatives" are those peptides that contain one or more standard or synthetic amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

As used herein, a "single amino acid substitution" means replacing an amino acid residue in a polypeptide sequence with a different amino acid residue (such as replacing the native residue in a wild-type sequence with a non-native amino acid), unless otherwise specified. Also encompassed by the disclosure are a "single amino acid deletion" and/or a "single amino acid insertion."

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate protein activity or functionality are well-known in the art (see, e.g., Brummell et al. *Biochem.* 32: 1180-1 187 (1993); Kobayashi et al. *Protein Eng.* 12(10):879-884 (1999); Burks et al. *Proc. Natl. Acad. Sci. USA* 94:412-417 (1997)).

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "coding region" is a portion of nucleic acid comprising codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode a selection marker gene and a gene of interest. In addition, a vector, polynucleotide, or nucleic acid can encode heterologous coding regions, either fused or unfused to a nucleic acid encoding a polypeptide subunit or fusion protein as provided herein. Heterologous coding regions include without limitation specialized elements or motifs, such as a secretory signal peptide or a heterologous functional domain.

In certain aspects, the polynucleotide or nucleic acid is DNA. In the case of DNA, a polynucleotide comprising a nucleic acid that encodes a polypeptide normally can include a promoter and/or other transcription or translation regulatory elements operably associated with one or more coding regions. An operable association or linkage can be when a coding region for a gene product, e.g., a polypeptide, can be associated with one or more regulatory sequences in such a way as to place expression of the gene product under the influence or control of the regulatory sequence(s). Two DNA fragments (such as a polypeptide coding region and a promoter associated therewith) can be "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription regulatory elements, besides a promoter, for example enhancers, operators, repressors, and transcription termination signals, can be operably associated with the polynucleotide to direct cell-specific transcription.

A variety of transcription regulatory regions are known to those skilled in the art. These include, without limitation, transcription regulatory regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription regulatory regions include those derived from vertebrate genes such as actin, heat shock protein, bovine growth hormone and rabbit β-globin, as well as other sequences capable of controlling gene expression in eukaryotic cells. Additional suitable transcription regulatory regions include tissue-specific promoters and enhancers.

Similarly, a variety of translation regulatory elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other aspects, a polynucleotide can be RNA, for example, in the form of messenger RNA (mRNA).

Polynucleotide and nucleic acid coding regions can be associated with additional coding regions that encode secretory or signal peptides, which direct the secretion of a polypeptide encoded by a polynucleotide as disclosed herein.

A "vector" is nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art. Illustrative types of vectors include plasmids, phages, viruses and retroviruses.

A "transformed" cell, or a "host" cell, is a cell into which a nucleic acid molecule has been introduced by molecular biology techniques. As used herein, the term transformation encompasses those techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a prokaryotic cell (e.g., bacterial) or a eukaryotic cell (e.g., mammalian).

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

Overview.

Conjugate vaccines, consisting of a polysaccharide linked to a protein, are lifesaving prophylactics. Traditionally, conjugate vaccines are manufactured using chemical methodologies. However, in vivo bacterial conjugations have emerged as manufacturing alternatives. In vivo conjugation (bioconjugation) is reliant upon an oligosaccharyltransferase to attach polysaccharides to proteins. Currently, the oligosaccharyltransferases employed for bioconjugations are not suitable for the generation of conjugate vaccines when the polysaccharides contain glucose at the reducing end. This limitation has enormous implications as ~75% of Streptococcus pneumoniae capsules contain glucose as the reducing end sugar. Disclosed herein is the use of an O-linked oligosaccharyltransferase to generate the first ever polyvalent pneumococcal bioconjugate vaccine with polysaccharides containing glucose at their reducing end. Pneumococcal bioconjugates were immunogenic, protective, and rapidly produced with recombinant techniques. Certain aspects disclosed herein provide for the engineering, characterization, and immunological responses of a polyvalent pneumococcal bioconjugate vaccine using the natural acceptor protein ComP as a vaccine carrier as well as a monovalent pneumococcal bioconjugate vaccine using a conventional vaccine carrier; e.g., in certain aspects, containing the *Pseudomonas aeruginosa* exotoxin A protein. This establishes a platform to overcome limitations of other conjugating enzymes enabling the development of bioconjugate vaccines for many important human and animal pathogens.

Even with the introduction and implementation of pneumococcal conjugate vaccines over the last two decades, ~1.5 million deaths are still attributed to *S. pneumoniae* each year. This is due in part to the 90+ serotypes of *S. pneumoniae* and the complex manufacturing methods required to synthesize pneumococcal conjugate vaccines. Together these factors hinder global distribution and development of broader, more protective variations of the vaccines. To expedite development and lower manufacturing costs, disclosed herein is a platform for developing conjugate vaccines, for example pneumococcal conjugate vaccines, using in vivo conjugation. This streamlined process has the potential to complement existing manufacturing pipelines or completely bypass the dependency on chemical conjugation methodologies, enabling the production of a more comprehensive conjugate vaccines.

Traditional, chemical conjugate vaccine synthesis is considered complex, costly, and laborious (Frasch, C. E. *Vaccine* 27, 6468-6470 (2009)) however, in vivo conjugation has been thoroughly progressing as a viable biosynthetic alternative (Huttner, A. et al. *Lancet Infect Dis* 17, 528-537 (2017)). These strides are best highlighted by the successes of GlycoVaxyn, (now LimmaTech Biologics AG an independent company with direct ties to GlaxoSmithKline), a clinical stage biopharmaceutical company with multiple bioconjugate vaccines in various phases of clinical trials, one of which (Flexyn2a) has just completed a Phase 2b challenge study. Although GlycoVaxyn has been at the forefront of the in vivo conjugation revolution, the ability to glycosylate carrier/acceptor proteins with polysaccharides containing glucose (Glc) as the reducing end sugar has been elusive and, expectedly, has stymied the development of a pneumococcal bioconjugate vaccine.

The oligosaccharyltransferase PglS—previously referred to as PglL by Schulz et al. (PMID23658772) and PglL$_{ComP}$ by Harding et al. 2015 (PMID 26727908)—was only recently characterized as a functional OTase (Schulz, B. L. et al. *PLoS One* 8, e62768 (2013)). Subsequent mass spectrometry studies on total glycopeptides demonstrated that PglS does not act as a general PglL-like OTase, glycosylating multiple periplasmic and outer membrane proteins (Harding, C. M. et al. *Mol Microbiol* 96, 1023-1041 (2015)). In fact, the genome of *A. baylyi* ADP1 encodes for two OTase, a PglL-like ortholog (UniProtKB/Swiss-Prot: Q6FFS6.1), which acts as the general OTase and PglS (UniProtKB/Swiss-Prot: Q6F7F9.1), which glycosylates a single protein, ComP (Harding, C. M. et al. *Mol Microbiol* 96, 1023-1041 (2015)).

ComP is orthologous to type IV pilin proteins, like PilA from *Pseudomonas aeruginosa* and PilE from *Neisseria meningitidis*, both of which are glycosylated by the OTases TfpO (Castric, P. *Microbiology* 141 (Pt 5), 1247-1254 (1995)) and PglL (Power, P. M. et al. *Mol Microbiol* 49, 833-847 (2003)), respectively. Although TfpO and PglL also glycosylate their cognate pilins at serine residues, the sites of glycosylation differ between each system. TfpO glycosylates its cognate pilin at a C-terminal serine residue (Comer, J. E., Marshall, M. A., Blanch, V. J., Deal, C. D. & Castric, P. *Infect Immun* 70, 2837-2845 (2002)), which is not present in ComP. PglL glycosylates PilE at an internal serine located at position 63 (Stimson, E. et al. *Mol Microbiol* 17, 1201-1214 (1995)). ComP also contains serine residues near position 63 and the surrounding residues show moderate conservation to PilE from *N. meningitidis*. Comprehensive glycopeptide analysis, however, revealed this serine and the surrounding residues were not the site of glycosylation in ComP. Here it is disclosed that PglS glycosylates ComP at a single serine residue located at position corresponding to the conserved serine at position 84 of ComP$_{ADP1}$: AAC4588631 (SEQ ID NO: 1) (also corresponding to the conserved serine at position 82 of ComP$_{110264}$: ENV58402.1 (SEQ ID NO: 2)), which is a novel glycosylation site not previously found within the type IV pilin superfamily. The ability of PglS to transfer polysaccharides containing glucose as the reducing end sugar coupled with the identification of a novel site of glycosylation within the pilin superfamilies demonstrates that PglS is a functionally distinct OTase from PglL and TfpO.

PglS, but not PglB or PglL, Transferred Polysaccharides Containing Glucose at their Reducing End to the Acceptor Protein ComP.

Two classes of OTases, PglB and PglL, have previously been employed for in vivo conjugation (Feldman, M. F. et al. *Proc Natl Acad Sci USA* 102, 3016-3021 (2005); Faridmoayer, A., Fentabil, M. A., Mills, D. C., Klassen, J. S. & Feldman, M. F. *J Bacteriol* 189, 8088-8098 (2007)). PglB, the first OTase described, preferentially transfers glycans containing an acetamido-group at the C-2 position of the reducing end (i.e. N-acetylglucosamine), as it is believed to play a role in substrate recognition (Wacker, M. et al. *Proc Natl Acad Sci USA* 103, 7088-7093 (2006)). However, polysaccharides with galactose (Gal) at the reducing end, such as the *S. enterica* Typhimurium O antigen, can be transferred by an engineered PglB variant (Ihssen, J. et al. *Open Biol* 5, 140227 (2015)). The second described OTase, PglL from *N. meningitidis*, has more relaxed substrate specificity than PglB, naturally transferring polysaccharides with an acetamido-group at the C-2 position as well as polysaccharides containing galactose (Gal) at the reducing end (Faridmoayer, A., Fentabil, M. A., Mills, D. C., Klassen, J. S. & Feldman, M. F. *J Bacteriol* 189, 8088-8098 (2007); Pan, C. et al. *MBio* 7 (2016)). However, there is no evidence available for PglB or PglL mediated transfer of polysaccharides containing glucose (Glc) at the reducing end, which is of particular interest given that the majority of pneumococcal CPSs contain glucose at the reducing end (Geno, K. A. et al. *Clin Microbiol Rev* 28, 871-899 (2015)). The ability of PglB and PglL to transfer the pneumococcal serotype 14 capsular polysaccharide (CPS14) to their cognate glycosylation targets, AcrA (Wacker, M. et al. *Science* 298, 1790-1793 (2002)) and DsbA (Vik, A. et al. *Proc Natl Acad Sci USA* 106, 4447-4452 (2009)), respectively, was tested. As seen in FIG. 1A and FIG. 1B, both acceptor proteins were expressed; however, no evidence for CPS14 glycosylation to either acceptor protein was observed.

Acinetobacter species have been describes as containing three O-linked OTases; a general PglL OTase responsible for glycosylating multiple proteins, and two pilin-specific OTases (Harding, C. M. *Mol Microbiol* 96, 1023-1041 (2015)). The first pilin-specific OTase is an ortholog of TfpO (also known as PilO) and is not employed for in vivo conjugation systems due to its inability to transfer polysaccharides with more than one repeating unit (Faridmoayer, A., Fentabil, M. A., Mills, D. C., Klassen J. S. & Feldman, M. F. *J Bacteriol* 189, 8088-8098 (2007)). The second pilin specific OTase, PglS glycosylates a single protein, the type IV pilin ComP[28]. A bioinformatic analysis indicated that PglS is the archetype of a distinct family of OTases. Given that PglS represents a new class of O-OTase, its ability to transfer pneumococcal CPS14 to its cognate acceptor protein, ComP (Harding, C. M. et al. *Mol Microbiol* 96, 1023-1041 (2015)) was tested. As seen in FIG. 1C, co-expression of the CPS14 biosynthetic locus in conjunction with PglS and a hexa-his tagged variant of ComP resulted in a typical ladder-like pattern of bands compatible with protein glycosylation when analyzed via western blotting (FIG. 1B). The higher molecular weight, modal distribution of signals is indicative of protein glycosylation with repeating glycan subunits of increasing molecular weight. Together, these results indicate that, unlike the previously characterized OTases, PglS is able to transfer polysaccharides with glucose at the reducing end.

Figure 2:
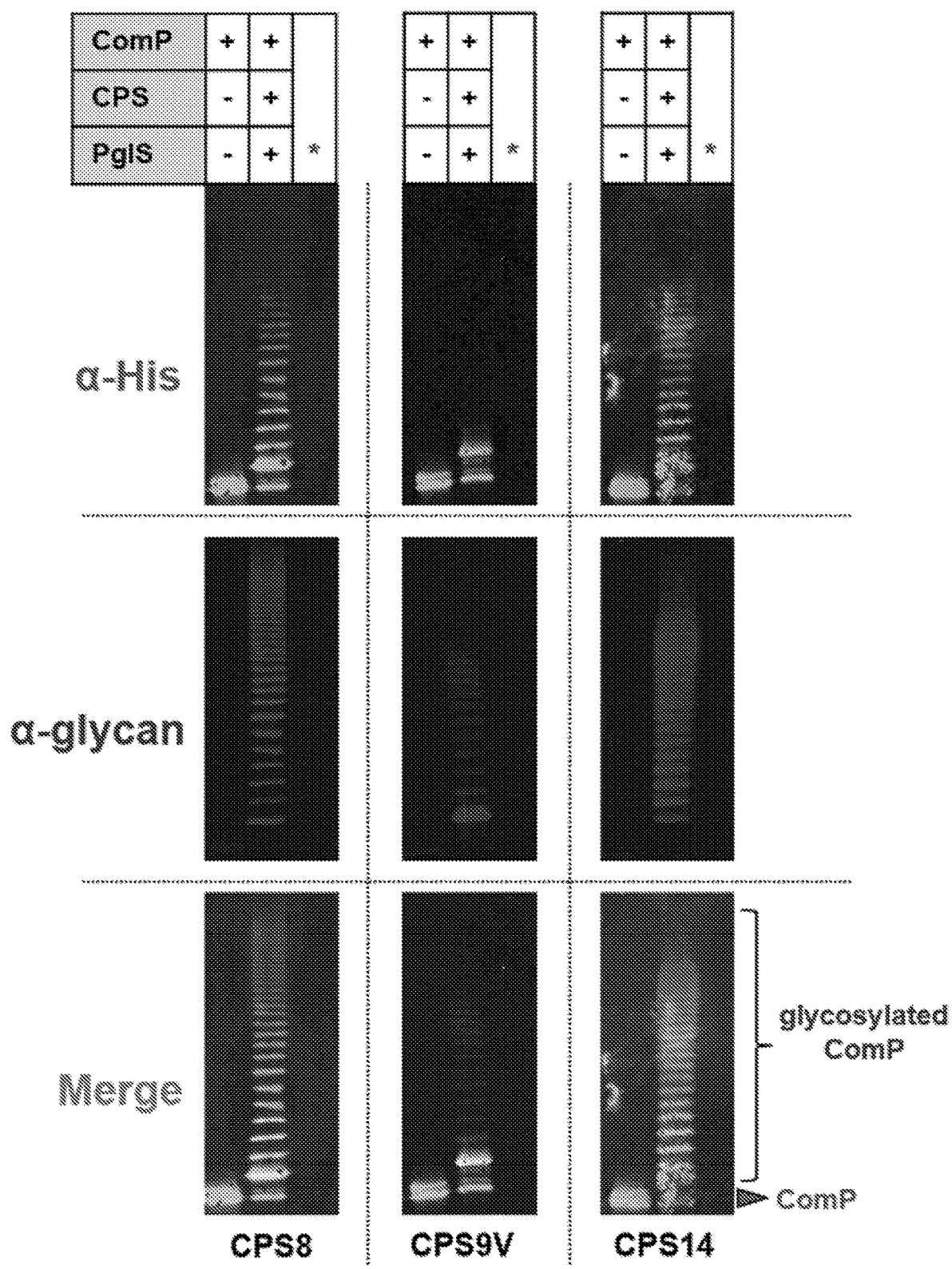
FIG. 2.

There are more than 90 serotypes of *S. pneumoniae* (Geno, K. A. et al. *Clin Microbiol Rev* 28, 871-899 (2015)). Many increasingly prevalent serotypes, like serotypes 8, 22F, and 33F are not included in currently licensed vaccines. Therefore, the versatility was tested of PglS to generate a multivalent pneumococcal bioconjugate vaccine against two serotypes included in Prevnar 13 (serotype 9V and 14) and one serotype not included (serotype 8) (Package Insert—Prevnar 13—FDA, on the world wide web at fda.gov/downloads/BiologicsBloodVaccinesNaccines/Approved-Products/UCM201669.pdf)). Importantly, all of three of these capsular polysaccharides contain glucose as the reducing end sugar (Geno, K. A. et al. *Clin Microbiol Rev* 28, 871-899 (2015)). As seen in FIG. 2, western blot analysis of affinity purified proteins from whole cells co-expressing PglS, a hexa-his tagger ComP variant, and either CPS8, CPS9V, or CPS14 resulted in the generation CPS-specific bioconjugates. Moreover, antisera specific to either the CPS8, CPS9V, or CPS14 antigens also reacted to the anti-His reactive bands, indicating that ComP-His was glycosylated with the correct polysaccharides. To confirm that the material purified was not contaminated with lipid-linked polysaccharides, the samples were treated with proteinase K and observed a loss of signal when analyzed via western blotting, confirming that the bioconjugates were proteinaceous.

Therefore, it was demonstrated that PglS can transfer *S. pneumoniae* polysaccharides to ComP, wherein PglB and PglL could not. Specifically, PglS is the only OTase in the known universe capable of transferring polysaccharides with glucose at the reducing end. In certain aspects, PglS can be used to transfer any lipid-linked oligosaccharide or polysaccharide (collectively referred to herein as "oligo- or polysaccharide") containing glucose at the reducing end to ComP or a fusion protein containing a fragment of ComP.

PglS can Transfer Capsular Polysaccharides of *Klebsiella* to ComP.

*Klebsiella pneumonia* (*K. pneumoniae*), a Gram negative opportunistic human pathogen, produces a capsular polysaccharide known to be important for virulence. To date at least 79 antigenically distinct capsular polysaccharides have been described for *Klebsiella* species (Pan, Y. J. et al. *Sci Rep* 5, 15573 (2015)). Furthermore, *K. pneumoniae* is known to produce at least 59 of the 77 capsular polysaccharides, more than half of which contain glucose as the reducing end sugar (Pan, Y. J. et al. *Sci Rep* 5, 15573 (2015)). To determine if PglS could transfer *K. pneumoniae* capsular polysaccharides to ComP, the genes encoding for the proteins required for the synthesis of either the K1 or the K2 capsular polysaccharides were cloned into the IPTG inducible pBBR1MCS-2 vector (Kovach, M. E. et al. *Gene* 166, 175-176 (1995)). The K1 capsule gene locus was cloned from *K. pneumoniae* NTUH K-2044, a previously characterized K1 capsule producing strain (Wu, K. M. et al. *J Bacteriol* 191, 4492-4501 (2009)). The K2 capsule gene locus was cloned from *K. pneumoniae* 52.145, a previously characterized K2 capsule producing strain (Lery, L. M. et al. *BMC Biol* 12, 41 (2014)). The K1 or the K2 capsular polysaccharide expressing plasmids were then individually introduced into *E. coli* co-expressing PglS OTase and the acceptor protein ComP from a separate plasmid vector. To enhance expression of K1 and K2 specific polysaccharides, the *K. pneumoniae* transcriptional activator rmpA from *K. pneumoniae* NTUH K-2044 was subsequently cloned into pACT3 (Dykxhoorn, D. M., St Pierre, R. & Linn, T. *Gene* 177, 133-136 (1996)), a low copy, IPTG inducible vector as it has previously been characterized as a regulator of capsule in *K. pneumoniae* (Arakawa, Y. et al. *Infect Immun* 59, 2043-2050 (1991)); Yeh, K. M. et al. *J Clin Microbiol* 45, 466-471 (2007)). Introduction of the rmpA gene into *E. coli* strains co-expressing PglS and hexa-his tagged ComP variant and either the K1 or K2 capsular polysaccharides from *K. pneumoniae*, resulted robust expression and detection of higher molecular ComP bioconjugates as indicated by the typical ladder-like pattern of bands compatible with protein glycosylation when analyzed via western blotting (FIG. 3B). The modal distribution of signals is indicative of protein glycosylation with repeating glycan subunits of increasing molecular weight. Thus collectively, PglS was able to glycosylate ComP with the K1 and K2 capsular polysaccharides from *K. pneumonia*. Increased efficiency of conjugation was observed with co-expression of the transcriptional activator rmpA from *K. pneumoniae*.

PglS can transfer *K. pneumoniae* polysaccharides to ComP. Given that most *K. pneumoniae* capsular polysaccharides contain glucose as the reducing end sugar, the only other commercially licensed OTases (PglB and PglL) should be unable to generate conjugate vaccines using these polysaccharides. Moreover, co-expression of the transcriptional activator, RmpA, with the capsule gene cluster enhanced capsule expression to detectably levels. In certain aspects, the method for producing *Klebsiella* conjugates can be used to generate a pan *Klebsiella* conjugate vaccine encompassing all serotypes—including other species such as *K. varricola*, *K. michiganensis*, and *K. oxytoca*.

Figure 4A:
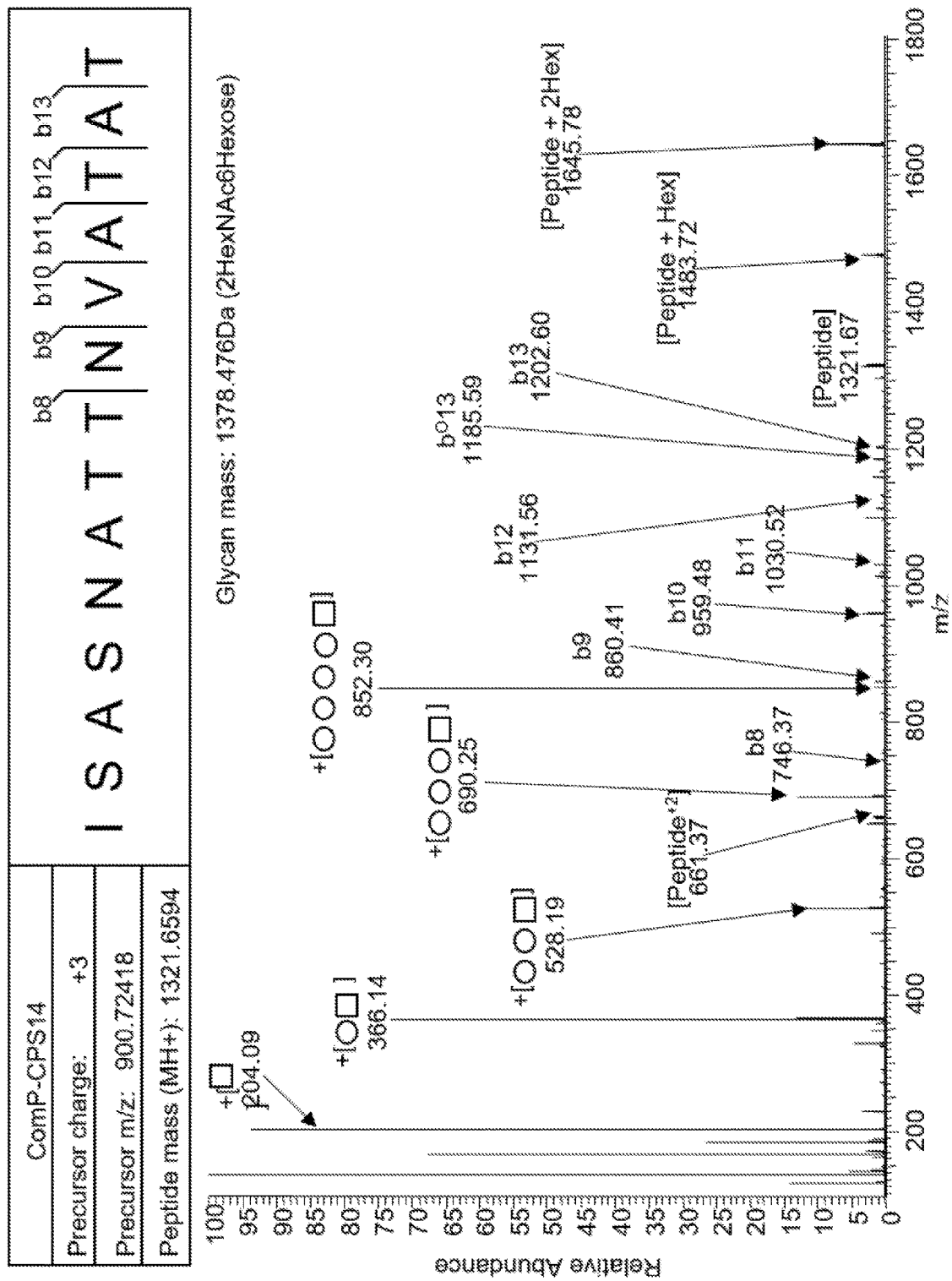
FIG. 4A.
Figure 4B:
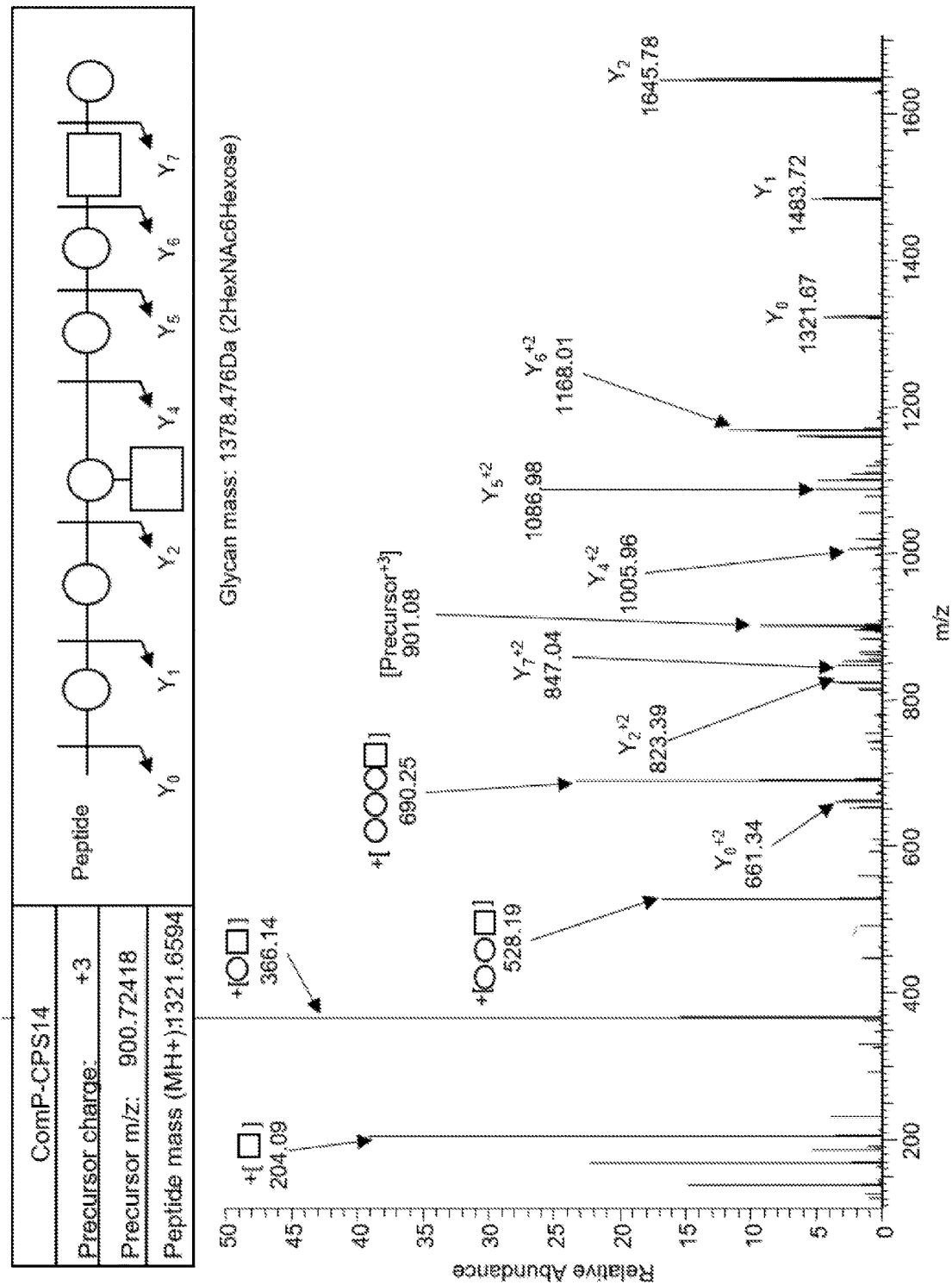
FIG. 4B.
Figure 16:
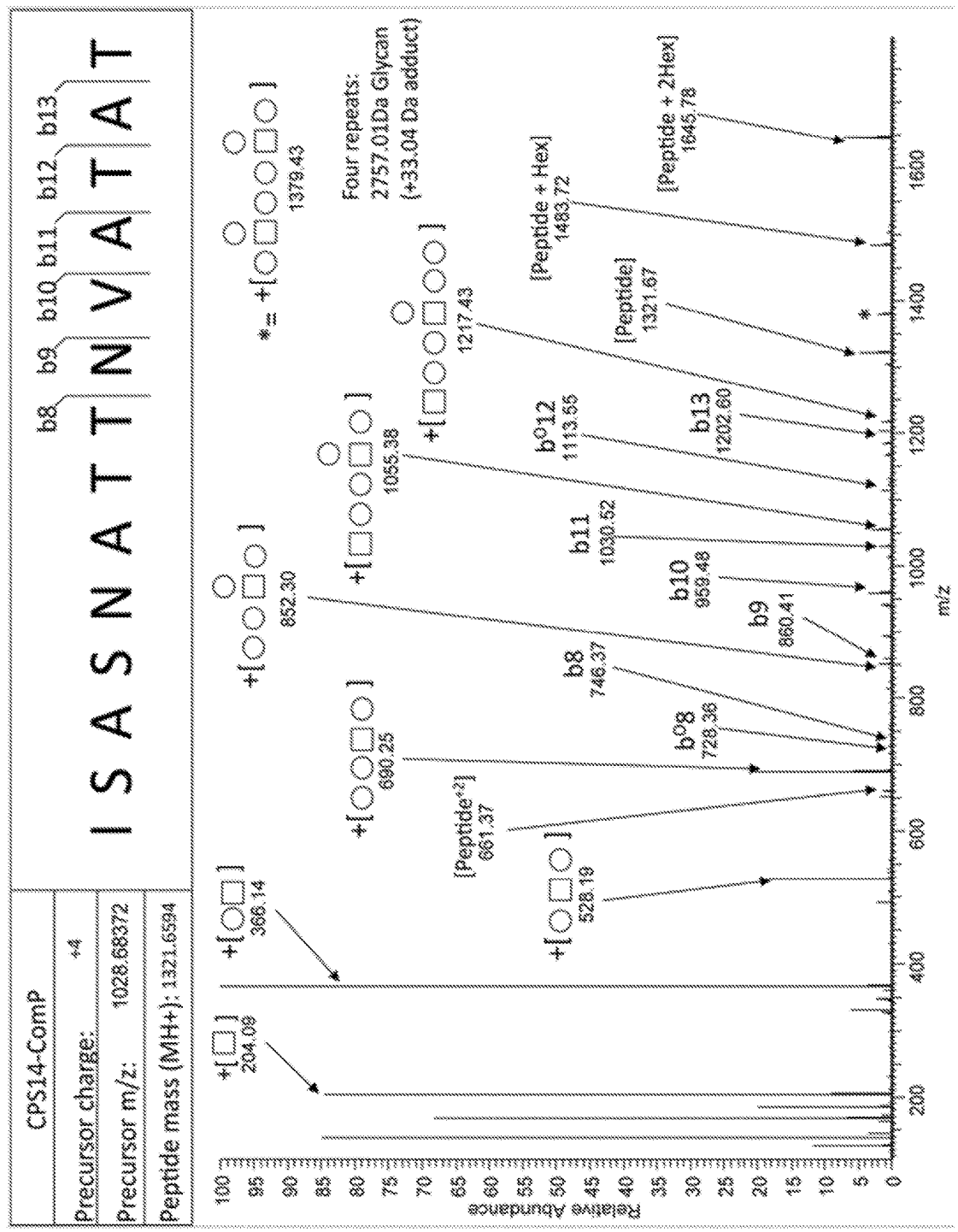
FIG. 16.

Mass spectrometry and site directed mutagenesis confirm PglS is an O-linked OTase and reveal that ComP is glycosylated at a serine residue corresponding to position 84 of ComP$_{ADP1}$. N-glycosylation in bacteria generally occurs within the sequon D-X-N-S-T (SEQ ID NO: 21), where X is any amino acid but proline (Kowarik, M. et al. *EMBO J* 25, 1957-1966 (2006)). On the contrary, O-glycosylation does not seem to follow a defined sequon. Most O-glycosylation events in bacterial proteins occur in regions of low complexity (LCR), rich in serine, alanine, and proline (Vik, A. et al. *Proc Natl Acad Sci USA* 106, 4447-4452 (2009)). Alternatively, some pilins are O-glycosylated at a C-terminal serine residue (Comer, J. E., Marshall, M. A., Blanch, V. J., Deal, C. D. & Castric, P. *Infect Immun* 70, 2837-2845 (2002)). ComP does not appear to have an obvious LCR or a C-terminal serine residue homologous to those found in other pilin like proteins and therefore mass spectrometry was employed to determine the site(s) of glycosylation. Purified CPS14-ComP bioconjugates were subjected to proteolytic digestion, ZIC-HILIC glycopeptide enrichment, and multiple MS analyses. As seen in FIG. 4A and FIG. 4B, a single glycopeptide consisting of the peptide ISASNATTN-VATAT (SEQ ID NO: 22) was identified attached to a glycan that matched the published CPS14 composition (Geno, K. A. et al. *Clin Microbiol Rev* 28, 871-899 (2015)). To enable confirmation of both the peptide and attached glycan sequences, multiple collision energies regimes were performed to confirm the glycosylation of the semi-GluC derived peptide ISASNATTNVATAT (SEQ ID NO: 22) with a 1378.47 Da glycan corresponding to HexNA$_{C2}$Hexose$_6$ (FIG. 4B). Additional glycopeptides were also observed decorated with extended glycans corresponding to up to four tetrasaccharide repeat units (FIG. 16).

Figure 5:
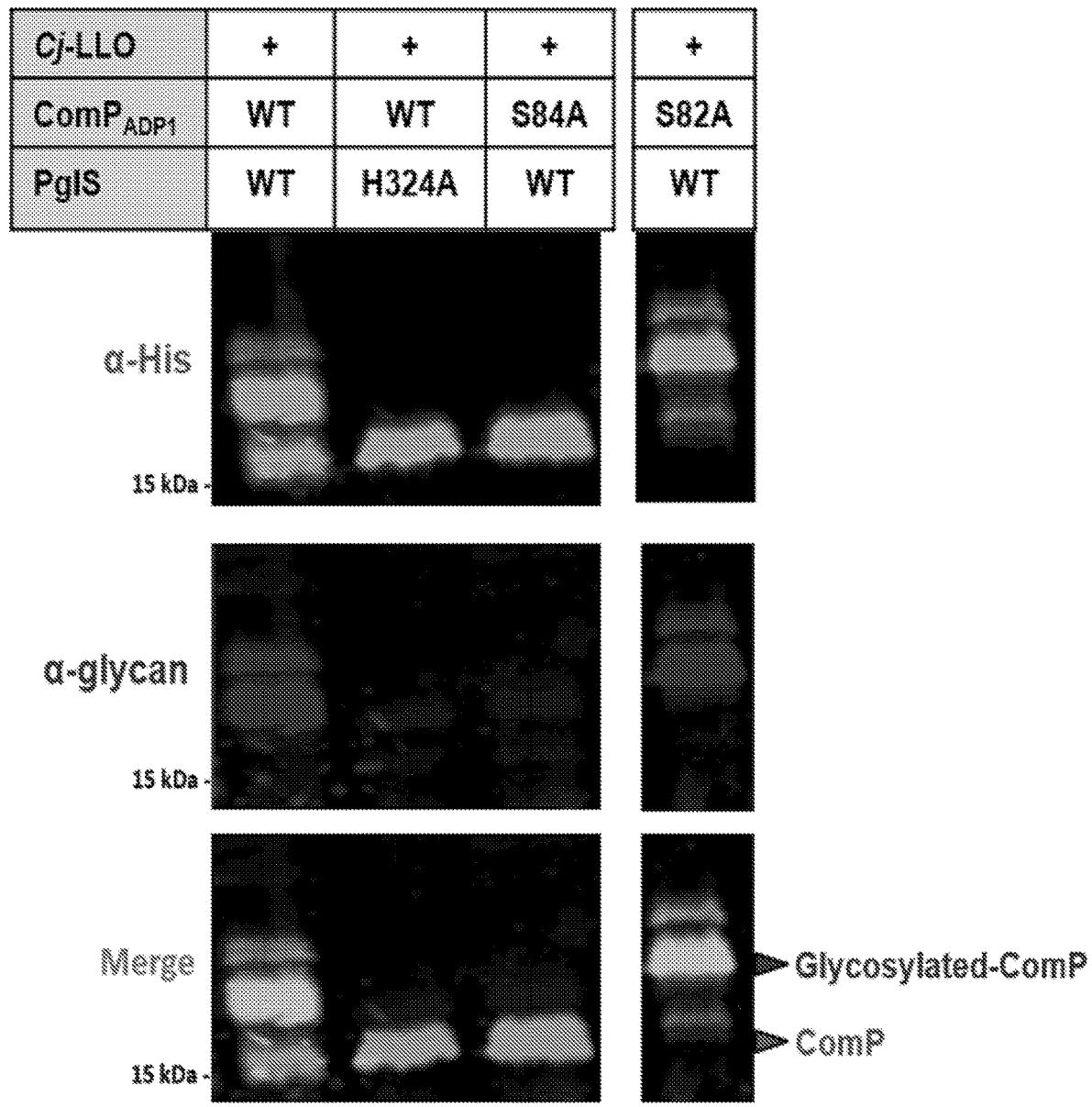
FIG. 5.
Figure 17:
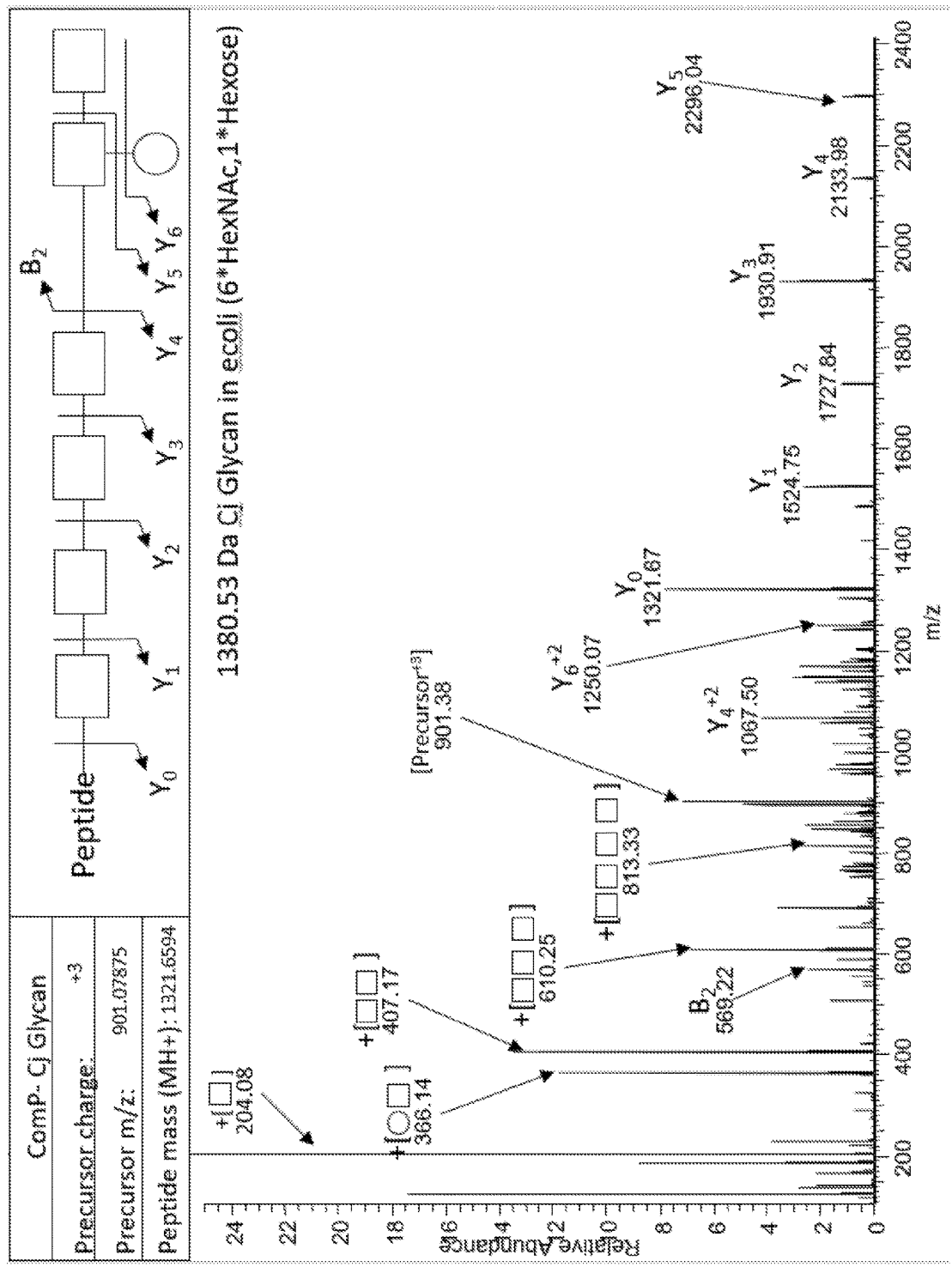
FIG. 17.
Figure 18:
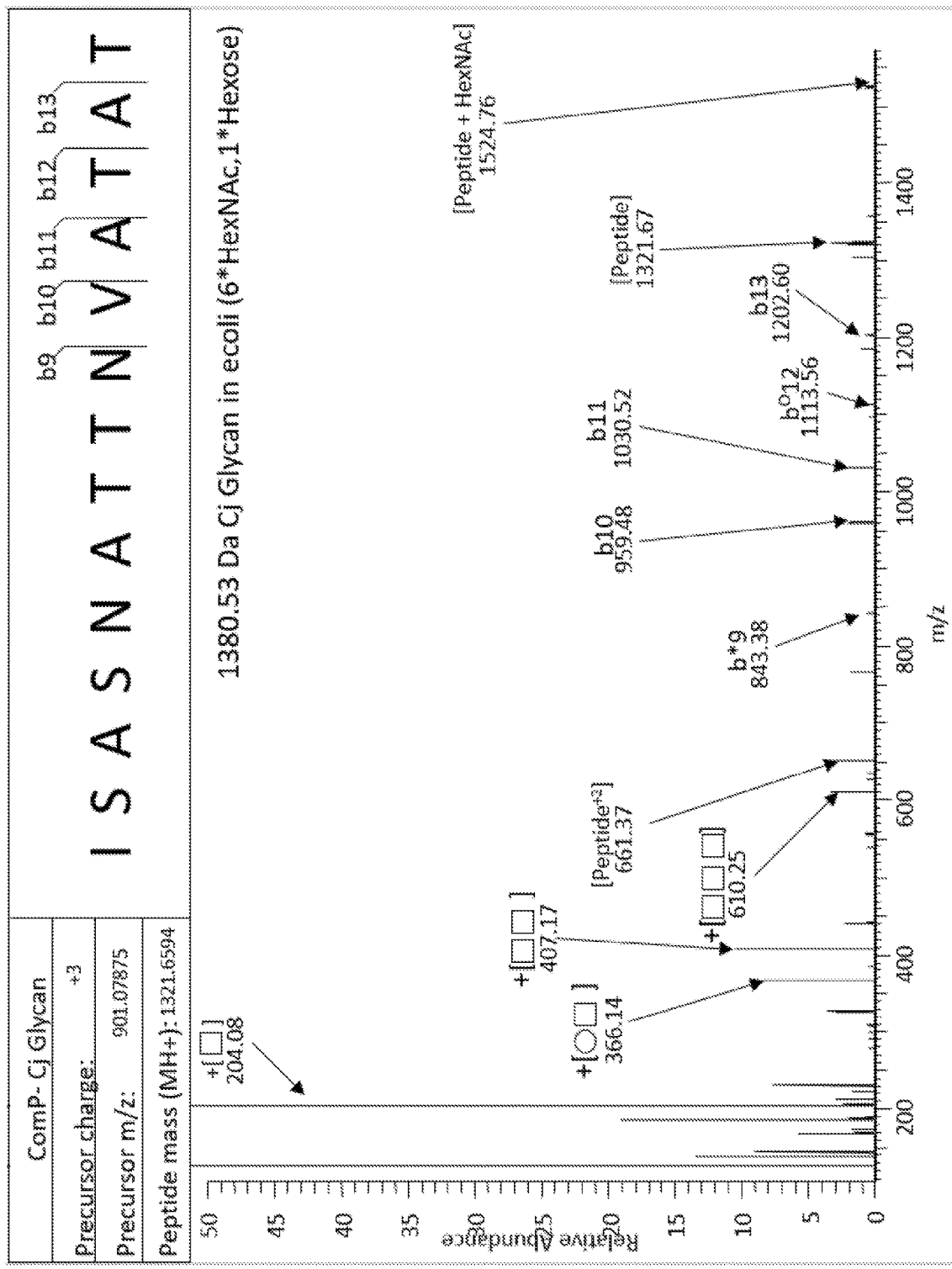
FIG. 18.
Figure 20A:
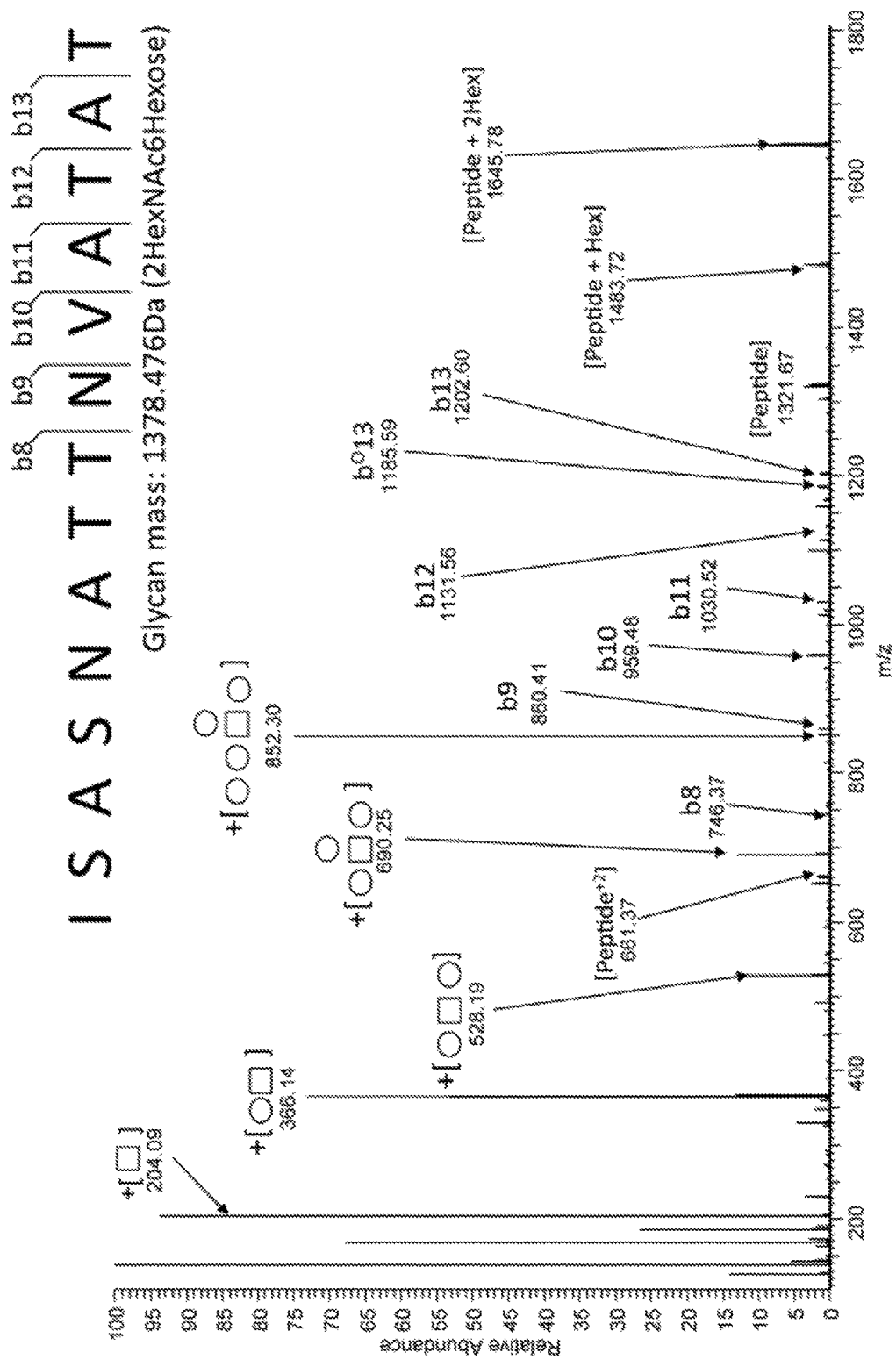
FIG. 20A,B.
Figure 20B:
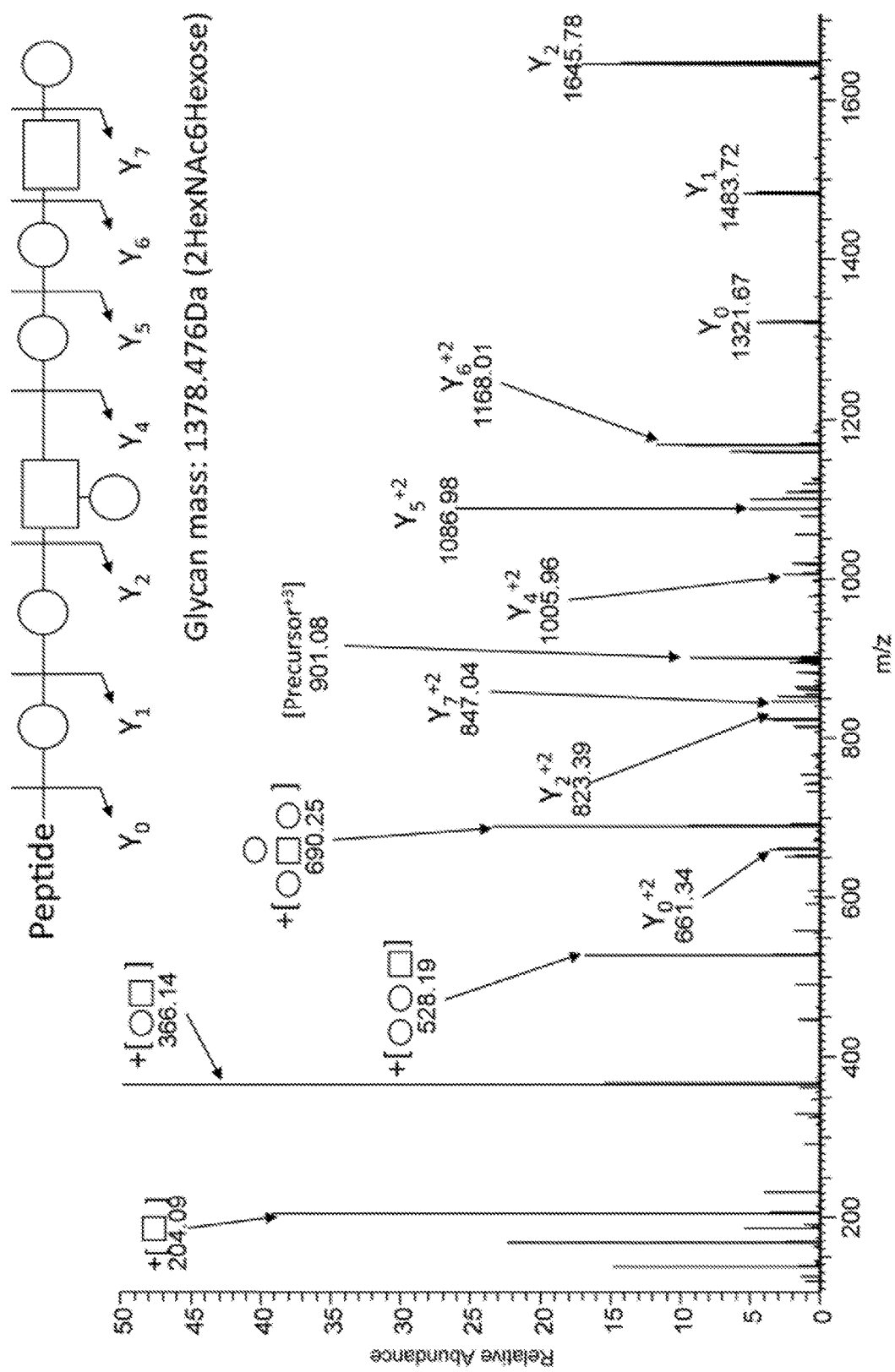
Figure 24C:
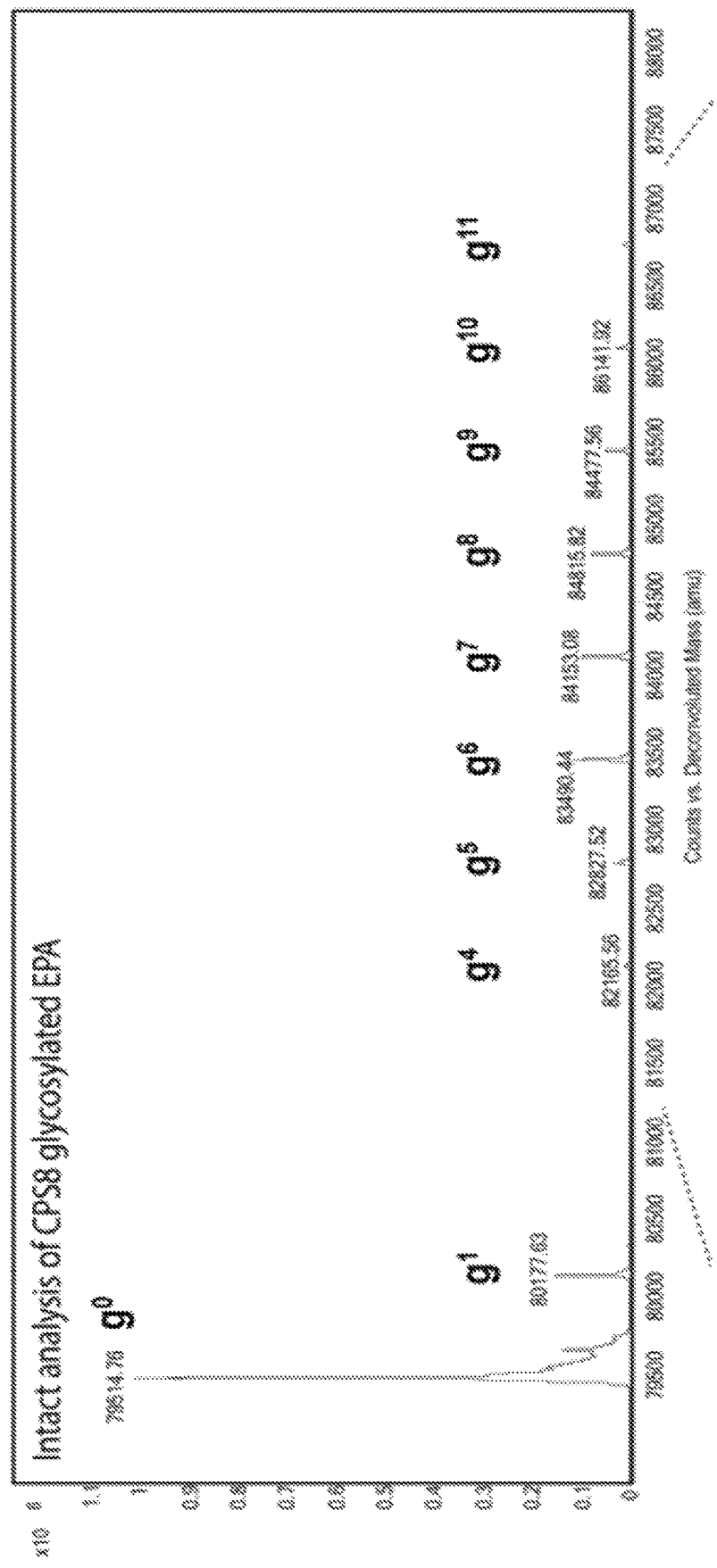
FIG. 24C.
Figure 24D:
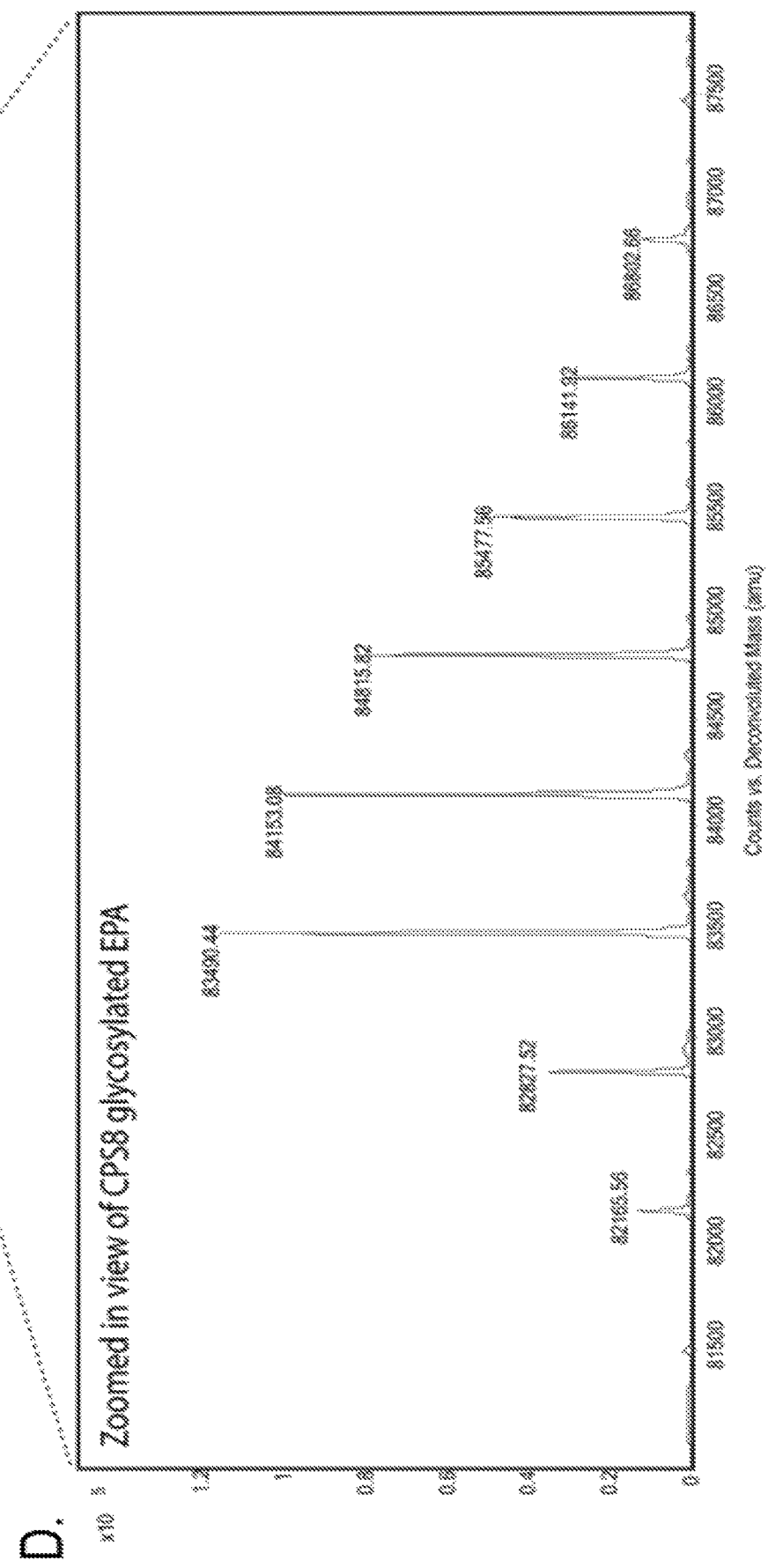
FIG. 24D.

It was previously shown that *Acinetobacter* species predominantly glycosylate proteins at serine residues and thus it was hypothesized that either serine (S) 82 or 84—as numbered in SEQ ID NO: 1—was the site of glycosylation (Scott, N. E. et al. *Mol Cell Proteomics* 13, 2354-2370 (2014)). To determine which serine residue was the site of glycosylation, these serine residues were individually mutated to alanine (A) and the glycosylation status of both mutant proteins was analyzed. For this experiment, the biosynthetic locus for the *C. jejuni* heptasaccharide was employed as the donor glycan, as glycosylation is readily detectable with the hR6 anti-glycan antisera as well as by an increase in electrophoretic mobility (Schwarz, F. et al. *Nat Chem Biol* 6, 264-266 (2010)). As shown in FIG. 5, wild type hexa-his tagged ComP was glycosylated with the *C. jejuni* heptasaccharide as indicated by its increased electrophoretic mobility and co-localization with hR6 antisera signal when co-expressed with PglS. MS analysis also confirmed the presence of the *C. jejuni* heptasaccharide on the identical semi-GluC derived peptide ISASNATTN-VATAT (SEQ ID NO: 22) modified by CPS14 (FIG. 17 and FIG. 18). As a negative control, a catalytically inactive PglS mutant (H324A) was generated, that when co-expressed with the *C. jejuni* heptasaccharide glycan was unable to glycosylate wild type ComP. Site directed mutagenesis was performed and it was observed that glycosylation of ComP with the *C. jejuni* heptasaccharide was abolished in the ComP[S84A] mutant, whereas ComP[S82A] was glycosylated at wild-type levels. Together, these results indicate that ComP is singly glycosylated at serine 84 (as numbered in SEQ ID NO: 1) by PglS, which is a unique site that is different than other previously characterized pilin like proteins. This corresponds to serine 82 as numbered in SEQ ID NO: 2.

Bioinformatic Features of ComP Pilin Orthologs.

ComP was first described as a factor required for natural transformation in *Acinetobacter* baylyi ADP1 (Porstendorfer, D., Drotschmann, U. & Averhoff, B. *Appl Environ Microbiol* 63, 4150-4157 (1997)). In a subsequent study, it was demonstrated that ComP from *A. baylyi* ADP1 (herein referred to as ComP$_{ADP1}$) was glycosylated by a novel OTase, PglS, located immediately downstream of ComP, and not the general OTase PglL located elsewhere on the chromosome (Harding, C. M. et al. *Mol Microbiol* 96, 1023-1041 (2015)). The ComP$_{ADP1}$ protein (NCBI identifier AAC45886.1) belongs to a family of proteins called type IV pilins. Specifically, ComP shares homology to type IVa major pilins (Giltner, C. L., Nguyen, Y. & Burrows, L. L. *Microbiol Mol Biol Rev* 76, 740-772 (2012)). Type IVa pilins share high sequence homology at their N-terminus, which encode for the highly conserved leader sequence and N-terminal alpha helix; however, the C-terminus display remarkable divergences across genera and even within species (Giltner, C. L., Nguyen, Y. & Burrows, L. L. *Microbiol Mol Biol Rev* 76, 740-772 (2012)). To help differentiate ComP orthologs from other type IVa pilin proteins, such as, PilA from *A. baumannii*, *P. aeruginosa*, and *Haemophilus influenzae* as well as PilE from *Neisseria* species (Pelicic, V. *Mol Microbiol* 68, 827-837 (2008)), a BLASTp analysis was performed comparing the primary amino acid sequence of ComP$_{ADP1}$ against all proteins from bacteria in the *Acinetobacter* genus. Expectedly, many *Acinetobacter* type IVa pilin orthologs, including ComP$_{ADP1}$, share high homology at their N-termini; however, very few proteins display high sequence conservation across the entire amino acid sequence of ComP. At least six ComP orthologs (FIG. 6) were identified based on the presence of the conserved serine at position 84 relative to ComP$_{ADP1}$ as well as a conserved disulfide bond flanking the site of predicted glycosylation connecting the predicted alpha beta loop to the beta strand region (Giltner, C. L., Nguyen, Y. & Burrows, L. L. *Microbiol Mol Biol Rev* 76, 740-772 (2012)). Furthermore, all six ComP orthologs carry both a pglS homolog immediately downstream of the comP gene as well as a pglL homolog located elsewhere in the chromosome. Together, at least the presence of the conserved serine at position 84, the disulfide loop flanking the site of glycosylation, the presence of a pglS gene immediately downstream of comP, and the presence of a pglL homolog located elsewhere on the chromosome differentiate ComP pilin variants from other type IVa pilin variants.

Therefore, features common to ComP proteins are disclosed herein that identify ComP orthologs in different *Acinetobacter* species. ComP proteins can be differentiated from other pilins by the presence of the conserved glycosylated serine located at position 84 relative to the ADP1 ComP protein and the presence of a disulfide loop flanking the site of glycosylation. In addition, the presence of a pglS homolog immediately downstream of ComP is an indicator of ComP. Further to be classified as a PglS OTase protein rather than a PglL OTase protein, the OTase downstream of ComP must display higher sequence conservation with PglS (ACIAD3337) when compared to PglL (ACIAD0103) in *A. baylyi* ADP1.

In certain aspects disclosed herein, a ComP protein comprises an amino acid sequence that is at least 50%, 60%, 70%, 75%, 80%, 85%, 90%, 95%, 96%, 97%, 98%, 99%, or 100% identical to SEQ ID NO: 1 (ComP$_{ADP1}$: AAC45886.1), SEQ ID NO: 2 (ComP$_{110264}$: ENV58402.1), SEQ ID NO: 3 (ComP$_{GFJ-2}$: APV36638.1), SEQ ID NO: 4 (Com$_{P50v1}$: PKD82822.1), SEQ ID NO: 5 (ComP$_{4466}$: SNX44537.1), or SEQ ID NO: 6 (ComP$_{SFC}$: OAL75955.1), and contains a serine residue corresponding to the conserved serine residue at position 84 of SEQ ID NO: 1 (ComPADP1: AAC45886.1). In certain aspects disclosed herein, a ComP protein comprises an amino acid sequence that is at least 50%, 60%, 70%, 75%, 80%, 85%, 90%, 95%, 96%, 97%, 98%, 99%, or 100% identical to SEQ ID NO: 1 (ComPADP1: AAC45886.1), and contains a serine residue corresponding to the conserved serine residue at position 84 of SEQ ID NO: 1 (ComPADP1: AAC45886.1). In certain of these aspects, the ComP protein comprises a region corresponding to the region of SEQ ID NO: 2 (ComP110264: ENV58402.1) comprising the serine residue at position 82 of SEQ ID NO: 2 (ComP110264: ENV58402.1) flanked by a disulfide bond connecting the alpha beta loop to the beta strand region. In certain aspects, the ComP protein comprises the consensus sequence of SEQ ID NO: 37, SEQ ID NO: 38, or SEQ ID NO: 45 (Table 3 below). In certain aspects, the ComP protein comprises a region having the amino acid sequence of ADP1 VGVQEISASNATTNVATAT (SEQ ID NO: 39), 110264 TGVTQIASGASAATTN-VASAQ (SEQ ID NO: 40), GFJ-2 VGVQEINASSSTSN-VATAT (SEQ ID NO: 41), SFC AGVETIGASNKTKNVE-SAA (SEQ ID NO: 42), P50v1 VGVQTIAASNATKNVATAT (SEQ ID NO: 43), and 4466 NGVISASATTNVASSA (SEQ ID NO: 44), or variant of SEQ ID NO: 39, 40, 41, 42, 43, or 44 having one, two, three, four, five, six, or seven amino acid substitutions, additions, and/or deletions, wherein the variant sequence maintains the serine residue corresponding to the conserved serine residue at position 84 of SEQ ID NO: 1 (ComPADP1: AAC45886.1). In certain aspects, amino acid substitutions are conservative amino acid substitutions. It is also evident to one of ordinary skill in the art that in any aspect disclosed herein, the ComP protein is capable of being glycosylated on the serine residue corresponding to the conserved serine residue at position 84 of SEQ ID NO: 1 (ComP$_{ADP1}$: AAC45886.1).

ComP from *A. soli* CIP 110264 is Glycosylated by PglS from *A. baylyi* ADP1.

Figure 7:
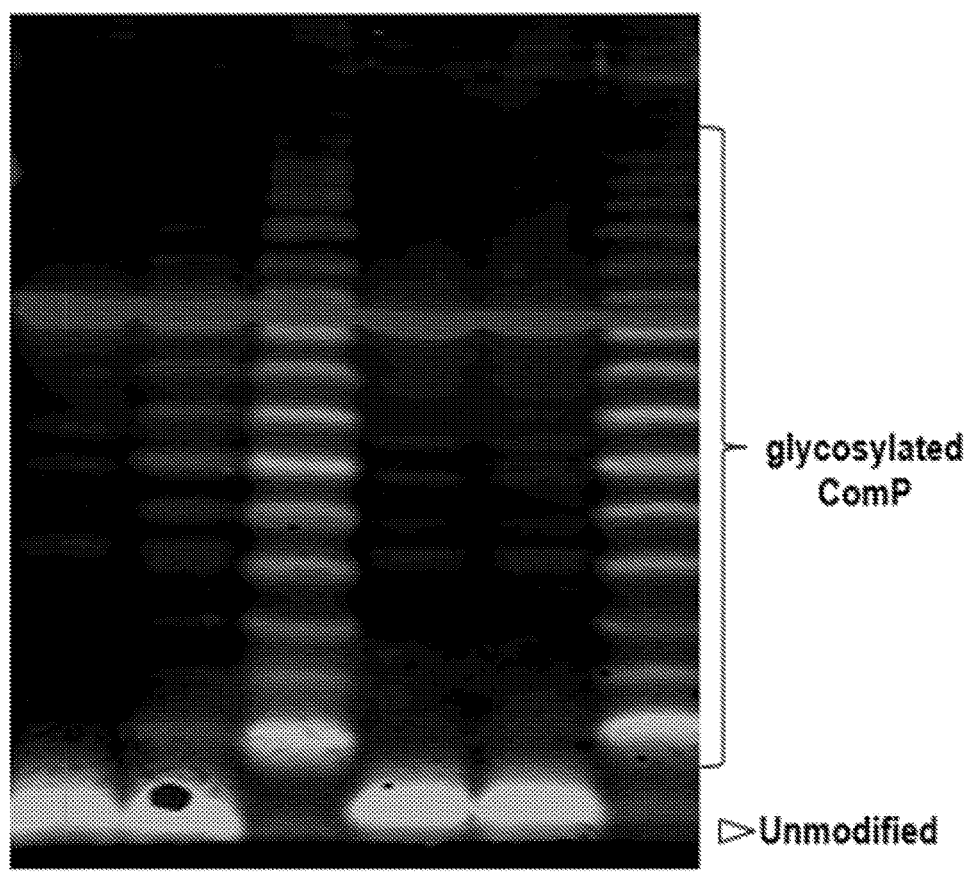
FIG. 7.

Given the presence of multiple ComP orthologs, whether PglS from *A. baylyi* ADP1 was able to glycosylate a divergent ComP protein was investigated. The ComP protein from *A. soli* CIP 110264 (ComP$_{110264}$) is 71% identical at the amino acid level when compared to the ComP$_{ADP1}$. However, consistent with the features above, ComP$_{110264}$ contains the predicted disulfide bridge between the predicted alpha-beta loop and the second beta strand as well as the conserved serine located at position 84 relative to ComP$_{ADP1}$. Moreover, a PglS ortholog can be found immediately downstream of ComP$_{110264}$. To determine whether PglS from *A. baylyi* ADP1 (PglS$_{ADP1}$) could glycosylate ComP$_{110264}$, PglS$_{ADP1}$ was cloned into pACT3 and ComP$_{110264}$ into pEXT20 (Dykxhoorn, D. M., St Pierre, R. & Linn, T. *Gene* 177, 133-136 (1996)) and these plasmids were introduced into *E. coli* expressing the serotype 8 capsular polysaccharide (CPS8) from *S. pneumoniae*. Further, the converse experiment was performed by cloning and expressing PglS from *A. soli* CIP 110264 (PglS$_{110264}$) with ComP$_{ADP1}$. As seen in FIG. 7, PglS$_{110264}$ minimally glycosylated its cognate acceptor pilin ComP$_{110264}$ as indicated by higher molecular weight ComP pilin variants when compared to whole cell lysates lacking PglS$_{110264}$. Based on western blot analysis, PglS$_{110264}$ appears to not glycosylate ComP$_{ADP1}$. On the other hand, PglS$_{ADP1}$ efficiently glycosylated both ComP$_{ADP1}$ and ComP$_{110264}$ as indicated by the robust increase of His-reactive signals of increasing electrophoretic mobility. Collectively, PglS$_{ADP1}$ appears to be an optimal OTase from heterologous glycosylation in *E. coli* with a unique ability to cross glycosylate multiple ComP substrates. Thus it was demonstrated that PglS proteins from different *Acinetobacter* species can glycosylate divergent, non-native ComP sequences.

Generation of a Soluble, Periplasmic Fusion Protein Capable of being Glycosylated by PglS.

Figure 8:
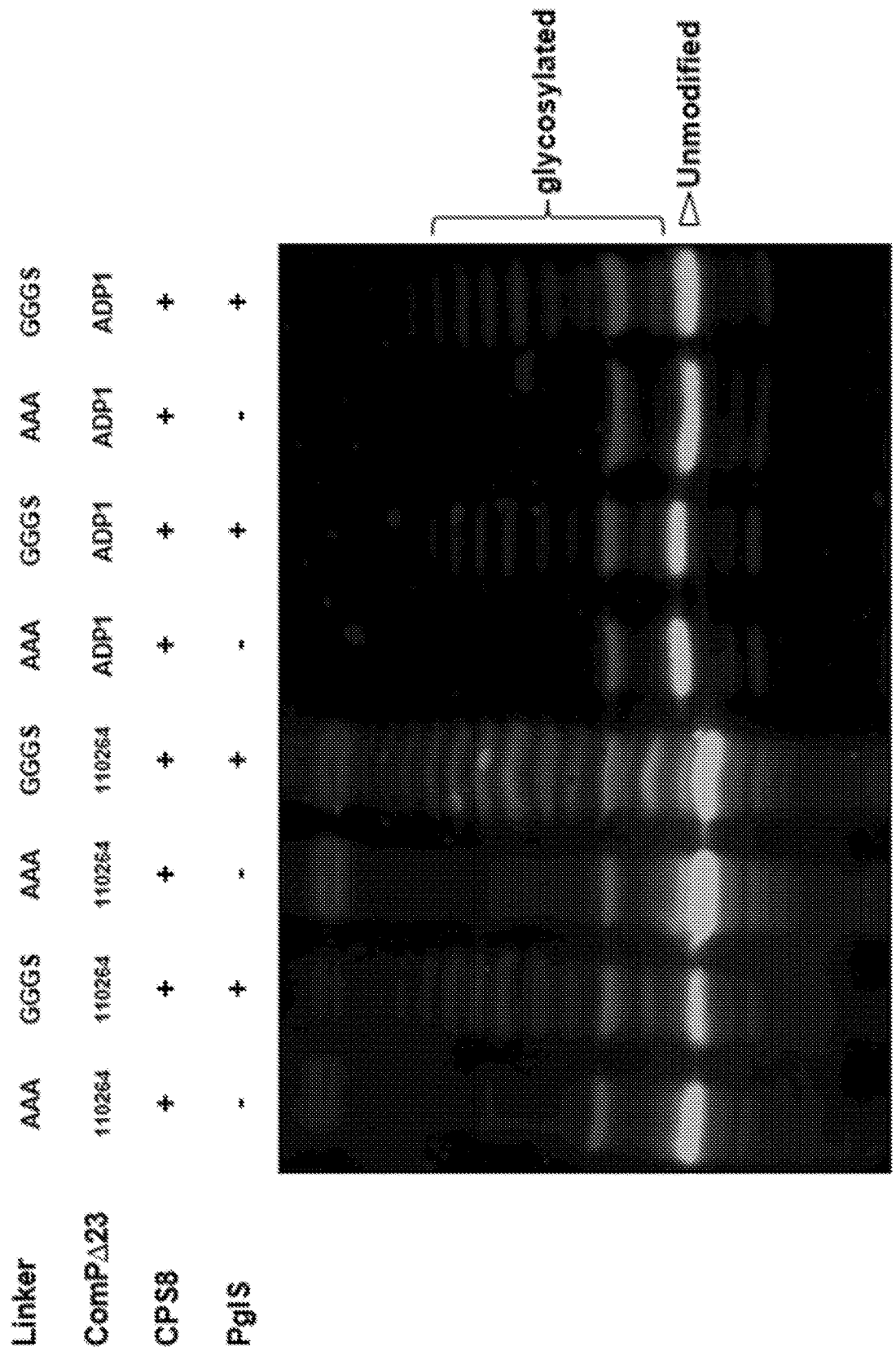
FIG. 8.
Figure 9:
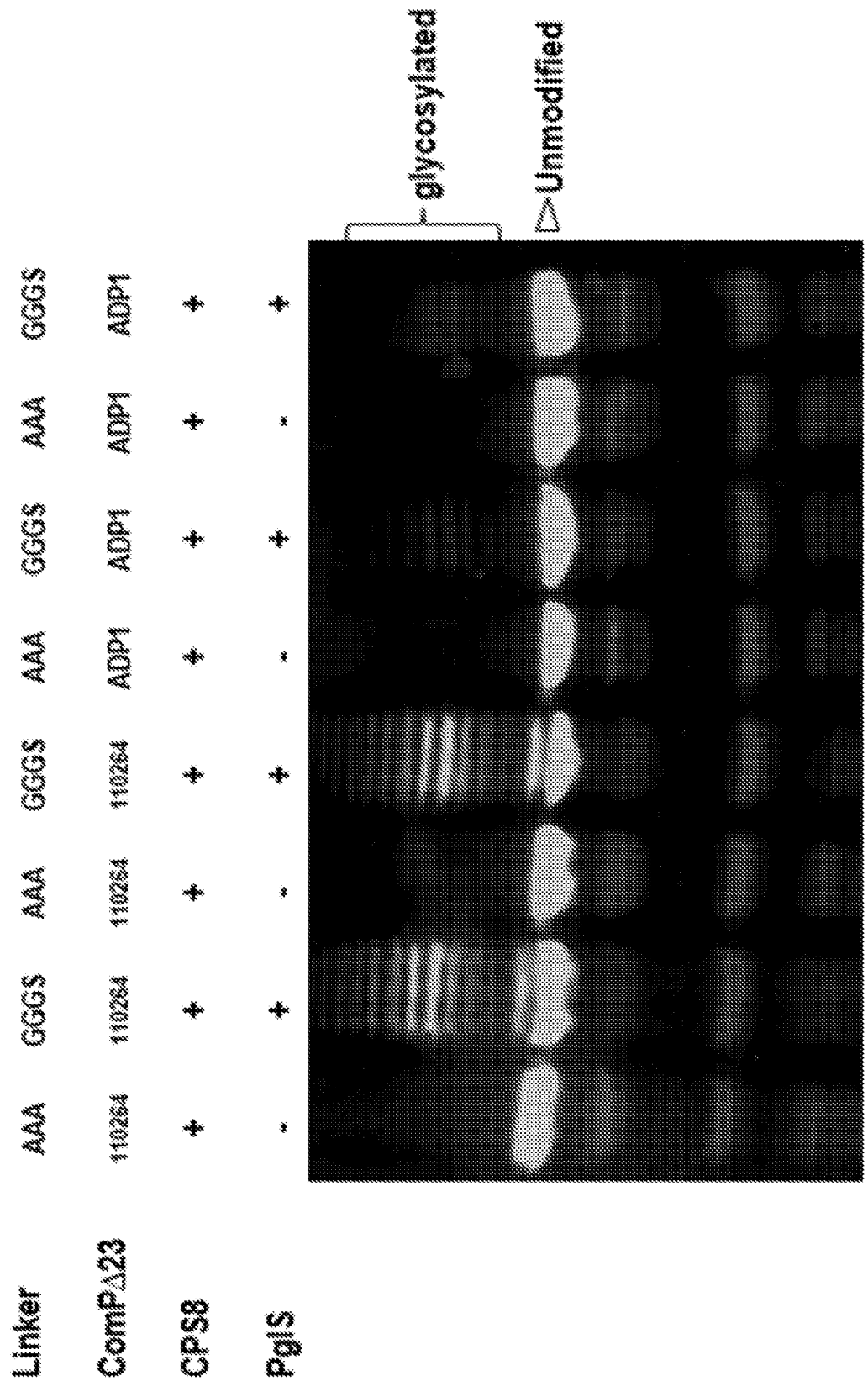
FIG. 9.
Figure 10:
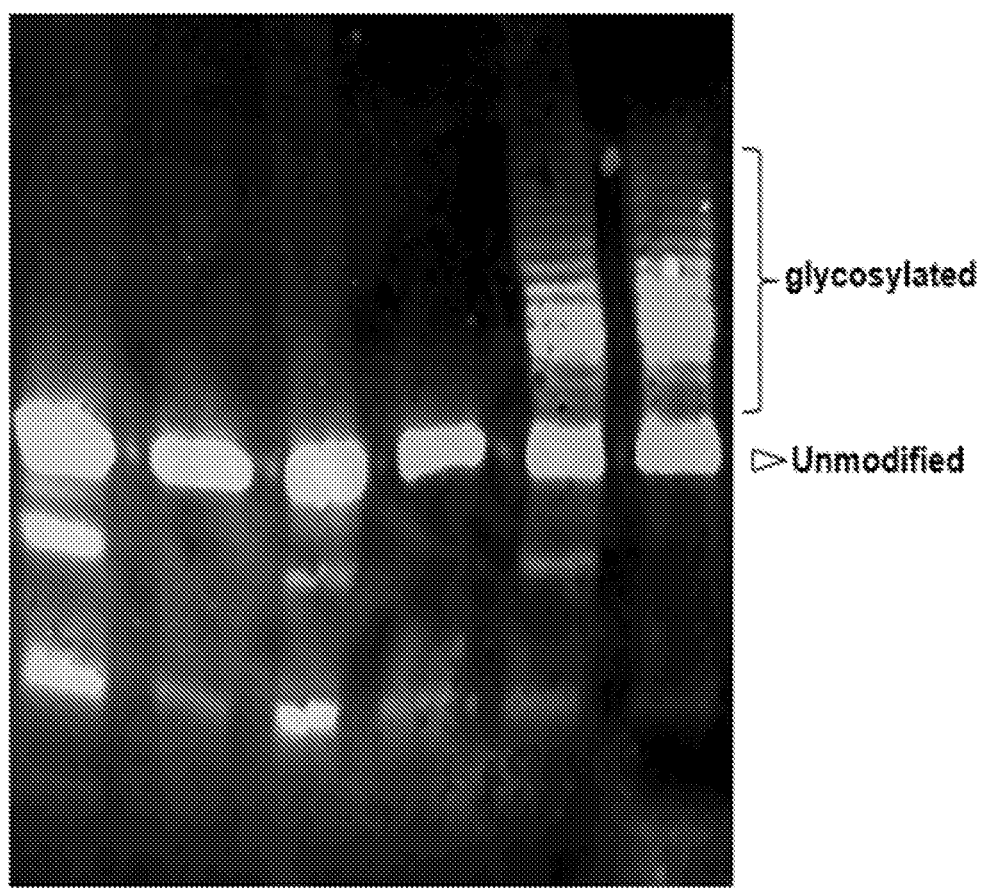
FIG. 10.

All members of type IVa pilin family are considered membrane proteins as part of their N-terminal alpha helix is embedded within the inner membrane (Giltner, C. L., Nguyen, Y. & Burrows, L. L. *Microbiol Mol Biol Rev* 76, 740-772 (2012)). Therefore, in order to generate soluble variants of ComP that are able to be glycosylated by PglS, translational fusions were constructed of truncated ComP fragment proteins onto three different carrier proteins. The carrier proteins, DsbA and MalE (also known as maltose binding protein—MBP) from *E. coli*, were selected as suitable carriers as both have been previously shown to facilitate periplasmic localization and solubility of acceptor proteins fused at their C-termini (Malik, A. *Biotech* 6, 44 (2016)). Exotoxin A from *Pseudomonas aeruginosa* (EPA) was also selected as it has been previously shown to act as an immunogenic carrier protein in other conjugate vaccine formulations (Ravenscroft, N. et al. *Glycobiology* 26, 51-62 (2016)). Fusion proteins consisted of a leader sequence, carrier protein, a short linker peptide, a ComP variant without the first 28 amino acids, and a hexa-histidine tag. The first 28 amino acids of ComP$_{ADP1}$ and ComP$_{110264}$ were removed as these amino acids contain the leader sequence as well as the hydrophobic region of the N-terminal alpha helix predicted to be embedded into the inner membrane. Fusion constructs were then introduced into *E. coli* expressing the pneumococcal serotype 8 capsular polysaccharide (CPS8) and either pACT3 alone or pACT3 carrying pglS$_{110264}$ or pglS$_{ADP1}$. As seen in FIG. 8, *E. coli* cells expressing either DsbA-AAA-ComPΔ28$_{110264}$ or DsbA-GGGS-ComPΔ28$_{110264}$ in combination with PglS$_{ADP1}$ demonstrated detectable levels of glycosylation as indicated by the modal distribution of his reactive signals of increasing electrophoretic mobility. *E. coli* cells expressing fusions containing ComPΔ28$_{ADP1}$ did not demonstrate any detectable glycosylation. The same glycosylation pattern was observed for *E. coli* cells expressing maltose binding protein (MBP) fusions. Specifically, as seen in FIG. 9, *E. coli* cells expressing either MBP-AAA-ComPΔ28$_{110264}$ or MBP-GGGS-ComPΔ28$_{110264}$ in combination with PglS$_{ADP1}$ demonstrated detectable levels of glycosylation as indicated by the modal distribution of anti-His reactive signals; whereas, fusions with ComPΔ28$_{ADP1}$ were only minimally glycosylated. Lastly, to demonstrate that a previously established carrier protein used for conjugate vaccine formulations could be glycosylated by PglS with the pneumococcal CPS8, a fusion protein was engineered containing the DsbA signal peptide sequence fused to EPA. The ComPΔ28$_{110264}$ peptide was then fused with glycine-glycine-glycine-serine (GGGS; SEQ ID NO: 23) linker to the C-terminus of EPA and tested for glycosylation in the presence and absence of PglS$_{ADP1}$ in both whole cell extracts and in periplasmic extracts. As seen in FIG. 10, EPA-GGGS-ComPΔ28$_{110264}$ constructs were found to be glycosylated in both the whole cell extract and periplasmic extracts of cells co-expressing the CPS8 glycan and PglS$_{ADP1}$ as indicated by the modal distribution of anti-His reactive signals. No detectable glycosylation was observed in samples lacking a PglS ortholog or in the samples expressing PglS$_{110264}$. Collectively, PglS$_{ADP1}$ is an optimal OTase for transferring polysaccharides containing glucose at the reducing end to truncated ComP fusion proteins. Specific amino acid sequences for each fusion construct are shown in FIG. 11.

Immunization with a Glycosylated ComP Bioconjugate Elicits an Immune Response.

Figure 12A:
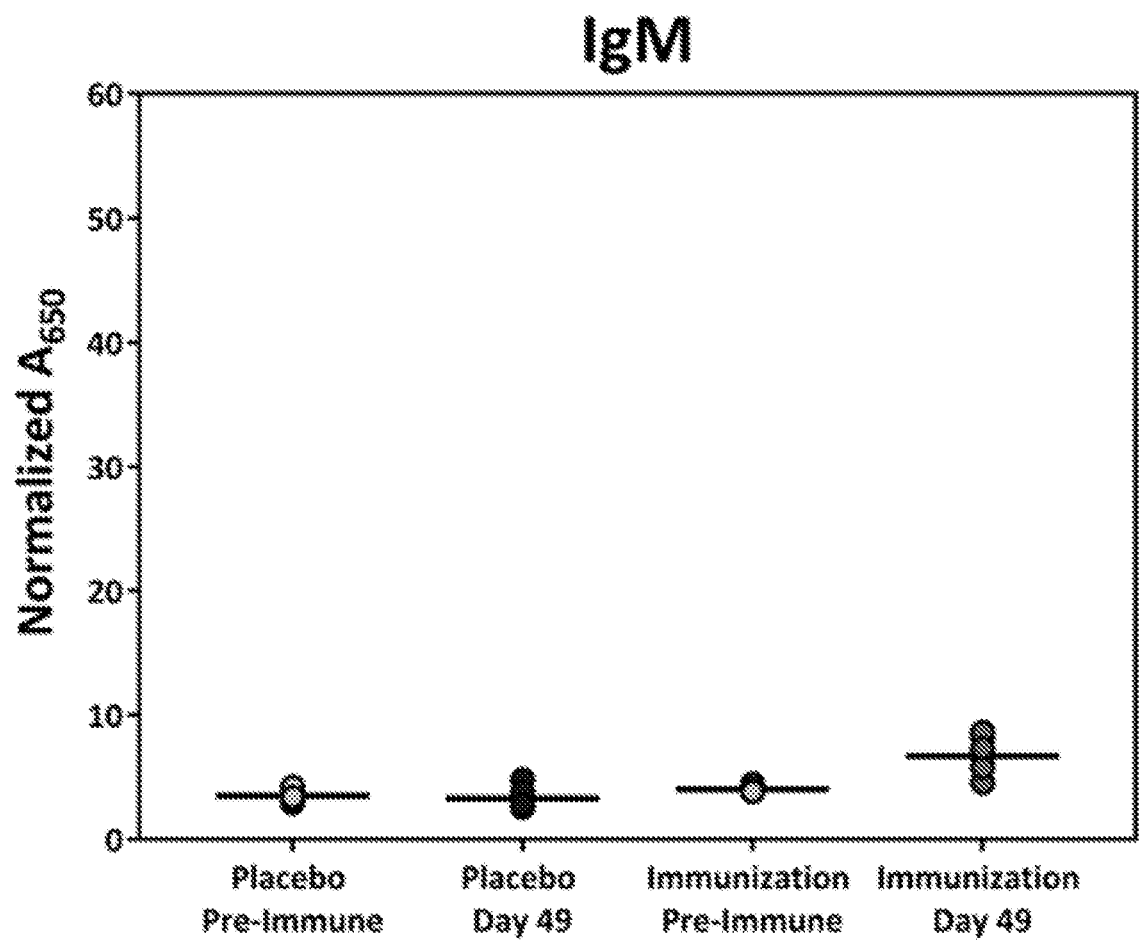
FIG. 12A-C.
Figure 12B:
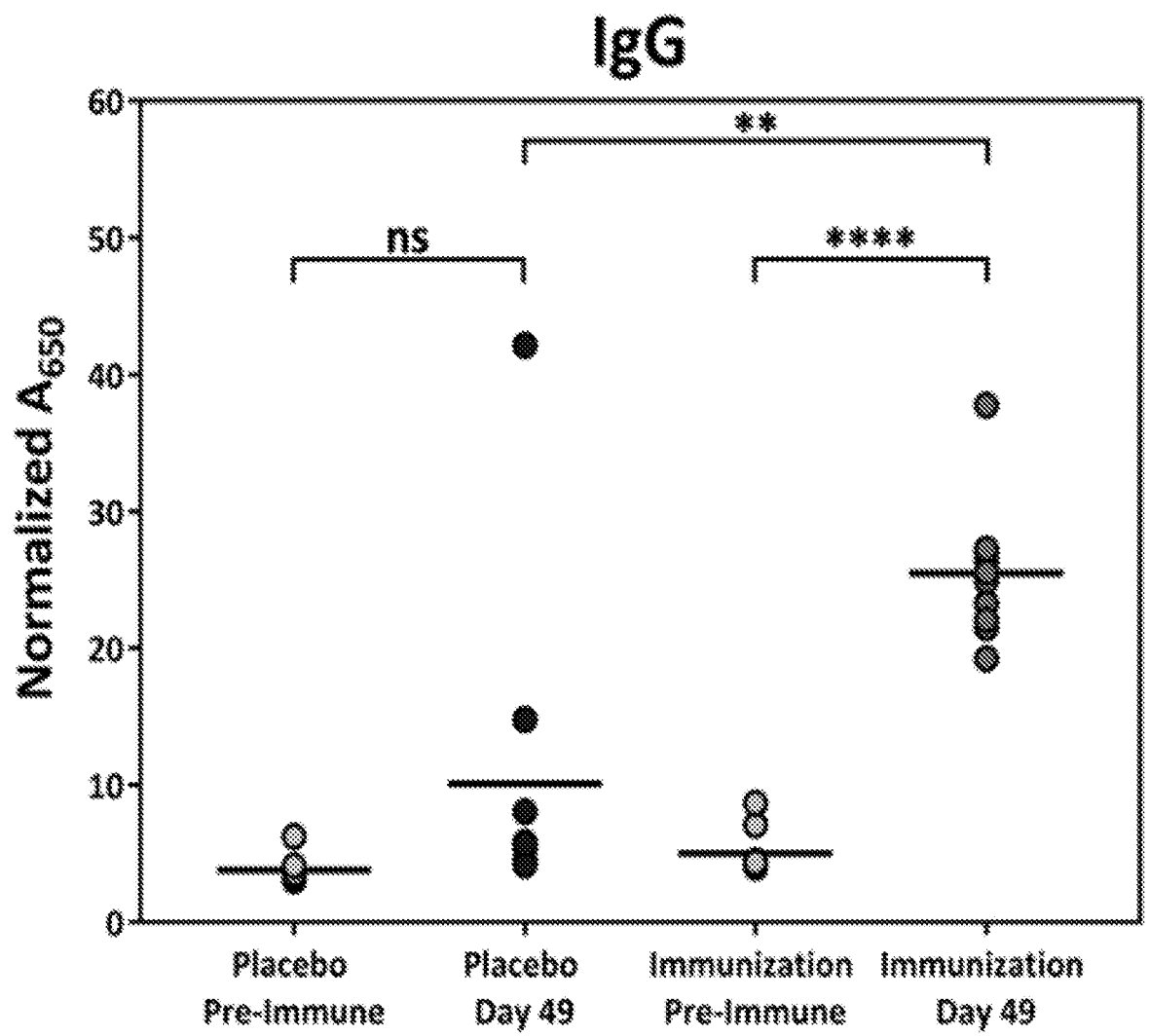

T-cell dependent immune responses to conjugate vaccines are characterized by the secretion of high affinity IgG1 antibody (Avci, F. Y., Li, X., Tsuji, M. & Kasper, D. L. Nat Med 17, 1602-1609 (2011)). The immunogenicity of a CPS14-ComP bioconjugate in a murine vaccination model was evaluated. As seen in FIG. 12A, sera collected from mice vaccinated with a CPS14-ComP bioconjugate had a significant increase in CPS14 specific IgG titers but not IgM titers. Further, secondary HRP-tagged anti-IgG subtype antibodies were employed to determine which of the IgG subtypes had elevated titers. As seen in FIG. 12B, IgG1 titers appeared to be higher than the other subtypes.

Figure 12C:
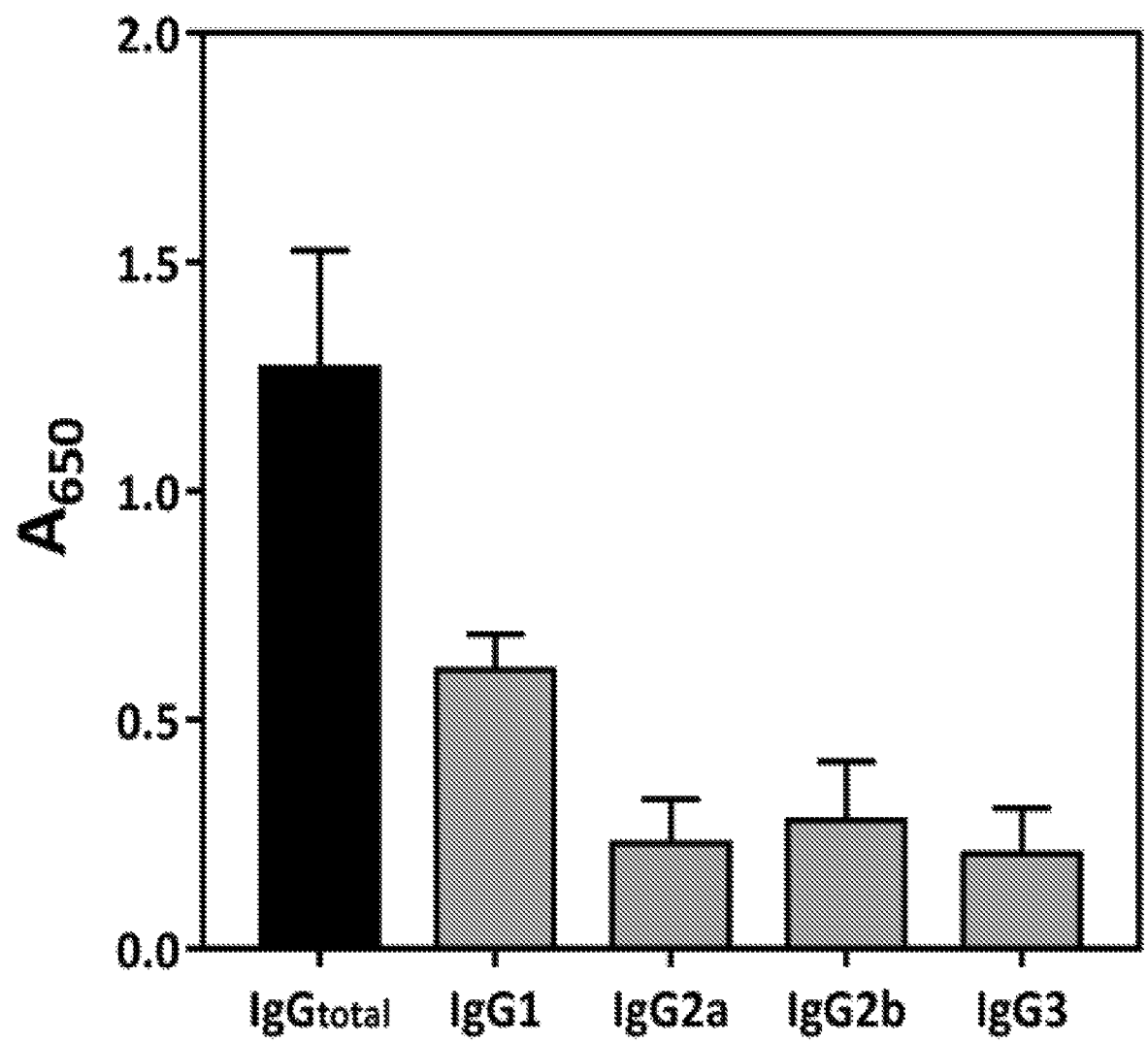
Figure 13:
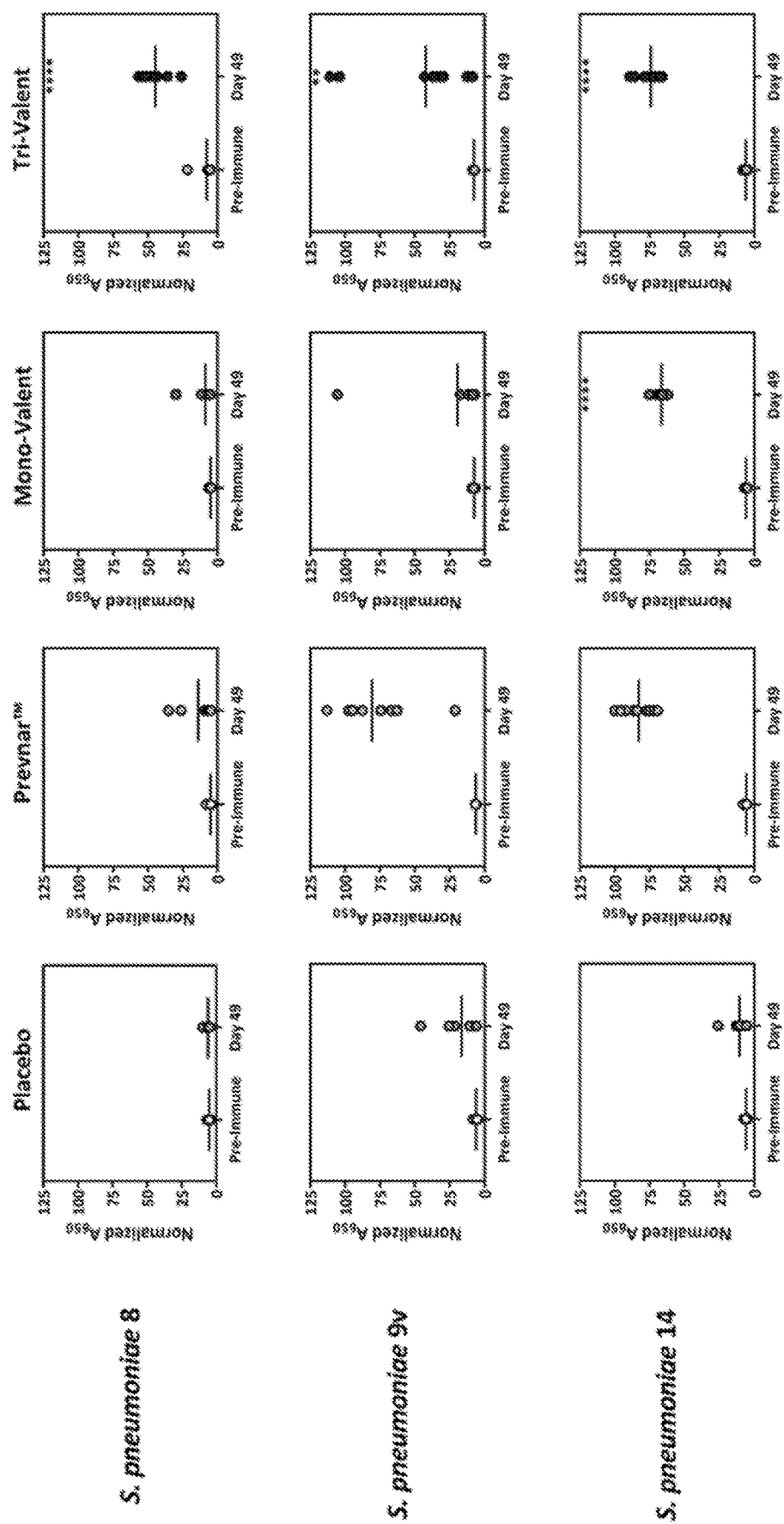
FIG. 13.

Next, a second vaccination trial was performed comparing the immunogenicity of a trivalent CPS8-, CPS9V-, and CPS14-ComP bioconjugate to the current standard of care, PREVNAR 13®. Serotypes 9V and 14 are included in PREVNAR 13® and elevated IgG titers could be seen in PREVNAR 13® immunized mice against these two serotypes (FIG. 13). The monovalent immunization against serotype 14 also showed significant induction of serotype specific IgG titers, which were similar to the preliminary immunization (FIG. 12 and FIG. 13). Mice receiving the trivalent bioconjugate, all had elevations in serotype specific IgG titers when compared to control as expected, day 49 sera have shown much more elevated IgG tires for serotypes 8 and 14 compared to serotype 9V. Nevertheless, IgG titers against 9V were still significantly higher than the placebo (FIG. 13).

Bioconjugates.

Provide herein are bioconjugates comprising an oligo- or polysaccharide covalently linked to a fusion protein. In certain aspects, the fusion protein comprises a ComP protein (ComP). In certain aspects, the fusion protein comprises a glycosylation tag or a glycosylation tag fragment of a ComP protein (as described in detail elsewhere herein).

Figure 26A:
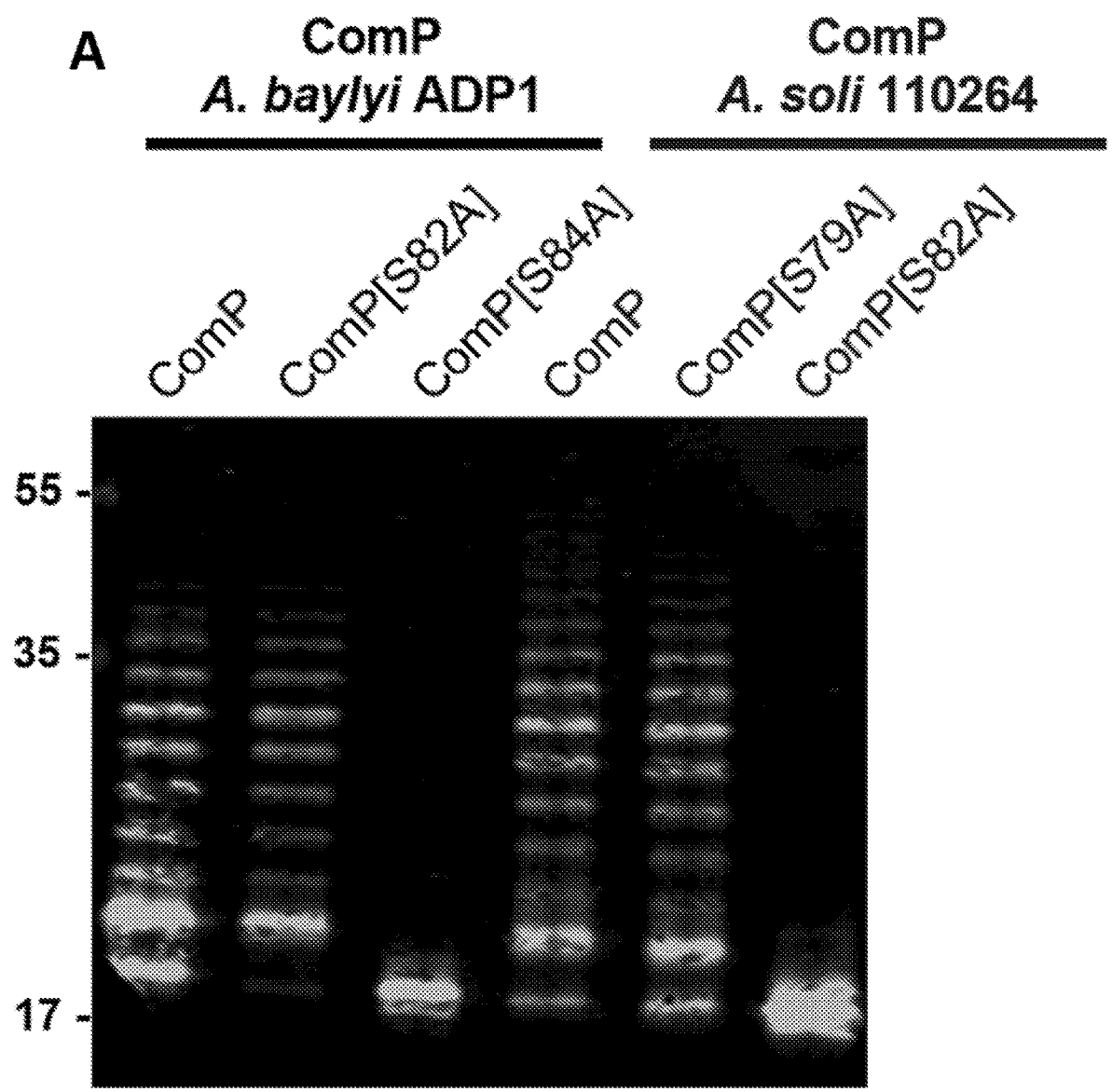
FIG. 26A,B,C.
Figure 26B:
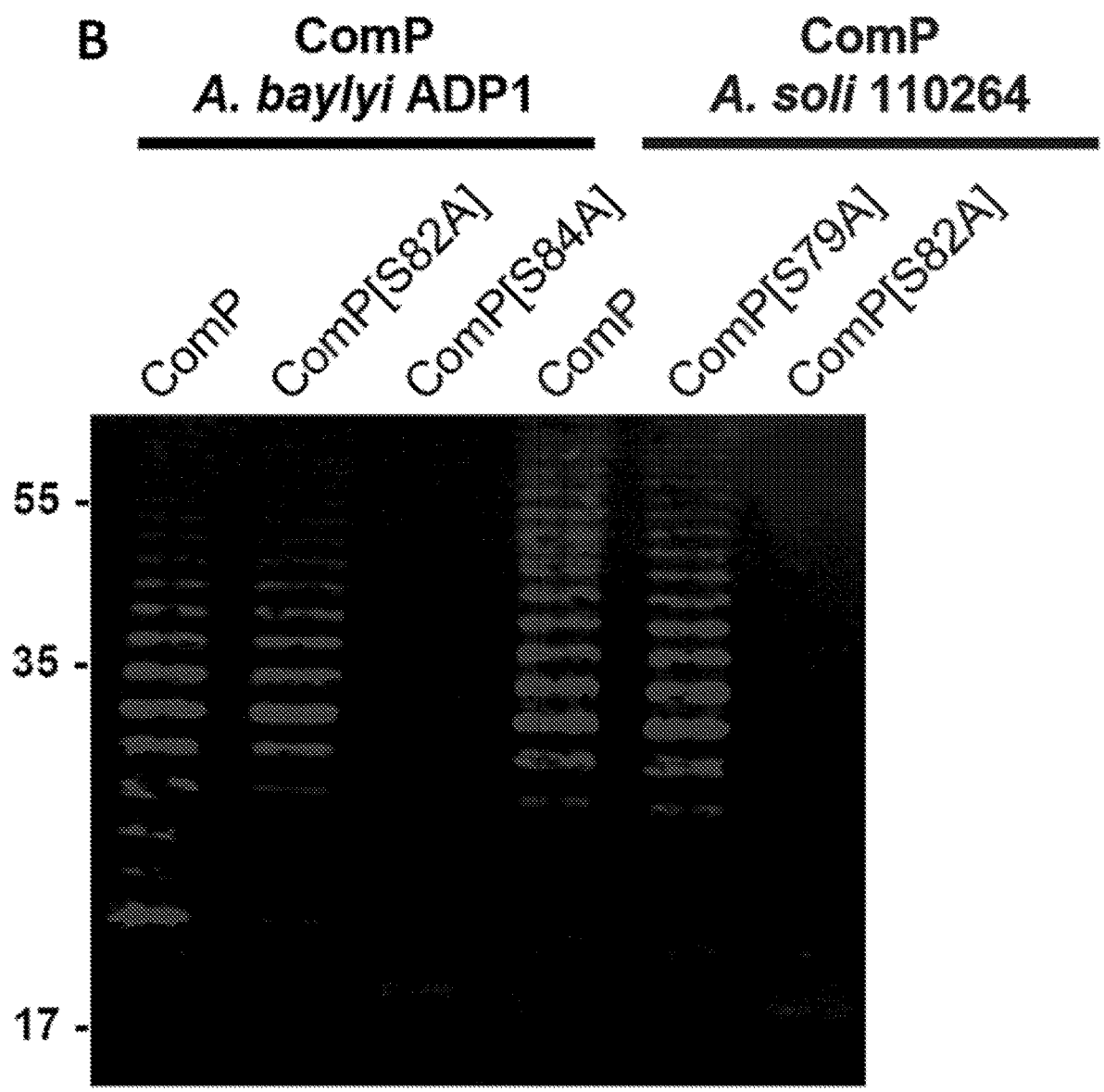
Figure 26C:
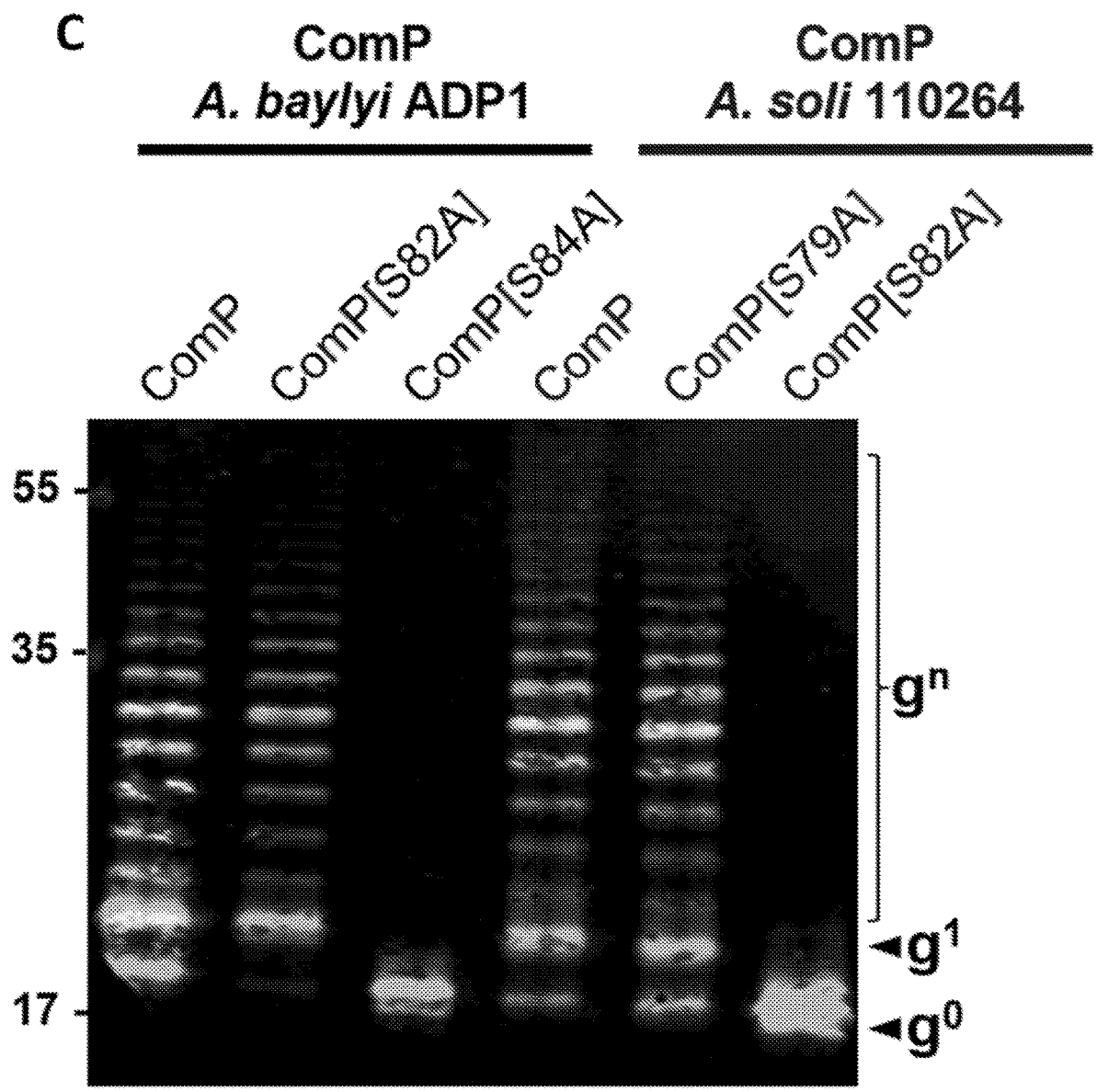
Figure 28A:
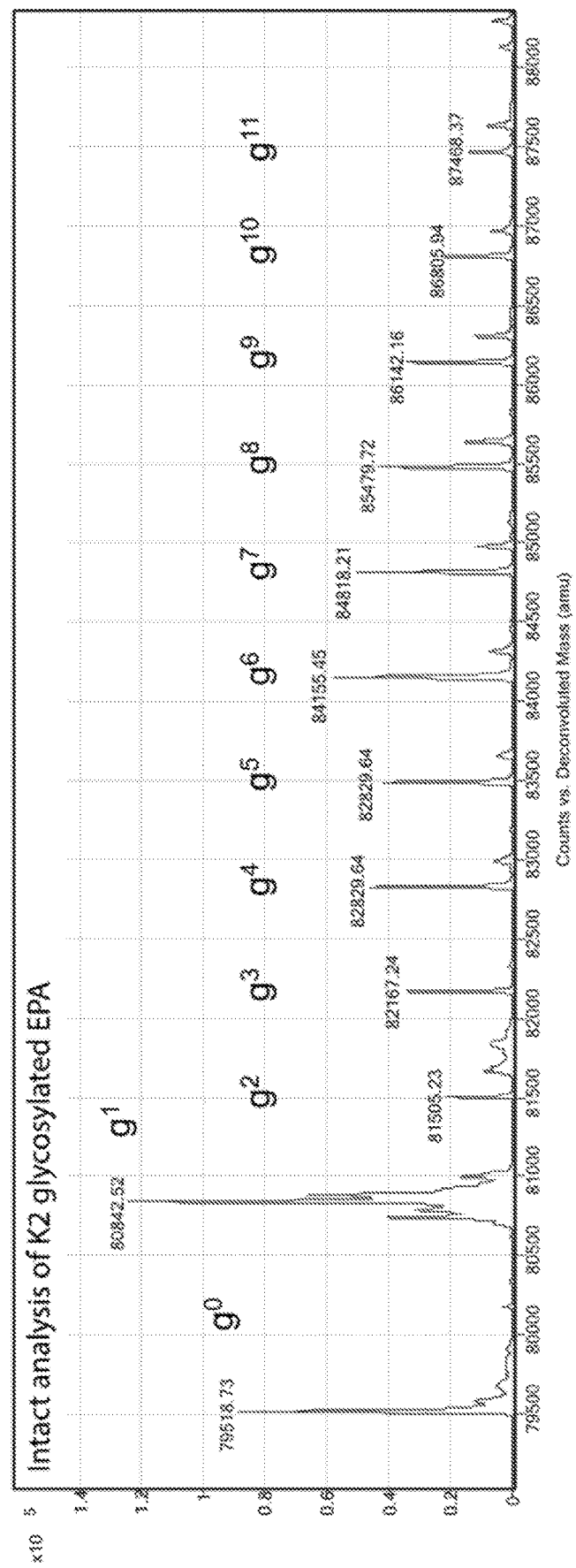
FIG. 28A,B.
Figure 28B:
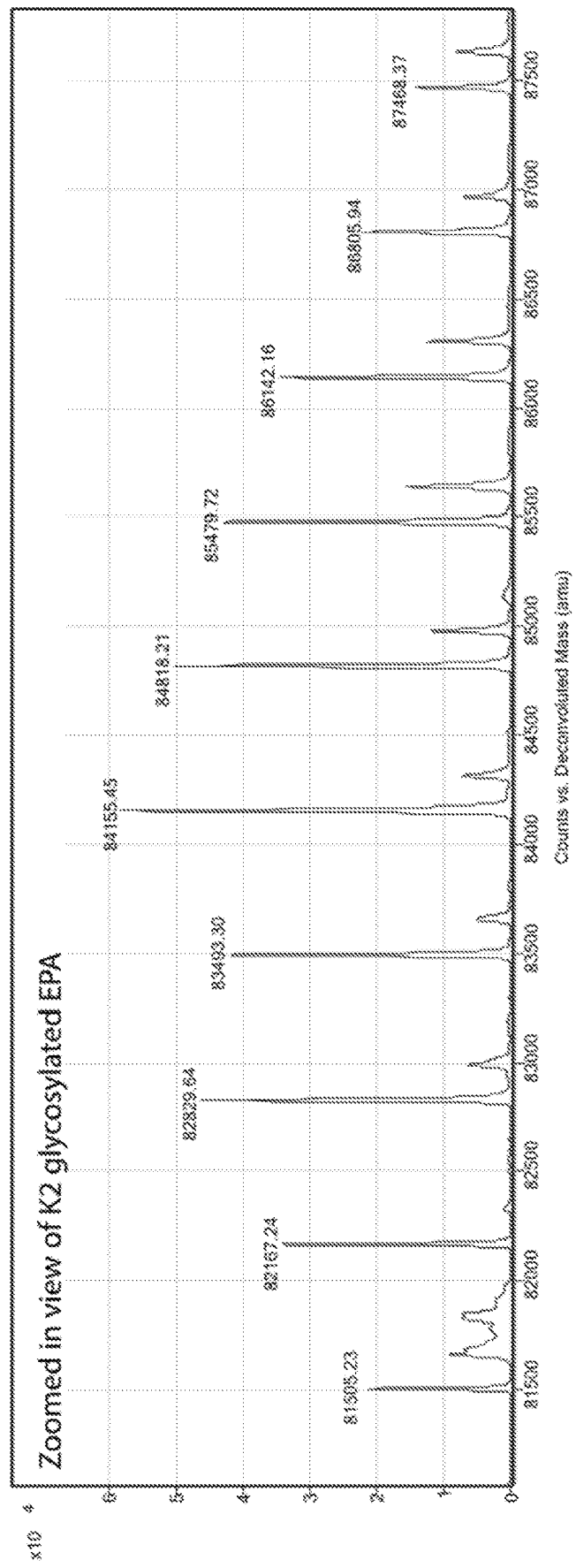

As described herein, it has been discovered that ComP is glycosylated on a serine (S) residue. This serine residue is conserved in ComP and corresponds to position 84 of SEQ ID NO: 1 (ComP$_{ADP1}$: AAC45886.1). This serine residue also corresponds to position 82 of SEQ ID NO: 2 (ComP110264: ENV58402.1) (FIGS. 26A, B, and C). Thus, in certain aspects, a fusion protein is glycosylated with an oligo- or polysaccharide on a ComP protein or glycosylation tag fragment thereof at a serine residue corresponding to the serine residue at position 84 of SEQ ID NO: 1 (ComP$_{ADP1}$: AAC45886.1). FIG. 15 shows an alignment of a region of ComP sequences including the serine (S) residue (boxed) corresponding to the serine residue at position 84 of SEQ ID NO: 1 (ComP$_{ADP1}$: AAC45886.1), which is conserved across the ComP sequences.

One of ordinary skill in the art would recognize that by aligning ComP sequences with SEQ ID NO: 1, (e.g., either full sequences or partial sequences) the conserved serine residue of a non-SEQ ID NO: 1 ComP protein disclosed herein, corresponding to the serine residue at position 84 of SEQ ID NO: 1, can be identified. Further, one of ordinary skill in the art would recognize that by aligning ComP sequences with SEQ ID NO: 1, other residues, regions, and/or features corresponding to residues, regions, and/or features of SEQ ID NO: 1 as referred to herein can be identified in the non-SEQ ID NO: 1 ComP sequence and referenced in relation to SEQ ID NO:1. And, while reference is generally made herein to SEQ ID NO: 1, by analogy, reference can similarly be made to any residue, region, feature and the like of any ComP sequence disclosed herein.

A ComP protein is a protein that has been identified as ComP protein consistent with the description provided herein. For example, representative examples of ComP proteins include, but are not limited to: AAC45886.1 ComP [Acinetobacter sp. ADM]; ENV58402.1 hypothetical protein F951_00736 [Acinetobacter soli CIP 110264]; APV36638.1 competence protein [Acinetobacter soli GFJ-2]; PKD82822.1 competence protein [Acinetobacter radioresistens 50v1]; SNX44537.1 type IV pilus assembly protein PilA [Acinetobacter puyangensis ANC 4466]; and OAL75955.1 competence protein [Acinetobacter sp. SFC]. In certain aspects, a ComP protein comprises an amino acid sequence that is at least 50%, 60%, 70%, 75%, 80%, 85%, 90%, 95%, 96%, 97%, 98%, 99%, or 100% identical to SEQ ID NO: 1 (ComP$_{ADP1}$: AAC45886.1) and contains a serine residue corresponding to the conserved serine residue at position 84 of SEQ ID NO: 1 (ComP$_{ADP1}$: AAC45886.1). SEQ ID NO: 1 comprises a leader sequence of 28 amino acids. In certain aspects, a ComP protein comprises an amino acid sequence that is at least 50%, 60%, 70%, 75%, 80%, 85%, 90%, 95%, 97%, 98%, 99%, or 100% identical to SEQ ID NO: 7 (ComPΔ28$_{ADP1}$), SEQ ID NO: 8 (ComPΔ28$_{110264}$), SEQ ID NO: 9 (ComPΔ28$_{GFJ-2}$), SEQ ID NO: 10 (ComPΔ28$_{P50v1}$), SEQ ID NO: 11 (ComPΔ28$_{4466}$), or SEQ ID NO: 12 (ComPΔ28$_{SFC}$) that do not include the 28 amino acid leader sequence but do contain a serine residue corresponding to the conserved serine residue at position 84 of SEQ ID NO: 1 (ComP$_{ADP1}$: AAC45886.1). In certain aspects, a ComP protein comprises an amino acid sequence that is at least 50%, 60%, 70%, 75%, 80%, 85%, 90%, 95%, 97%, 98%, 99%, or 100% identical to SEQ ID NO: 7 (ComPΔ28$_{ADP1}$) that does not include the 28 amino acid leader sequence but does contain a serine residue corresponding to the conserved serine residue at position 84 of SEQ ID NO: 1 (ComP$_{ADP1}$: AAC45886.1). In certain aspects, the ComP protein comprises SEQ ID NO: 7 (ComPΔ28$_{ADP1}$), SEQ ID NO: 8 (ComPΔ28$_{110264}$), SEQ ID NO: 9 (ComPΔ28$_{GFJ-2}$), SEQ ID NO: 10 (ComPΔ28$_{P50v1}$), SEQ ID NO: 11 (ComPΔ28$_{4466}$), or SEQ ID NO: 12 (ComPΔ28$_{SFC}$). In certain aspects, the ComP protein is SEQ ID NO: 1 (ComP$_{ADP1}$: AAC45886.1), SEQ ID NO: 2 (ComP$_{110264}$: ENV58402.1), SEQ ID NO: 3 (ComP$_{GFJ-2}$: APV36638.1), SEQ ID NO: 4 (ComP$_{50v1}$: PKD82822.1), SEQ ID NO: 5 (ComP$_{4466}$: SNX44537.1), or SEQ ID NO: 6 (ComP$_{SFC}$: OAL75955.1).

In certain aspects, the oligo- or polysaccharide is produced by a bacteria or a mammalian cell. In certain aspects, the bacteria is a Gram negative bacteria. In certain aspects, the bacteria is from the genus Streptococcus. In certain aspects, the bacteria is from the genus Klebsiella. In certain aspects, the oligo- or polysaccharide is a S. pneumoniae, S. agalactiae, or S. suis capsular polysaccharide, for example, wherein the capsular polysaccharide is CPS14, CPS8, CPS9V, or CPS15b of S. pneumoniae. In certain aspects, the oligo- or polysaccharide is a Klebsiella pneumoniae, Klebsiella varricola, Klebsiella michinganenis, or Klebsiella oxytoca capsular polysaccharide. In certain aspects, the polysaccharide is a *Klebsiella pneumoniae* capsular polysaccharide. For example, in certain aspects, the polysaccharide is a serotype K1 or serotype K2 capsular polysaccharide of *Klebsiella pneumoniae*.

In certain aspects, the oligo- or polysaccharide comprises a glucose (Glc) at its reducing end, the significance of which is discussed elsewhere herein.

In certain aspects, the bioconjugate is produced in vivo in a host cell such as by any of the methods of production disclosed herein. In certain aspects, the bioconjugate is produced in a bacterial cell, a fungal cell, a yeast cell, an avian cell, an algal cell, an insect cell, or a mammalian cell. In certain aspects, the bioconjugate is produced in a cell free system. Examples of the use of a cell free system utilizing OTases other than PglS can be found in WO2013/067523A1, which in incorporated herein by reference.

As discussed elsewhere herein, in certain applications, it may be advantageous to form a fusion protein with a carrier protein or fragment thereof. In certain application, the carrier protein is one recognized in the art as useful in producing conjugate vaccines. In certain aspects, when a ComP glycosylation tag fragment is fused to a carrier protein or fragment thereof, the glycosylation tag fragment and thus the fusion protein, can be glycosylated at the conserved serine residue described elsewhere herein. In certain aspects, the fusion protein comprises a carrier protein selected from the group consisting of diphtheria toxoid CRM197, tetanus toxoid, *Pseudomonas aeruginosa* Exotoxin A (EPA), tetanus toxin C fragment, cholera toxin B subunit, *Haemophilus influenza* protein D, or a fragment thereof. In certain aspects, the carrier protein or fragment thereof is linked to the ComP protein or glycosylation tag fragment thereof via an amino acid linker, for example (GGGS)$_n$ (SEQ ID NO: 23), wherein n is at least one or AAA (SEQ ID NO: 24). In order to increase the potential immunogenicity of a ComP fusion protein, it may be advantageous to include more than one glycosylation tag. Thus, in certain aspects, the fusion protein comprise two or more, three or more, four or more, five or more, six or more, eight or more, ten or more, fifteen or more, or twenty or more glycosylation tag fragments of a ComP protein. In certain aspects, the fusion protein comprises any of 2, 3, 4, 5, 6, 7, 8, 9, 10, 11, 12, 13, 14, 15, or 20 to any of 3, 4, 5, 6, 7, 8, 9, 10, 11, 12, 13, 14, 15, 20, or 25 glycosylation tag fragments of a ComP protein. In certain aspects, multiple glycosylation tag fragments are arranged in tandem to one another in the fusion protein. In certain aspects, multiple glycosylation tag fragments are arranged apart from one another in the fusion protein, for example separated by sequences of carrier protein. In certain aspects, the glycosylation tag fragment(s) can be, for example, located at the N-terminal end of the carrier protein and/or fusion protein. In certain aspects, the glycosylation tag fragment(s) can be, for example, located at the C-terminal end of the carrier protein and/or fusion protein. In certain aspects, the glycosylation tag fragment(s) can be located internally within the carrier protein and/or fusions protein, for example, wherein a glycosylation tag fragment is located between multiple carrier proteins in a fusion protein. In certain aspects, the multiple carrier proteins can be identical in type or different in type.

Glycosylation Tag Fragment.

In certain applications, such as any of the aspects described herein, there may be advantages to using less than a whole length ComP protein, such as by removing the leader sequences or using an even smaller fragment of ComP that can still be glycosylated. Because the glycosylation site of ComP is disclosed herein as the serine at residue 84 of SEQ ID NO: 1, or a corresponding serine residue in other ComP sequences, fragments of ComP proteins can be identified comprising the ComP glycosylation site. As used herein, a fragment of a ComP protein that comprises a serine residue corresponding to the conserved serine residue at position 84 of SEQ ID NO: 1, and that can be glycosylated by a PglS OTase when incorporated into a fusion protein, is referred to herein as a glycosylation tag or glycosylation tag fragment of a ComP protein.

In certain aspects, a ComP glycosylation tag comprises an isolated fragment of ComP, wherein the fragment comprises at least 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 amino acids of a ComP protein and comprises a serine residue corresponding to serine residue 84 in SEQ ID NO: 1 (ComP$_{ADP1}$: AAC45886.1). In certain aspects, a glycosylation tag comprises a ComP protein amino acid sequence that corresponds to any of amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, or 82 of SEQ ID NO: 1 (ComP$_{ADP1}$: AAC45886.1) to any of amino acid residues 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, or 147 of SEQ ID NO: 1 (ComP$_{ADP1}$: AAC45886.1). In certain aspects, a glycosylation tag comprises a ComP protein amino acid sequence comprising any of amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, or 82 of SEQ ID NO: 1 (ComP$_{ADP1}$: AAC45886.1) to any of amino acid residues 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, or 147 of SEQ ID NO: 1 (ComP$_{ADP1}$: AAC45886.1). In certain aspects, the glycosylation tag is not more than 124, 120, 119, 118, 117, 116, 115, 100, 90, 80, 75, 70, 60, 50, 40, 30, 25, 24, 23, 22, 21, 20, 19, 18, 17, 16, 15, 14, 13, 12, 11, 10, 9, 8, 7, 6, or 5 amino acids in length.

In certain aspects, the glycosylation tag fragment of a ComP protein is a ComPΔ28 polypeptide lacking amino acid residues corresponding to amino acid residues 1 to 28 of SEQ ID NO: 1 (ComP$_{ADP1}$: AAC45886.1). For example, representative examples of ComPΔ28 polypeptides include, but are not limited to, SEQ ID NOs: 7-12. In certain aspects, the glycosylation tag fragment of the ComP protein comprises a region corresponding to the region of SEQ ID NO: 1 (ComP$_{ADP1}$: AAC45886.1) comprising the serine residue at position 84 flanked by a disulfide bond connecting predicted the alpha beta loop to the beta strand region. For example, representative examples of a region corresponding to the region of SEQ ID NO: 1 (ComP$_{ADP1}$: AAC45886.1) comprising the serine residue at position 84 flanked by a disulfide bond connecting the predicted alpha beta loop to the beta strand region include, but are not limited to: ADP1 VGVQEISASNATTNVATAT (SEQ ID NO: 39), 110264 TGVTQIASGASAATTNVASAQ (SEQ ID NO: 40), GFJ-2 VGVQEINASSSTSNVATAT (SEQ ID NO: 41), SFC AGVETIGASNKTKNVESAA (SEQ ID NO: 42), P50v1

VGVQTIAASNATKNVATAT (SEQ ID NO: 43), and 4466 NGVISASATTNVASSA (SEQ ID NO: 44).

In certain aspects disclosed herein, the glycosylation tag fragment of ComP comprises an amino acid sequence that is at least 70%, 75%, 80%, 85%, 90%, 95%, 96%, 97%, 98%, 99%, or 100% identical to an amino acid selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and NGVISASATTNVASSA (SEQ ID NO: 44), wherein the glycosylation tag comprises the serine residue corresponding to the conserved serine residue at position 84 of SEQ ID NO: 1 (ComPADP1: AAC45886.1). In certain aspects, the glycosylation tag fragment of ComP comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and NGVISASATTNVASSA (SEQ ID NO: 44), or a variant thereof having one, two, three, four, five, six, or seven amino acid substitutions, additions, and/or deletions, wherein the variant maintains the serine residue corresponding to the conserved serine residue at position 84 of SEQ ID NO: 1 (ComPADP1: AAC45886.1). In certain aspects, amino acid substitutions are conservative amino acid substitutions. In certain aspects, the glycosylation tag fragment of ComP comprises an amino acid sequence that is at least 70%, 75%, 80%, 85%, 90%, 95%, 96%, 97%, 98%, 99%, or 100% identical to VGVQEISASNATTNVATAT (SEQ ID NO: 39), wherein the glycosylation tag comprises the serine residue corresponding to the conserved serine residue at position 84 of SEQ ID NO: 1 (ComPADP1: AAC45886.1). In certain aspects, the glycosylation tag fragment of ComP comprises the amino acid sequence VGVQEISASNATTNVATAT (SEQ ID NO: 39), or a variant thereof having one, two, three, four, five, six, or seven amino acid substitutions, additions, and/or deletions, wherein the variant maintains the serine residue corresponding to the conserved serine residue at position 84 of SEQ ID NO: 1 (ComPADP1: AAC45886.1). In certain aspects, amino acid substitutions are conservative amino acid substitutions.

In certain aspects, a glycosylation tag fragment of a ComP protein comprises an amino acid sequence of at least 5, 10, 15, 20, 30, 35, or 40 consecutive amino acids of the amino acid consensus sequence of SEQ ID NO: 37 (Table 3 below), wherein said glycosylation tag fragment comprises the serine residue corresponding to the conserved serine residue at position 84 of SEQ ID NO: 1 (ComP$_{ADP1}$: AAC45886.1). In certain aspects, a glycosylation tag fragment of a ComP protein comprises the amino acid consensus sequence of SEQ ID NO: 37, or variant of SEQ ID NO: 37 having one, two, three, four, five, six, or seven amino acid substitutions, additions, and/or deletions, wherein the variant sequence maintains the serine residue corresponding to the conserved serine residue at position 84 of SEQ ID NO: 1 (ComPADP1: AAC45886.1). In certain aspects, amino acid substitutions are conservative amino acid substitutions.

In certain aspects, a glycosylation tag fragment of a ComP protein comprises an amino acid sequence of at least 5, 6, 7, 8, 9, 10, 11, 12, 13, 14, 15, 16, 17, 18, 19, or 20 consecutive amino acids of the amino acid consensus sequence of SEQ ID NO: 38 or 45 (Table 3 below), wherein said glycosylation tag fragment comprises the serine residue corresponding to the conserved serine residue at position 84 of SEQ ID NO: 1 (ComP$_{ADP1}$: AAC45886.1). In certain aspects, a glycosylation tag fragment of a ComP protein comprises the amino acid consensus sequence of SEQ ID NO: 38 or 45, or variant of SEQ ID NO: 38 or 45 having one, two, three, four, five, six, or seven amino acid substitutions, additions, and/or deletions, wherein the variant sequence maintains the serine residue corresponding to the conserved serine residue at position 84 of SEQ ID NO: 1 (ComPADP1: AAC45886.1). In certain aspects, amino acid substitutions are conservative amino acid substitutions.

In certain aspects, the glycosylation tag is attached to a heterologous protein such as a carrier protein. Thus, certain aspects provide for a fusion protein comprising a ComP glycosylation tag disclosed herein. In certain aspects, the fusion protein comprises a carrier protein, representative examples of which include but are not limited to diphtheria toxoid CRM197, tetanus toxoid, *Pseudomonas aeruginosa* Exotoxin A (EPA), tetanus toxin C fragment, cholera toxin B subunit, *Haemophilus influenza* protein D, or a fragment thereof. In certain aspects, the fusion protein comprises a linker sequence as disclosed elsewhere herein. In certain aspects, the fusion protein is glycosylated and further in certain aspects, the fusion protein is glycosylated on a glycosylation tag region at a serine residue corresponding to the serine residue at position 84 of SEQ ID NO: 1 (ComP$_{ADP1}$: AAC45886.1).

Conjugate Vaccines.

Disclosed herein is a pneumococcal bioconjugate vaccine containing a conventional vaccine carrier. Certain aspects comprise the use of a ComP fragment as a glycosylation tag (aka "glycotag"). In certain aspects, the glycotag can be added to the C-terminus and/or N-terminus of a carrier protein. For example, in certain aspects, the glycotag is added to the C-terminus of the conventional carrier protein *Pseudomonas aeruginosa* Exotoxin A (EPA). It has been demonstrated that in certain aspects, the glycotag/carrier fusion protein can be paired with the CPS8 polysaccharide and use of PglS, generating a carrier protein-CPS8 bioconjugate, a first of its kind pneumococcal bioconjugate vaccine. For example, in certain aspects, an EPA fusion can be paired with the CPS8 polysaccharide and use of PglS, generating an EPA-CPS8 bioconjugate. It was demonstrated that the EPA-CPS8 bioconjugate vaccine elicited high IgG titers specific to serotype 8 specific that were protective as determined via bactericidal killing. Importantly, vaccination with as little as 100 ng of polysaccharide in the EPA-CPS8 bioconjugate was able to provide protection. Thus, certain aspects provide for a CPS8 pneumococcal bioconjugate vaccine.

It is contemplated that a conjugate vaccine (such as the EPA vaccine construct) can comprise additional/multiple sites of glycosylation to increase the glycan to protein ratio as well as expand upon the number of serotypes in order to develop a comprehensive pneumococcal bioconjugate vaccine.

In certain aspects, a bioconjugate or glycosylated fusion protein disclosed herein is a conjugate vaccine that can be administered to a subject for the prevention and/or treatment of an infection and/or disease. In certain aspects, the conjugate vaccine is a prophylaxis that can be used, e.g., to immunize a subject against an infection and/or disease. In certain aspects, the bioconjugate is associated with (such as in a therapeutic composition) and/or administered with an adjuvant. Certain aspects provide for a composition (such as a therapeutic composition) comprising a conjugate vaccine described herein and an adjuvant. In certain aspects, when the conjugate vaccine is administered to a subject, it induces an immune response. In certain aspects, the immune response elicits long term memory (memory B and T cells). In certain aspects, the immune is an antibody response. In certain aspects, the antibody response is a serotype-specific antibody response. In certain aspects, the antibody response is an IgG or IgM response. In certain aspects where the antibody response is an IgG response, the IgG response is an IgG1 response. Further, in certain aspects, the conjugate vaccine generates immunological memory in a subject administered the vaccine.

Certain aspects provide for producing a vaccine against an infection and/or disease. In certain aspects the method comprises isolating a bioconjugate or fusion protein disclosed herein (conjugate vaccine) and combining the conjugate vaccine with an adjuvant. In certain aspects, the vaccine is a conjugate vaccine against pneumococcal infection. In certain aspects, the disease is pneumonia.

Importantly, the aspects disclosed herein are not limited to pneumococcal polysaccharides, but in fact, have vast applicability for generating bioconjugate vaccines for many important human and animal pathogens that are incompatible with PglB and PglL. Notable examples include the human pathogens *Klebsiella pneumoniae* and Group B *Streptococcus* as well as the swine pathogen *S. suis*, all immensely relevant pathogens with no licensed vaccines available.

Methods and Reagents for In Vivo Glycosylation.

Disclosed herein are methods for the in vivo conjugation of an oligo- or polysaccharide to a polypeptide (in vivo glycosylation). In certain aspects, the method comprises covalently linking the oligo- or polysaccharide to the polypeptide with a PglS oligosaccharyltransferase (OTase) (described elsewhere herein). In certain aspects, the polypeptide comprises a ComP protein or a glycosylation tag fragment thereof. In certain aspects, the polypeptide comprises a ComP protein or a glycosylation tag fragment thereof linked to a heterologous polypeptide such as a carrier protein. Representative examples of PglS OTases include, but are not limited to $PglS_{110264}$, $PglS_{ADP1}$, $PglS_{GFJ-2}$, $PglS_{50v1}$, $PglS_{4466}$, and $PglS_{SFC}$. ComP proteins are described in detail elsewhere and representative examples include, but are not limited to $ComP_{110264}$, $ComP_{ADP1}$, $ComP_{GFJ-2}$, $ComP_{50v1}$, $ComP_{4466}$, and $ComP_{SFC}$. It will be recognized that while a PglS OTase from an organism would naturally glycosylate the ComP protein from that organism (e.g., $PglS_{110264}$ glycosylates $ComP_{110264}$) in certain aspects, a PglS from one organism glycosylates a ComP from a different organism (e.g., $PglS_{ADP1}$ glycosylates $ComP_{110264}$). For example, in certain aspects, the PglS OTase is $PglS_{ADP1}$. In certain aspects, where the PglS OTase is $PglS_{ADP1}$, the ComP protein glycosylated is not $ComP_{ADP1}$. For example, in certain aspects where the PglS OTase is $PglS_{ADP1}$, the ComP protein is $ComP_{110264}$. Of course, it will be recognized that a PglS OTase does not naturally glycosylate a ComP protein or a glycosylation tag fragment thereof, even from the same organism as the PglS Otase, when the ComP protein or glycosylation tag fragment thereof is linked to a heterologous carrier protein.

In certain aspects for any combination of PglS and ComP, the ComP protein or glycosylation tag fragment thereof is glycosylated at a serine residue corresponding to the serine residue at position 84 of SEQ ID NO: 1 ($ComP_{ADP1}$: AAC45886.1).

In certain aspects disclosed herein, the in vivo glycosylation occurs in a host cell. In certain aspects, for example, the host cell can be a mammalian cell, fungal cell, yeast cell, insect cell, avian cell, algal cell, or bacterial cell. In certain aspects, the host cell is a bacterial cell, for example, *E. coli*.

In certain aspects, the method comprises culturing a host cell comprising the components necessary for the conjugation of the oligo- or polysaccharide to the polypeptide. In general, these components are the oligosaccharyltransferase, the acceptor polypeptide to be glycosylated, and the oligo- or polysaccharide. In certain aspects, the method comprises culturing a host cell that comprises: (a) a genetic cluster encoding for the proteins required to synthesize the oligo- or polysaccharide; (b) a PglS OTase; and (3) the acceptor polypeptide. Further, it has been discovered that production of the oligo- or polysaccharide can be enhanced by a transcriptional activator. In certain aspects, the production of the oligo- or polysaccharide is enhanced by the *K. pneumoniae* transcriptional activator rmpA (*K. pneumoniae* NTUH K-2044) or a homolog of the *K. pneumoniae* transcriptional activator rmpA (*K. pneumoniae* NTUH K-2044). In certain aspects, the method further comprises expressing and/or providing such a transcriptional activator in the host cell along with the other components.

In certain aspects, the carrier protein linked to the ComP protein or a glycosylation tag fragment thereof is, for example, diphtheria toxoid CRM197, tetanus toxoid, *Pseudomonas aeruginosa* Exotoxin A (EPA), tetanus toxin C fragment, cholera toxin B subunit, *Haemophilus* influenza protein D, or a fragment thereof.

In certain aspects, the method produces a conjugate vaccine as described herein.

Certain aspects also provide for a host cell comprising the components for in vivo glycosylation of an acceptor ComP protein or glycosylation tag fragment thereof. In certain aspects, a host cell comprises: (a) a genetic cluster encoding for the proteins required to synthesize an oligo- or polysaccharide; (b) a PglS OTase; and (3) an acceptor polypeptide comprising a ComP protein or a glycosylation tag fragment thereof. In certain aspects, the acceptor polypeptide is a fusion protein. In certain aspects, the host cell further comprises a transcriptional activator such as described above along with the other components.

In certain aspects, a host cell comprises an isolated nucleic acid encoding a PglS OTase. In certain aspects a host cell comprises an isolated nucleic acid encoding the ComP acceptor polypeptide. In certain aspects, a host cell comprises a genetic cluster encoding for the proteins required to synthesize an oligo- or polysaccharide. In certain aspects, a host cell comprises at least two of an isolated nucleic acid encoding a PglS OTase, an isolated nucleic acid encoding the ComP acceptor polypeptide, and genetic cluster encoding for the proteins required to synthesize an oligo- or polysaccharide. In certain aspects, a host cell comprises a nucleic acid encoding a PglS OTase of one organism and a nucleic acid encoding the ComP acceptor polypeptide from a different organism.

Certain aspects provide for an isolated nucleic acid encoding the ComP protein, ComP glycosylation tag fragment, and/or ComP fusion protein described anywhere herein. In certain aspects, an isolated nucleic acid referred to herein is a vector or is contained within a vector. In certain aspects, an isolated nucleic acid referred to herein is inserted and/or has been incorporated into a heterologous genome or a heterologous region of a genome.

Administration.

Provided herein are methods of inducing a host immune response against a pathogen. In certain aspects, the pathogen is a bacterial pathogen. In certain aspects, the host is immunized against the pathogen. In certain aspects, the method comprises administering to a subject in need of the immune response an effective amount of a ComP conjugate vaccine, glycosylated fusion protein, or any other therapeutic/immunogenic composition disclosed herein. Certain aspects provide a conjugate vaccine, glycosylated fusion protein, or other therapeutic/immunogenic composition disclosed herein for use in inducing a host immune response against a bacterial pathogen and immunization against the bacterial pathogen. Examples of immune responses include but are not limited to an innate response, an adaptive response, a humoral response, an antibody response, cell mediated response, a B cell response, a T cell response, cytokine upregulation or downregulation, immune system cross-talk, and a combination of two or more of said immune responses. In certain aspects, the immune response is an antibody response. In certain aspects, the immune response is an innate response, a humoral response, an antibody response, a T cell response, or a combination of two or more of said immune responses.

Also provided herein are methods of preventing or treating a bacterial disease and/or infection in a subject comprising administering to a subject in need thereof a conjugate vaccine, a fusion protein, or a composition disclosed herein. In certain aspects, the infection is a localized or systemic infection of skin, soft tissue, blood, or an organ, or is auto-immune in nature. In certain aspects, the disease is pneumonia. In certain aspects, the infection is a systemic infection and/or an infection of the blood. In certain aspects disclosed herein, the subject is a vertebrate. In certain aspects the subject is a mammal such as a dog, cat, cow, horse, pig, mouse, rat, rabbit, sheep, goat, guinea pig, monkey, ape, etc. And, for example, in certain aspects the mammal is a human.

In any of the aspects of administration disclose herein, the composition is administered via intramuscular injection, intradermal injection, intraperitoneal injection, subcutaneous injection, intravenous injection, oral administration, mucosal administration, intranasal administration, or pulmonary administration.

EXAMPLES

Bacterial Strains, Plasmids and Growth Conditions.
Strains and plasmids used in this work are listed in Table 1.

TABLE 1

Strains and plasmids employed in this study.

| Strains/Plasmids | Description |
| --- | --- |
| Strains | |
| E. coli SDB1 | W3110, Δ waaL ligase, ΔwecA glycosyltransferase |
| E. coli DH5α | General cloning strain |
| S. pneumoniae serotype 8, 9V, and 14 | Wild type pneumococci strains expressing either the serotype 8, 9V, or 14 capsular polysaccharides |
| K. pneumoniae serotype K1 and K2 | Wild type K. pneumoniae strains expressing either the serotype K1 or K2 capsular polysaccharides |
| Plasmids | |
| pEXT20 | Cloning vector, $Amp^R$, IPTG inducible |
| pACT3 | Cloning vector, $Cm^R$, IPTG inducible |
| pMN1 | C-6X His-tagged ComP cloned in BamHI and SalI sites of pEXT20, $Amp^R$, IPTG inducible |
| pMN2 | Non-coding region and PglS cloned in SalI and PstI sites of pMN1, $Amp^R$, IPTG inducible |
| pMN4 | PglS[H324A] in pMN2 background |
| pMN8 | Non-coding region and PglS cloned in SalI and PstI sites of pEXT20, $Amp^R$, IPTG inducible |
| pMN9 | ComP[S82A] mutant of pMN2 |
| pMN10 | ComP[S84A]mutant of pMN2 |
| pMAF10 | HA-tagged PglB cloned in pMLBAD, TpR, Arabinose inducible |
| pAMF10 | C-10 × His-tagged NmPglL cloned into pEXT20, AmpR, IPTG inducible |
| pIH18 | C-6X His-tagged AcrA from C. jejuni cloned into pEXT21, SpR, IPTG inducible |
| pAMF22 | C-6X His-tagged dsbAI from N. meningitidis MC58 cloned into pMLBAD, $Tp^R$ Arabinose inducible |
| pACYCpglBmut | pACYC184-based plasmid encoding the C. jejuni pgl locus with mutations W458A and D459A in PglB. $Cm^R$, IPTG inducible. |
| pNLP80 | S. pneumoniae CPS14 cluster on pWSK129, $Kan^R$ |
| pB-8 | S. pneumoniae CPS8 cluster on pBBR1MCS-3, $Tc^R$ |
| pWKS130-9V | S. pneumoniae CPS9v cluster on pWSK130, $Kan^R$ |
| pBBR1MCS-K1 | K. pneumoniae K1 cluster in pBBR1MCS2 |
| pBBR1MCS-K2 | K. pneumoniae K2 cluster in pBBR1MCS2 |
| pACT3-rmpA | rmpA cloned into pACT3 |
| pEXT20-ComP-PglS_110264 | ComP and PglS from A. soli CIP 110264 cloned into pEXT20 |
| pEXT20-ComP$_{110264}$ | ComP$_{110264}$ with a c-terminal hexa-his tag from A. soli CIP 110264 cloned into pEXT20 |
| pACT3-PglS$_{110264}$ | PglS$_{110264}$ w from A. soli CIP 110264 cloned into pEXT20 |
| pACT3-PglS$_{ADp1}$ | PglS$_{ADp1}$ w from A. baylyi ADP1 cloned into pEXT20 |
| pACT3-rmpA-pglS$_{ADp1}$ | rmpA and pglS$_{APD1}$ cloned into pACT3 |
| pEXT20-DsbA-AAA-ComPΔ23$_{110264}$ | DsbA fused to a triple alanine peptide linking ComPΔ23$_{110264}$ with a c-terminal hex-his tag |
| pEXT20-DsbA-GGGS-ComPΔA23$_{110264}$ | DsbA fused to a gly-gly-gly-ser peptide linking ComPΔA23$_{110264}$ with a c-terminal hex-his tag |
| pEXT20-DsbA-AAA-ComPΔ23$_{ADP1}$ | DsbA fused to a triple alanine peptide linking ComPΔ23$_{ADP1}$ with a c-terminal hex-his tag |
| pEXT20-DsbA-GGGS-ComPΔ23$_{ADP1}$ | DsbA fused to a gly-gly-gly-ser peptide linking ComPΔ23$_{ADP1}$ with a c-terminal hex-his tag |
| pEXT20-MBP-AAA-ComPΔ23$_{110264}$ | MBP fused to a triple alanine peptide linking ComPΔ23$_{110264}$ with a c-terminal hex-his tag |
| pEXT20-MBP-GGGS-ComPΔ23$_{110264}$ | MBP fused to a gly-gly-gly-ser peptide linking ComPΔ23$_{110264}$ with a c-terminal hex-his tag |
| pEXT20-MBP-AAA-ComPΔ23$_{ADP1}$ | MBP fused to a triple alanine peptide linking ComPΔ23$_{ADP1}$ with a c-terminal hex-his tag |
| pEXT20-MBP-GGGS-ComPΔ23$_{ADP1}$ | MBP fused to a gly-gly-gly-ser peptide linking ComPΔ23$_{ADP1}$ with a c-terminal hex-his tag |
| pEXT20-EPA-GGGS-ComPΔ23$_{110264}$ | The DsbA signal peptide fused to EPA fused to a gly-gly-gly-ser peptide linking ComPΔ23$_{110264}$ with a c-terminal hex-his tag |

Unless otherwise stated, E. coli strains were grown in Terrific Broth (TB) at 37° C. overnight. S. pneumoniae strains were grown in brain heart infusion (BHI) broth or sheep blood agar plates at 37° C. in 5% $CO_2$. For plasmid selection the antibiotics were used at the following concentrations: ampicillin (100 µg/mL), tetracycline (20 µg/mL), chloramphenicol (12.5 µg/mL), kanamycin (20 µg/mL) and spectinomycin (80 µg/mL) were added as needed.

Heterologous Glycosylation in E. coli.
For all heterologous glycosylation experiments, the E. coli SDB1 cell line was used as it has previously been established as a suitable strain for glycoengineering. Electrocompetent *E. coli* SDB1 was prepared as described by Dower and colleagues. Cells were electroporated with plasmids encoding the glycan synthesis loci, acceptor proteins and OTases. Colonies were picked and grown at 37° C. in TB with appropriate antibiotic selection and immediately induced with 0.05-0.1 mM IPTG or 0.2% arabinose as needed and left overnight at 37° C. Cultures requiring arabinose induction received a second dose of arabinose after 4 hours. Cell pellets were obtained at stationary phases and prepared for western blot analysis.

Western Blotting.

Cell lysates containing the equivalent of $OD_{600}$=0.1 units were loaded on 12.5% in-house prepared SDS-PAGE gels, which were then transferred to nitrocellulose membranes (Biorad). Western blotting was performed according to previously published protocols. Nitrocellulose membranes were then visualized using an Odyssey Infrared Imaging System (LiCor Biosciences, USA).

Purification of Proteins and Glycoproteins.

C-terminally Hexa-histidine-tagged ComP and ComP bioconjugates were purified from *E. coli* total membrane preparations. Cells were grown overnight in 2 L of terrific broth at 37° C., washed with phosphate buffered saline (PBS) buffer, and resuspended in 60 mL of the same buffer. Cells were lysed by two rounds of cell disruption at approximately 20 kPSI using a French press (Aminco) followed by the addition of a protease inhibitor cocktail (Roche). Lysates were centrifuged twice for 30 minutes at 20,000×g to pellet cell debris. Supernatants were ultra-centrifuged at 100,000×g for 60 minutes to pellet total membranes. The pellets were resuspended in PBS buffer containing 0.5% n-dodecyl-β-D-maltoside (DDM) and membrane proteins were solubilized by tumbling for 48 hours. An equal volume of PBS was added to the suspension to reduce detergent concentration to 0.25% and the suspension was ultra-centrifuged at 100,000×g for 60 minutes. Solubilized membranes were filtered through 0.45 μm and 0.22 μm filters and loaded on a His-Trap HP column (GE Healthcare) fitted to an ÄKTA purifier (Amersham Biosciences, Sweden). The column was equilibrated with a PBS/DDM buffer containing 20 mM imidazole before loading the sample. Unbound proteins were removed by washing the column with seven column volumes of buffer containing 20 mM and 30 mM imidazole in PBS stepwise. To elute proteins bound to the column, a gradient elution with an incremental increase in imidazole concentration was used. The majority of unconjugated and conjugated ComP eluted between 180 mM and 250 mM imidazole. Imidazole was removed by an overnight round of dialysis followed by two 2-hour rounds through a 3.5 kDa dialysis membrane (Spectrum labs) in a 250 mL dialysis buffer composed of PBS containing 0.25% w/v DDM. The final theoretical concentration of imidazole post dialysis was about 0.007 mM. Proteins were quantified using a DC kit (biorad) after which the samples were diluted to the appropriate concentrations for mouse immunizations.

Murine Model Immunizations.

The immunogenicity of a CPS14-ComP bioconjugate in a murine vaccination model was evaluated. Two groups of mice (n=10) individually received 3 μg of either unglycosylated ComP or CPS14-ComP bioconjugate. Mice were boosted on days 14 and 28, and sacrificed on day 49 for whole blood collection. Each vaccine was formulated based on total protein. Using an enzyme linked immunosorbent assay (ELISA) with a serotype 14 strain of *S. pneumoniae* adsorbed to each well, IgM and IgG responses to CPS14 were compared. As seen in FIG. 12A,B, sera collected from mice vaccinated with a CPS14-ComP bioconjugate had an increased IgG response specific to CPS14 (FIG. 12A) but not and increased IgM response (FIG. 12B). Further, secondary HRP-tagged anti-IgG subtype antibodies to were employed determine which of the IgG subtypes were present in CPS14-ComP vaccinated mice (FIG. 12C). As seen in FIG. 12C, the CPS14-specific IgG1 response was higher than the other subtypes, which is consistent with previous findings for pneumococcal conjugate vaccines (Wuorimaa et al. *J Infect Dis* 184, 1211-1215 (2001); Soininen, A., Seppala, I., Nieminen, T., Eskola, J. & Kayhty, H. *Vaccine* 17, 1889-1897 (1999)).

There are more than 90 serotypes of *S. pneumoniae* (Geno, K. A. et al. *Clin Microbiol Rev* 28, 871-899 (2015); Bentley, S. D., et al. *PLoS Genet* 2, e31 (2006)). Many increasingly prevalent serotypes, like serotypes 8, 22F, and 33F are not included in currently licensed vaccines (Pilishvili, T., et al. *J Infect Dis* 201, 32-41 (2010)). Therefore, versatility of PglS to generate a multivalent pneumococcal bioconjugate vaccine against two serotypes included in PREVNAR 13® (serotype 9V and 14) and one serotype not included (serotype 8) was tested. The aforementioned CPSs all contain Glc as the reducing end sugar and are therefore not compatible with other commercially exploited conjugating enzymes. As seen in FIG. 21A-F, western blot analyses of affinity purified proteins from whole cells co-expressing PglS, ComP, and either the CPS8 or CPS9V polysaccharides resulted in the generation CPS-specific ComP bioconjugates, respectively. Again, to confirm that the material purified was not contaminated with lipid-linked polysaccharides, samples were treated with proteinase K and observed a loss of signal when analyzed via western blotting, confirming that the bioconjugates were proteinaceous.

Next, a vaccination trial was performed to determine the immunogenicity of a trivalent CPS8-, CPS9V-, and CPS14-ComP pneumococcal bioconjugate vaccine (FIG. 22A-L). Three control groups were included: one group receiving carrier protein alone (unglycosylated ComP); another group receiving a monovalent dose of the CPS14-ComP bioconjugate to account for IgG specificity when analyzing immune responses against other serotypes; and a third group receiving PREVNAR 13® as a positive control. All immunogen groups contained and equal mixture of Freund's adjuvant, including mice receiving PREVNAR 13®. Day 49 sera from each group were employed for ELISAs on plates coated with *S. pneumoniae* serotypes 8, 9V and 14. As mentioned above, serotypes 9V and 14 are included in PREVNAR 13® and elevated IgG response could be seen in PREVNAR 13® immunized mice against these two serotypes 49 days post vaccination (FIG. 13). Mice receiving the monovalent CPS14-ComP bioconjugate also showed significant IgG increase specific to serotype 14 (FIG. 12 and FIG. 13). Mice receiving the trivalent CPS8/CPS9V/CPS14-ComP bioconjugate also had statistically significant increases in serotype specific IgG responses 49 days post vaccination (FIG. 13).

Immunizations were conducted at the Southern Alberta Cancer Research Institute (SACRI) antibody services. For the CPS14 ComP monovalent immunizations, 4-6 weeks old female BALB/c mice were injected with 100 μL of purified protein/glycoprotein (3 μg total protein) with 50 μl of Freund's adjuvant. Two groups of mice (n=10) were injected either unglycosylated ComP (placebo) or CPS-ComP conjugate. Sera from the mice were obtained before immunizations and 7, 21, 35 and 49 days post immunizations. Booster doses were given on days 14 and 28. The same procedure was followed for the trivalent immunization, except four groups of mice (n=10) were used for the four different immunization groups. These groups were injected with 100 μL containing 3 μg of unconjugated ComP (placebo) and Freund's adjuvant, 100 μL containing 3 μg of ComP-CPS14 conjugate and Freund's adjuvant, 100 μL containing 9 μg of a glycoprotein mixture (ComP-CPS8, ComP-CPS9V and ComP-CPS14) and Freund's adjuvant, or 100 μl of a 1:3 diluted stock of PREVNAR 13® and Freund's adjuvant. CPS-ComP bioconjugates were formulated by total protein for this immunization.

Because Freund's adjuvant is not a suitable adjuvant for human clinical development, another immunization trial was performed with vaccines containing formulated with Imject Alum Adjuvant, a mild adjuvant containing a mixture of aluminum hydroxide and magnesium hydroxide. Vaccination cohorts included a buffer/adjuvant test group, a PREVNAR 13® test group, and a trivalent CPS8-/CPS9V-/CPS14-ComP bioconjugate test group. Groups of three mice were vaccinated on days 1, 14, and 28. Serum was collected on day 42 and used to determine effector functions via an opsonophagocytosis assay (OPA). Given the limited amounts of sera collected from individual mice, sera were tested for bactericidal activity against serotypes 8 and 14, as one serotype is included in PREVNAR 13® (serotype 14) and one is not (serotype 8). As seen in FIGS. 23A and 23B, serum from a representative mouse vaccinated with the trivalent CPS8-/CPS9V-/CPS14-ComP bioconjugate had increased bactericidal activity against S. pneumoniae serotype 14 strain when compared to sera from a mock vaccinated mouse. Importantly, that same bioconjugate vaccinated serum had high bactericidal activity against a S. pneumoniae serotype 8 strain, which was not observed for PREVNAR 13® vaccinated sera due to the absence of this conjugate in its formulation.

Another trivalent immunization experiment was conducted with groups of three 4-6 week old female BALB/c mice. Each immunization group was subcutaneously injected with 100 μL of a 1:1 immunogen (3 μg of protein of each of the trivalent bioconjugate or a 1:10 diluted stock of PREVNAR 13®) to Imject Alum Adjuvant. Mice were vaccinated on day 0, 14, and 28 and then sacrificed on day 42 for sera collection.

Another immunization experiment was conducted with groups of three 4-6 week old BALB/c mice (five female and five male per group). Mice were immunized subcutaneously with 100 μl of EPA (5 μg total protein), 100 μl of ComP-CPS8 (5 μg total polysaccharide), or 100 μl of EPA-CPS8 (0.1 μg total polysaccharide) on day 0, 14, and 28 and then sacrificed on day 42 for sera collection. Vaccines were formulated 1:1 with Imject Alum Adjuvant.

Glycoengineering a Pneumococcal Bioconjugate with a Conventional Vaccine Carrier.

Up to this point, the use of ComP from A. baylyi ADP1 has been exploited as a carrier protein for pneumococcal bioconjugate vaccine production. To increase the commercial applicability of this technology, however, a conventional vaccine carrier was sought to be compatible with the O-linked OTase. Chimeric fusion proteins were generated consisting of the 4E553 variant of Exotoxin A from Pseudomonas aeruginosa (EPA) C-terminally fused to a ComP fragment lacking its first 28 amino acids (ComPΔ28). A ComP ortholog from A. soli strain 110264 was used as it was most efficiently glycosylated by PglS and also found to be glycosylated at the same conserved serine as ComP from A. baylyi ADP1. The EPA fusion was linked to ComPΔ28 with a glycine-glycine-glycine-serine (GGGS; SEQ ID NO: 23) linker and trafficked to the periplasm with a DsbA signal sequence.

Because current formulations of pneumococcal conjugate vaccines do not contain a conjugate for serotype 8, focus was placed on generating an EPA-CPS8 pneumococcal bioconjugate. The EPA fusion was introduced into SDB1 cells co-expressing PglS and CPS8, subsequently purified, and then probed for glycosylation. The EPA fusion was efficiently glycosylated with CPS8. Furthermore, mass spectrometry analysis of intact glycoproteins confirmed that the EPA fusion was repetitively modified with an increasing mass unit of 662 Da, which is the calculated mass of a single CPS8 subunit. The EPA fusion was found to be glycosylated with at least 11 CPS8 subunits by intact protein analysis; however, western blot and Coomassie analyses indicated that >15 subunits were able to be transferred.

Subsequently, a vaccination experiment was performed comparing the immunogenicity of an EPA-CPS8 pneumococcal bioconjugate to a ComP-CPS8 pneumococcal bioconjugate. Groups of 10 mice were either vaccinated with 5 μg of EPA alone (based on total protein), 5 μg of ComP-CPS8 (based on polysaccharide as determined by anthrone sulfuric acid), or 100 ng of EPA-CPS8 (based on polysaccharide as determined by mass spectrometry of intact EPA-CPS8). Mice were vaccinated on days 1, 14, and 28 with serum collected on day 42. All vaccinates were formulated 1:1 with Imject Alum Adjuvant. ELISAs were subsequently performed to determine the IgG titers specific to CPS8. As seen in FIG. 25A, mice vaccinated with either ComP-CPS8 or EPA-CPS8 has statistically significant increases in IgG titers specific to CPS8 when compared to EPA vaccinated mice. Additionally, the protective capacity of sera from vaccinated mice was determined using a murine adapted opsonophagocytosis assay (OPA) with whole blood leukocytes. As shown in FIG. 25B, sera from vaccinated mice immunized with ComP-CPS8 displayed high levels of bactericidal killing ranging from 84-50% with one mouse not displaying any killing activity. Moreover, sera from EPA-CPS8 vaccinated mice also displayed bactericidal ranging from 88%-10% with three mice displaying no killing activity. Expectedly, sera from EPA vaccinate mice did not display killing activity.

Enzyme Linked Immunosorbent Assays (ELISAs).

S. pneumoniae strains grown overnight in BHI broth at 37° C. in 5% $CO_2$ were washed in PBS and the optical density was adjusted to $OD_{600}$=0.6 units. Cells were heat inactivated at 60° C. for 2-4 hours followed by immobilization on high binding 96 well plates (Corning) by adding 50 μL/well. Plates were incubated on a tumbler overnight at 4° C. The following day, wells were washed three times with PBST (Phosphate buffered saline-tween) (100 μL/well) before blocking with 5% skimmed milk (250 μL/well) for 2 h. The wells were washed three times with PBST. Plates were incubated for an 1 hour at room temperature with mouse sera (100 μL/well) at a 1:500 dilution in 2.5% skimmed milk in PBST. For the positive control, commercial rabbit polyclonal antibodies against CPS were used (Statens serum institute). Negative control wells were treated with skimmed milk without any primary antibody. After incubation with the primary antibody, wells were washed three times with PBST followed by a one hour incubation with secondary HRP-conjugated antibodies (100 μL/well) diluted in 2.5% skimmed milk in PBST. After incubation, the wells were washed three times with PBST and 100 μL of the chromogenic substrate TMB (Cell Signaling Technology) was added to each well. Plates were incubated at room temperature for 5 minutes after which the absorbance at 650 nm was measured using a BioTek™ plate reader.

For IgG titer determinations, ELISA plates were coated with 100 µL of 1×10$^8$ CFU/mL of *S. pneumoniae* serotype 8 grown approximately to mid-log phase. Bacteria were washed twice in PBS and suspended in water prior to coating. ELISA plates were allowed to air dry in a biological hood for 24 hours. Fifty microliters of methanol were then added to each well and allowed to air dry. Plates were stored in a re-sealable bag protected from the light until use. To perform the titration of mouse total IgG antibodies, day 42 sera was serially diluted (2-fold) in PBST and antibodies were detected using an anti-mouse, HRP-linked IgG (Cell Signaling Technology #7076) diluted 1:4000. For mouse serum titrations, the reciprocal of the last serum dilution that resulted in an optical density at 450 nm equal to or lower than 0.2 was considered the titer of that serum. For representation purposes, negative titers (less than or equal to the cutoff) were given an arbitrary titer value of 10. Inter-plate variations were controlled by including an internal reference positive control on each plate. This control was hyper-immune sera from a mouse previously immunized with the ComP-CPS8 bioconjugate vaccine. The ELISA reactions in TMB were stopped when an OD450 nm of ~1 was obtained for the internal positive control.

Site Directed Mutagenesis.

Site-directed mutagenesis was carried out to mutate the residues H325 in PglM and S82 and S84 of ComP as previously described (Fisher and Pei, 1997). Mutagenic primers were designed using Primer X, a web-based primer design program (http://www.bioinformatics.org/primerx/). Primers used are listed in Supplementary Table 1. PCR reactions were performed using Pfu polymerase and 2-10 ng of pMN2 as template. The PCR reaction consisted of an initial denaturation of 30 s at 95° C. followed by 16 cycles of 30 s at 95° C., 60 s at 55° C., 360 s at 68° C. with no final extension. PCR reactions were DpnI digested for 2 hours to remove the template plasmid, then transformed into electrocompetent DH5α cells and grown on ampicillin for plasmid selection. Colonies were sequenced to confirm mutagenesis.

Digestion of ComP-CPS14 Conjugate.

Isolated ComP bands were processed as previously described with minor modification. Briefly, gel separated ComP bands were excised and destained in a 50:50 solution of 50 mM NH$_4$HCO$_3$: 100% ethanol for 20 minutes at room temperature with shaking at 750 rpm. Destained bands were then washed with 100% ethanol, vacuum-dried for 20 minutes and rehydrated in 10 mM DTT in 50 mM NH$_4$HCO$_3$. Reduction was carried out for 60 minutes at 56° C. with shaking. The reducing buffer was then removed and the gel bands washed twice in 100% ethanol for 10 minutes to ensure the removal of remaining DTT. Reduced ethanol washed samples were sequentially alkylated with 55 mM Iodoacetamide in 50 mM NH$_4$HCO$_3$ in the dark for 45 minutes at RT. Alkylated samples were then washed with 2 rounds of Milli-Q water and 100% ethanol then vacuum-dried. Alkylated samples were then rehydrated with 10 ng µl$^{-1}$ GluC (Promega, Madison WI) in 40 mM NH$_4$HCO$_3$ at 4° C. for 1 hr. Excess GluC was removed, gel pieces were covered in 40 mM NH$_4$HCO$_3$ and incubated for 24 hours at 37° C. Peptides were concentrated and desalted using C$_{18}$ stage tips (Ishihama, Y., Rappsilber, J. & Mann, M. *J Proteome Res* 5, 988-994 (2006); Rappsilber, J., Mann, M. & Ishihama, Y. *Nature protocols* 2, 1896-1906 (2007)) and stored on tip at 4° C. Peptides were eluted in buffer B (0.5% acetic acid, 80% MeCN) and dried before analysis by LC-MS.

Identification of Glycopeptides Using Reversed Phase LC-MS and HCD MS-MS.

Purified peptides were re-suspended in Buffer A* and separated using an in-house packaged 25 cm, 75 µm inner diameter, 360 µm outer diameter, 1.7 um 130 Å CSH C$_{18}$ (Waters, Manchester, UK) reverse phase analytical column with an integrated HF etched nESI tip. Samples were loaded directly onto the column using an ACQUITY UPLC M-Class System (Waters) at 600 nl/min for 20 minutes with Buffer A (0.1% FA) and eluted at 300 nl/min using a gradient altering the concentration of Buffer B (99.9% ACN, 0.1% FA) from 2% to 32% B over 60 minutes, then from 32% to 40% B in the next 10 minutes, then increased to 80% B over 8 minutes period, held at 100% B for 2 minutes, and then dropped to 2% B for another 10 minutes. RP separated peptides were infused into a Q-EXACTIVE (Thermo Scientific) mass spectrometer and data acquired using data dependent acquisition. Two methods were used to identify putative glycopeptides. Method A aimed to enable robust peptide identification in which one full precursor scan (resolution 70,000; 350-1850 m/z, AGC target of 1×10$^6$) was followed by 10 data-dependent HCD MS-MS events (resolution 35 k AGC target of 1×10$^5$ with a maximum injection time of 110 ms, NCE 26 with 25% stepping) with 90 seconds dynamic exclusion enabled. Method B aimed to enable more complete characterization of glycans within glycopeptides with one full precursor scan (resolution 70,000; 350-1850 m/z, AGC target of 1×10$^6$) followed by 10 data-dependent HCD MS-MS events (resolution 35 k AGC target of 5×10$^5$ with a maximum injection time of 250 ms, NCE 13 with 25% stepping) with 90 seconds dynamic exclusion enabled.

Database Interrogation of Identified Glycopeptides.

Raw files were processed manually to identify potential glycopeptides based on the diagnostic oxonium 204.08 m/z ion. Putative glycopeptide derived scans were manually inspected and identified as possible GluC derived ComP glycopeptides based on the presence of an intense deglycosylated ComP derived peptide ion, matching within 10 ppm using the Expasy FindPept tool (on the world wide web at web.expasy.org/findpept/). To facilitate peptide assignments the resulting glycopeptides was manually annotated according to (Roepstorff, P. & Fohlman, J. *Biomed Mass Spectrom* 11, 601 (1984)) with the aid of the Protein Prospector tool MS-Product (on the world wide web at prospector.ucsf.edu/prospector/cgi-bin/msform.cgi?form=msproduct).

Intact Protein Analysis.

Intact analysis was performed using a 6520 Accurate mass Q-TOF mass spectrometer (Agilent, Santa Clara, CA). Protein samples were re-suspended in 2% acetonitrile, 0.1% TFA and immediately loaded onto a C5 Jupiter 5 µm 300 Å 50 mm*2.1 mm column (Phenomenex, Torrance, CA) Using an Agilent 1200. Samples were desalted by washing with buffer A (2% acetonitrile, 0.1% formic acid) for 4 minutes and then separated with a 12 min linear gradient from 2 to 100% buffer B (80% acetonitrile, 0.1% formic acid) at a flow rate of 0.200 ml/min. MS1 Mass spectra were acquired at 1 Hz between a mass range of 300-3,000 m/z. Intact mass analysis and deconvolution was performed using MassHunter B.06.00 (Agilent).

Opsonophagocytosis Assay (OPA).

Assays were performed as previously described (;) 47,48 and are briefly described below. Blood collection. Blood was collected by intracardiac puncture from naïve female mice (Charles River, Wilmington, MA), treated with sodium heparin, then diluted to obtain 6.25×10$^6$ leukocytes/mL in RPMI 1640 supplemented with 5% heat-inactivated fetal bovine serum, 10 mM HEPES, 2 mM L-glutamine and 50 µM 2-mercaptoethanol. All reagents were from Gibco (Invitrogen, Burlington, ON, Canada). Bacterial suspension preparation. Isolated colonies on sheep blood agar plates of either *S. pneumoniae* serotypes 8 or 14 (Statens Serum Institut, Denmark) were inoculated in 5 ml of Todd-Hewitt Broth (THB) (Oxoid, Thermo Fisher Scientific, Nepean, Canada) and incubated for 16 hours at 37° C. with 5% $CO_2$. Working cultures were prepared by transferring 0.1 mL of 16 h-cultures into 10 mL of THB, which was then incubated for 5 hours. Bacteria were washed 3 times and resuspended in PBS to obtain an OD600 value of 0.6, which corresponds to $1.5 \times 10^8$ and colony forming units (CFU)/mL and to $3.5 \times 10^8$ CFU/mL for serotype 8 and serotype 14, respectively. Final bacterial suspensions were prepared in complete cell culture medium to obtain a concentration of $6.25 \times 10^4$ CFU/mL. The number of CFU/mL in the final suspensions was determined by plating samples onto Todd-Hewitt Agar (THA). Opsonophagocytosis Assay. Diluted whole blood ($5 \times 10^5$ total leukocytes) was mixed with $5 \times 10^3$ CFU of *S. pneumoniae* serotype 8 or 14 (MOI of 0.01) and 5% (v/v) of serum from control (placebo) or vaccinated mice in a microtube to a final volume of 0.2 mL. Microtubes were incubated for 4 hours at 37° C. with 5% $CO_2$, with shaking. After incubation, viable bacterial counts were performed on THA. Tubes with the addition of naïve mouse sera (5% v/v) or of commercial rabbit anti-*S. pneumoniae* types 8 or 14 serum (5% v/v) (Statens Serum Institut, Denmark), were used as negative and positive controls, respectively. The percent of bacteria killing was determined using the following formula: percent bacteria killed=[1−(bacteria recovered from sample tubes/bacteria recovered from negative control tubes with naïve sera)]×100.

TABLE 2

Primers.

| Primer | Sequence |
|---|---|
| igrF | ACTGGTCGACTAGTAGTACTATATGGCTTTAAA (SEQ ID NO: 25) |
| igrR | ACTGCTGCAGTTAATATTCTATTGAACAAAATTTTAAC (SEQ ID NO: 26) |
| H325A F | GAGAATGGTTTACATACTCAGCGAATTTGTTCTTAGATTTA ATG (SEQ ID NO: 27) |
| H325A R | CATTAAATCTAAGAACAAATTCGCTGAGTATGTAAACCATT CTC (SEQ ID NO: 28) |
| S82A F-ADP1 | GGAGTCCAAGAAATTGCGGCAAGTAATGCCA (SEQ ID NO: 29) |
| S82A R-ADP1 | GTGGCATTACTTGCCGCAATTTCTTGGACTCC (SEQ ID NO: 30) |
| S84A F-ADP1 | CAAGAAATTTCAGCAGCGAATGCCACTACGAAC (SEQ ID NO: 31) |
| S84A R-ADP1 | GTTCGTAGTGGCATTCGCTGCTGAAATTTCTTG (SEQ ID NO: 32) |
| S82A 110254 F | ACAGATCGCGTCCGGCGCCGCAGCAGCGACAACAAATGTAG CGT (SEQ ID NO: 33) |
| S82A 110254 R | ACGCTACATTTGTTGTCGCTGCTGCGGCGCCGGACGCGATC TGT (SEQ ID NO: 34) |
| S84A 110254 F | CGGGCGTCACACAGATCGCGGCCGGCGCCTCAGCAGCGACA ACA (SEQ ID NO: 35) |

TABLE 2-continued

Primers.

| Primer | Sequence |
|---|---|
| S84A 110254 R | TGTTGTCGCTGCTGAGGCGCCGGCCGCGATCTGTGTGACGC CCG (SEQ ID NO: 36) |

TABLE 3

Glycosylation Tag Sequences $X_1X_2GTX_5X_6X_7X_8X_9X_{10}X_{11}X_{12}CX_{14}GVX_{17}X_{18}IX_{20}X_{21}X_{22}ASX_{25}X_{26}TX_{28}$
$NVX_{31}X_{32}AX_{34}CX_{36}X_{37}X_{38}X_{39}X_{40}X_{41}X_{42}X_{43}X_{44}X_{45}X_{46}$
(SEQ ID NO: 37)
Wherein:
$X_1$ is V, A, or no amino acid;
$X_2$ is A, G, T, or no amino acid;
$X_5$ is P, S, or Q;
$X_6$ is S, M, or I;
$X_7$ is T, P, or V;
$X_8$ is A, S, or T;
$X_9$ is G, N, S, or T;
$X_{10}$ is N or no amino acid;
$X_{11}$ is S, G, or A;
$X_{12}$ is S or N;
$X_{14}$ is V, T, or A;
$X_{17}$ is Q, T, or E;
$X_{18}$ is E, Q, or T;
$X_{20}$ is S, N, A, or G;
$X_{21}$ is S or no amino acid;
$X_{22}$ is G or no amino acid;
$X_{25}$ is N, S, or A;
$X_{26}$ is A, S, or K;
$X_{28}$ is T, S, or K;
$X_{31}$ is A or E;
$X_{32}$ is T or S;
$X_{34}$ is T, Q, or A;
$X_{36}$ is G, S, or T;
$X_{37}$ is A, G, or D;
$X_{38}$ is S, L, or A;
$X_{39}$ is S, G, D, or T;
$X_{40}$ is A, V, or G;
$X_{41}$ is G, I, or V;
$X_{42}$ is Q, T, or I;
$X_{43}$ is I, V, T, or L;
$X_{44}$ is I, T, or V;
$X_{45}$ is M or no amino acid; and
$X_{46}$ is D or no amino acid.

$CX_{14}GVX_{17}X_{18}IX_{20}X_{21}X_{22}ASX_{25}X_{26}TX_{28}NVX_{31}X_{32}AX_{34}C$
(SEQ ID NO: 45)

$X_{14}GVX_{17}X_{18}IX_{20}X_{21}X_{22}ASX_{25}X_{26}TX_{28}NVX_{31}X_{32}AX_{34}$
(SEQ ID NO: 38)
Wherein:
$X_{14}$ is V, T, or A, optionally V;
$X_{17}$ is Q, T, or E, optionally Q;
$X_{18}$ is E, Q, or T;
$X_{20}$ is S, N, A, or G;
$X_{21}$ is S or no amino acid;
$X_{22}$ is G or no amino acid;
$X_{25}$ is N, S, or A, optionally N;
$X_{26}$ is A, S, or K, optionally A;
$X_{28}$ is T, S, or K;
$X_{31}$ is A or E, optionally A;
$X_{32}$ is T or S, optionally T; or
$X_{34}$ is T, Q, or A, optionally T.

The present disclosure is not to be limited in scope by the specific aspects described or preceding Examples which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

REFERENCES

1. O'Brien, K. L. et al. Burden of disease caused by *Streptococcus pneumoniae* in children younger than 5 years: global estimates. Lancet 374, 893-902, doi: 10.1016/50140-6736(09)61204-6 (2009).
2. Pneumococcal conjugate vaccine for childhood immunization—WHO position paper. Wkly Epidemiol Rec 82, 93-104 (2007).
3. Prevention, C. f. D. C. a. Pneumococcal Vaccination, <https://www.cdc.gov/vaccines/vpd/pneumo/index.html>
4. Pace, D. Glycoconjugate vaccines. Expert Opin Biol Ther 13, 11-33, doi:10.1517/14712598.2012.725718 (2013).
5. Vella, M. & Pace, D. Glycoconjugate vaccines: an update. Expert Opin Biol Ther 15, 529-546, doi:10.1517/14712598.2015.993375 (2015).
6. Pollard, A. J., Perrett, K. P. & Beverley, P. C. Maintaining protection against invasive bacteria with protein-polysaccharide conjugate vaccines. Nat Rev Immunol 9, 213-220, doi:10.1038/nri2494 (2009).
7. Avci, F. Y., Li, X., Tsuji, M. & Kasper, D. L. A mechanism for glycoconjugate vaccine activation of the adaptive immune system and its implications for vaccine design. Nat Med 17, 1602-1609, doi:10.1038/nm.2535 (2011).
8. Package Insert—Prevnar 13—FDA, <https://www.fda.gov/downloads/BiologicsBloodVaccines/Vaccines/ApprovedProducts/UCM201669.pdf>
9. Prevention, C. f. D. C. a. Vaccines for Children Program (VFC), <https://www.cdc.gov/vaccines/programs/vfc/awardees/vaccine-management/price-list/index.html> (2018).
10. Pfizer Inc. 2017 Financial Report, <https://www.sec.gov/Archives/edgar/data/78003/000007800318000027/pfe-exhibit13x12312017x10k.htm> (2018).
11. Frasch, C. E. Preparation of bacterial polysaccharide-protein conjugates: analytical and manufacturing challenges. Vaccine 27, 6468-6470, doi:10.1016/j.vaccine.2009.06.013 (2009).
12. Huttner, A. & Gambillara, V. The development and early clinical testing of the ExPEC4V conjugate vaccine against uropathogenic *Escherichia coli*. Clin Microbiol Infect, doi:10.1016/j.cmi.2018.05.009 (2018).
13. Huttner, A. et al. Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial. Lancet Infect Dis 17, 528-537, doi:10.1016/S1473-3099(17)30108-1 (2017).
14. Riddle, M. S. et al. Safety and Immunogenicity of a Candidate Bioconjugate Vaccine against *Shigella flexneri* 2a Administered to Healthy Adults: a Single-Blind, Randomized Phase I Study. Clin Vaccine Immunol 23, 908-917, doi:10.1128/CVI.00224-16 (2016).
15. Apweiler, R., Hermjakob, H. & Sharon, N. On the frequency of protein glycosylation, as deduced from analysis of the SWISS-PROT database. Biochim Biophys Acta 1473, 4-8 (1999).
16. Nothaft, H. & Szymanski, C. M. Protein glycosylation in bacteria: sweeter than ever. Nat Rev Microbiol 8, 765-778, doi:10.1038/nrmicro2383 (2010).
17. Iwashkiw, J. A., Vozza, N. F., Kinsella, R. L. & Feldman, M. F. Pour some sugar on it: the expanding world of bacterial protein O-linked glycosylation. Mol Microbiol 89, 14-28, doi:10.1111/mmi.12265 (2013).
18. Ciocchini, A. E. et al. A bacterial engineered glycoprotein as a novel antigen for diagnosis of bovine brucellosis. Vet Microbiol 172, 455-465, doi:10.1016/j.vetmic.2014.04.014 (2014).
19. Garcia-Quintanilla, F., Iwashkiw, J. A., Price, N. L., Stratilo, C. & Feldman, M. F. Production of a recombinant vaccine candidate against *Burkholderia pseudomallei* exploiting the bacterial N-glycosylation machinery. Front Microbiol 5, 381, doi:10.3389/fmicb.2014.00381 (2014).
20. Iwashkiw, J. A. et al. Exploiting the *Campylobacter jejuni* protein glycosylation system for glycoengineering vaccines and diagnostic tools directed against brucellosis. Microb Cell Fact 11, 13, doi:10.1186/1475-2859-11-13 (2012).
21. Wacker, M. et al. Substrate specificity of bacterial oligosaccharyltransferase suggests a common transfer mechanism for the bacterial and eukaryotic systems. Proc Natl Acad Sci USA 103, 7088-7093, doi:10.1073/pnas.0509207103 (2006).
22. Feldman, M. F. et al. Engineering N-linked protein glycosylation with diverse O antigen lipopolysaccharide structures in *Escherichia coli*. Proc Natl Acad Sci USA 102, 3016-3021, doi:10.1073/pnas.0500044102 (2005).
23. Faridmoayer, A., Fentabil, M. A., Mills, D. C., Klassen, J. S. & Feldman, M. F. Functional characterization of bacterial oligosaccharyltransferases involved in O-linked protein glycosylation. J Bacteriol 189, 8088-8098, doi: 10.1128/JB.01318-07 (2007).
24. Geno, K. A. et al. Pneumococcal Capsules and Their Types: Past, Present, and Future. Clin Microbiol Rev 28, 871-899, doi:10.1128/CMR.00024-15 (2015).
25. Ihssen, J. et al. Increased efficiency of *Campylobacter jejuni* N-oligosaccharyltransferase PglB by structure-guided engineering. Open Biol 5, 140227, doi:10.1098/rsob.140227 (2015).
26. Pan, C. et al. Biosynthesis of Conjugate Vaccines Using an O-Linked Glycosylation System. MBio 7, e00443-00416, doi:10.1128/mBio.00443-16 (2016).
27. Wacker, M. et al. N-linked glycosylation in *Campylobacter jejuni* and its functional transfer into *E. coli*. Science 298, 1790-1793, doi:10.1126/science.298.5599.1790 (2002).
28. Vik, A. et al. Broad spectrum O-linked protein glycosylation in the human pathogen *Neisseria gonorrhoeae*. Proc Natl Acad Sci USA 106, 4447-4452, doi:10.1073/pnas.0809504106 (2009).
29. Harding, C. M. et al. *Acinetobacter* strains carry two functional oligosaccharyltransferases, one devoted exclusively to type IV pilin, and the other one dedicated to O-glycosylation of multiple proteins. Mol Microbiol 96, 1023-1041, doi:10.1111/mmi.12986 (2015).
30. Pan, Y. J. et al. Genetic analysis of capsular polysaccharide synthesis gene clusters in 79 capsular types of *Klebsiella* spp. Sci Rep 5, 15573, doi:10.1038/srep15573 (2015).

31. Kovach, M. E. et al. Four new derivatives of the broad-host-range cloning vector pBBR1MCS, carrying different antibiotic-resistance cassettes. Gene 166, 175-176 (1995).
32. Wu, K. M. et al. Genome sequencing and comparative analysis of *Klebsiella pneumoniae* NTUH-K2044, a strain causing liver abscess and meningitis. J Bacteriol 191, 4492-4501, doi:10.1128/JB.00315-09 (2009).
33. Lery, L. M. et al. Comparative analysis of *Klebsiella pneumoniae* genomes identifies a phospholipase D family protein as a novel virulence factor. BMC Biol 12, 41, doi:10.1186/1741-7007-12-41 (2014).
34. Dykxhoorn, D. M., St Pierre, R. & Linn, T. A set of compatible tac promoter expression vectors. Gene 177, 133-136 (1996).
35. Arakawa, Y. et al. Biosynthesis of *Klebsiella* K2 capsular polysaccharide in *Escherichia coli* HB101 requires the functions of rmpA and the chromosomal cps gene cluster of the virulent strain *Klebsiella pneumoniae* Chedid (O1:K2). Infect Immun 59, 2043-2050 (1991).
36. Yeh, K. M. et al. Capsular serotype K1 or K2, rather than magA and rmpA, is a major virulence determinant for *Klebsiella pneumoniae* liver abscess in Singapore and Taiwan. J Clin Microbiol 45, 466-471, doi:10.1128/JCM.01150-06 (2007).
37. Kowarik, M. et al. Definition of the bacterial N-glycosylation site consensus sequence. EMBO J 25, 1957-1966, doi:10.1038/sj.emboj.7601087 (2006).
38. Comer, J. E., Marshall, M. A., Blanch, V. J., Deal, C. D. & Castric, P. Identification of the *Pseudomonas aeruginosa* 1244 pilin glycosylation site. Infect Immun 70, 2837-2845 (2002).
39. Scott, N. E. et al. Diversity within the O-linked protein glycosylation systems of *acinetobacter* species. Mol Cell Proteomics 13, 2354-2370, doi:10.1074/mcp.M114.038315 (2014).
40. Schwarz, F. et al. A combined method for producing homogeneous glycoproteins with eukaryotic N-glycosylation. Nat Chem Biol 6, 264-266, doi:10.1038/nchembio.314 (2010).
41. Porstendorfer, D., Drotschmann, U. & Averhoff, B. A novel competence gene, comP, is essential for natural transformation of *Acinetobacter* sp. strain BD413. Appl Environ Microbiol 63, 4150-4157 (1997).
42. Giltner, C. L., Nguyen, Y. & Burrows, L. L. Type IV pilin proteins: versatile molecular modules. Microbiol Mol Biol Rev 76, 740-772, doi:10.1128/MMBR.00035-12 (2012).
43. Pelicic, V. Type IV pili: e pluribus unum? Mol Microbiol 68, 827-837, doi:10.1111/j.1365-2958.2008.06197.x (2008).
44. Malik, A. Protein fusion tags for efficient expression and purification of recombinant proteins in the periplasmic space of *E. coli*. 3 Biotech 6, 44, doi:10.1007/s13205-016-0397-7 (2016).
45. Ravenscroft, N. et al. Purification and characterization of a *Shigella* conjugate vaccine, produced by glycoengineering *Escherichia coli*. Glycobiology 26, 51-62, doi:10.1093/glycob/cwv077 (2016).
46. Schulz, B. L. et al. Identification of bacterial protein O-oligosaccharyltransferases and their glycoprotein substrates. PLoS One 8, e62768, doi:10.1371/journal.pone.0062768 (2013).
47. Castric, P. pilO, a gene required for glycosylation of *Pseudomonas aeruginosa* 1244 pilin. Microbiology 141 (Pt 5), 1247-1254, doi:10.1099/13500872-141-5-1247 (1995).
48. Power, P. M. et al. Genetic characterization of pilin glycosylation and phase variation in *Neisseria meningitidis*. Mol Microbiol 49, 833-847 (2003).
49. Stimson, E. et al. Meningococcal pilin: a glycoprotein substituted with digalactosyl 2,4-diacetamido-2,4,6-trideoxyhexose. Mol Microbiol 17, 1201-1214 (1995).
50. Ishihama, Y., Rappsilber, J. & Mann, M. Modular stop and go extraction tips with stacked disks for parallel and multidimensional Peptide fractionation in proteomics. J Proteome Res 5, 988-994, doi:10.1021/pr050385q (2006).
51. Rappsilber, J., Mann, M. & Ishihama, Y. Protocol for micro-purification, enrichment, pre-fractionation and storage of peptides for proteomics using StageTips. Nature protocols 2, 1896-1906, doi:10.1038/nprot.2007.261 (2007).
52. Roepstorff, P. & Fohlman, J. Proposal for a common nomenclature for sequence ions in mass spectra of peptides. Biomed Mass Spectrom 11, 601, doi:10.1002/bms.1200111109 (1984).
53. Haurat, M. F. et al. Selective sorting of cargo proteins into bacterial membrane vesicles. J Biol Chem 286, 1269-1276, doi:10.1074/jbc.M110.185744 (2011).
54. Price, N. L. et al. Glycoengineered Outer Membrane Vesicles: A Novel Platform for Bacterial Vaccines. Sci Rep 6, 24931, doi:10.1038/srep24931 (2016).
55. Kay, E. J., Yates, L. E., Terra, V. S., Cuccui, J. & Wren, B. W. Recombinant expression of *Streptococcus pneumoniae* capsular polysaccharides in *Escherichia coli*. Open Biol 6, 150243, doi:10.1098/rsob.150243 (2016).

What is claimed is:

1. A bioconjugate comprising an oligo- or polysaccharide covalently linked to a fusion protein,
   wherein the fusion protein comprises a ComP protein (ComP) glycosylation tag fragment,
   wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and a variant of any thereof having one or two amino acid substitutions, one or two amino acid additions, and/or one or two amino acid deletions, wherein the variant maintains the serine residue corresponding to the conserved serine residue at position 82 of SEQ ID NO: 2 (ComP$_{110264}$: ENV58402.1),
   wherein the ComP glycosylation tag fragment is not more than 50 amino acids in length, and
   wherein the fusion protein is glycosylated with the oligo- or polysaccharide on the ComP glycosylation tag fragment at the serine residue corresponding to the conserved serine residue at position 82 of SEQ ID NO: 2 (ComP$_{110264}$: ENV58402.1).

2. The bioconjugate of claim 1, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and a variant of any thereof having one or two amino acid substitutions, wherein the variant maintains the serine residue corresponding to the conserved serine residue at position 82 of SEQ ID NO: 2 (ComP$_{110264}$: ENV58402.1).

3. The bioconjugate of claim 1, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and a variant of any thereof having one or two amino acid additions, wherein the variant maintains the serine residue corresponding to the conserved serine residue at position 82 of SEQ ID NO: 2 (ComP$_{110264}$: ENV58402.1).

4. The bioconjugate of claim 1, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and a variant of any thereof having one or two amino acid deletions, wherein the variant maintains the serine residue corresponding to the conserved serine residue at position 82 of SEQ ID NO: 2 (ComP$_{110264}$: ENV58402.1).

5. The bioconjugate of claim 1, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), and a variant of any thereof having one or two amino acid substitutions, one or two amino acid additions, and/or one or two amino acid deletions, wherein the variant maintains the serine residue corresponding to the conserved serine residue at position 82 of SEQ ID NO: 2 (COMP$_{110264}$: ENV58402.1).

6. The bioconjugate of claim 1, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), and a variant of any thereof having one or two amino acid substitutions, wherein the variant maintains the serine residue corresponding to the conserved serine residue at position 82 of SEQ ID NO: 2 (ComP$_{110264}$: ENV58402.1).

7. The bioconjugate of claim 1, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), and a variant of any thereof having one or two amino acid additions, wherein the variant maintains the serine residue corresponding to the conserved serine residue at position 82 of SEQ ID NO: 2 (ComP$_{110264}$: ENV58402.1).

8. The bioconjugate of claim 1, wherein the ComP glycosylation tag fragment comprises an amino acid sequence selected from the group consisting of VGVQEISASNATTNVATAT (SEQ ID NO: 39), TGVTQIASGASAATTN- VASAQ (SEQ ID NO: 40), and a variant of any thereof having one or two amino acid deletions, wherein the variant maintains the serine residue corresponding to the conserved serine residue at position 82 of SEQ ID NO: 2 (ComP$_{110264}$: ENV58402.1).

9. The bioconjugate of claim 1, wherein the oligo- or polysaccharide is a capsular polysaccharide produced by a bacterium from the genus *Streptococcus*.

10. The bioconjugate of claim 9, wherein the capsular polysaccharide is CPS14, CPS8, CPS9V, or CPS15b.

11. The bioconjugate of claim 1, wherein the oligo- or polysaccharide is produced by a bacterium from the genus *Klebsiella*.

12. The bioconjugate of claim 1, wherein the polysaccharide is a *Klebsiella pneumoniae* capsular polysaccharide.

13. The bioconjugate of claim 1, wherein the oligo- or polysaccharide comprises a glucose at its reducing end.

14. The bioconjugate of claim 1, wherein the fusion protein comprises two or more ComP glycosylation tag fragments.

15. The bioconjugate of claim 1, wherein the bioconjugate is a conjugate vaccine.

16. The bioconjugate of claim 15, wherein when the conjugate vaccine is a vaccine against *Streptococcus pneumoniae* serotype 8.

17. A composition comprising the conjugate vaccine of claim 15 and an adjuvant.

18. A method of inducing a host immune response against a bacterial pathogen, the method comprising administering to a subject in need of the immune response an effective amount of the conjugate vaccine of claim 15.

19. A method of preventing or treating a bacterial disease and/or infection in a subject comprising administering to a subject in need thereof the conjugate vaccine of claim 15.

20. A method of producing a pneumococcal conjugate vaccine against pneumococcal infection, the method comprising:
    (a) isolating the conjugate vaccine of claim 15; and
    (b) combining the isolated conjugate vaccine with an adjuvant.

21. The bioconjugate of claim 1, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), and VGVQTIAASNATKNVATAT (SEQ ID NO: 43).

22. The bioconjugate of claim 1, wherein the ComP glycosylation tag fragment comprises the amino acid sequence VGVQEISASNATTNVATAT (SEQ ID NO: 39) or TGVTQIASGASAATTNVASAQ (SEQ ID NO: 40).

23. The bioconjugate of claim 22, wherein the oligo- or polysaccharide is a capsular polysaccharide produced by a bacterium from the genus *Streptococcus*.

24. The bioconjugate of claim 23, wherein the capsular polysaccharide is CPS14, CPS8, CPS9V, or CPS15b.

25. The bioconjugate of claim 22, wherein the oligo- or polysaccharide is produced by a bacterium from the genus *Klebsiella*.

26. The bioconjugate of claim 22, wherein the polysaccharide is a *Klebsiella pneumoniae* capsular polysaccharide.

27. A fusion protein comprising a ComP glycosylation tag fragment that comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and a variant of any thereof having one or two amino acid substitutions, one or two amino acid additions, and/or one or two amino acid deletions, wherein the variant maintains the serine residue corresponding to the conserved serine residue at position 82 of SEQ ID NO: 2 (ComP$_{110264}$: ENV58402.1),
    wherein the ComP glycosylation tag fragment comprises the serine residue corresponding to the conserved serine residue at position 82 of SEQ ID NO: 2 (ComP$_{110264}$: ENV58402.1), and
    wherein the ComP glycosylation tag fragment is not more than 50 amino acids in length.

28. The fusion protein of claim 27, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), and a variant of any thereof having one or two amino acid substitutions, one or two amino acid additions, and/or one or two amino acid deletions, wherein the variant maintains the serine residue corresponding to the conserved serine residue at position 82 of SEQ ID NO: 2 (ComP$_{110264}$: ENV58402.1).

29. The fusion protein of claim 27, wherein the ComP glycosylation tag fragment is attached to a heterologous carrier protein.

30. The fusion protein of claim 29, wherein the heterologous carrier protein is selected from the group consisting of diphtheria toxoid, CRM$_{197}$, tetanus toxoid, *Pseudomonas aeruginosa* Exotoxin A (EPA), tetanus toxin C fragment, cholera toxin B subunit, *Haemophilus influenza* protein D, and a fragment of any thereof.

31. The fusion protein of claim 27, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and a variant of any thereof having one or two amino acid substitutions, wherein the variant maintains the serine residue corresponding to the conserved serine residue at position 82 of SEQ ID NO: 2 (ComP$_{110264}$: ENV58402.1).

32. The fusion protein of claim 27, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and a variant of any thereof having one or two amino acid additions, wherein the variant maintains the serine residue corresponding to the conserved serine residue at position 82 of SEQ ID NO: 2 (ComP$_{110264}$: ENV58402.1).

33. The fusion protein of claim 27, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), VGVQTIAASNATKNVATAT (SEQ ID NO: 43), and a variant of any thereof having one or two amino acid deletions, wherein the variant maintains the serine residue corresponding to the conserved serine residue at position 82 of SEQ ID NO: 2 (ComP$_{110264}$: ENV58402.1).

34. The fusion protein of claim 27, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), and a variant of any thereof having one or two amino acid substitutions, wherein the variant maintains the serine residue corresponding to the conserved serine residue at position 82 of SEQ ID NO: 2 (ComP$_{110264}$: ENV58402.1).

35. The fusion protein of claim 27, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), and a variant of any thereof having one or two amino acid additions, wherein the variant maintains the serine residue corresponding to the conserved serine residue at position 82 of SEQ ID NO: 2 (ComP$_{110264}$: ENV58402.1).

36. The fusion protein of claim 27, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), and a variant of any thereof having one or two amino acid deletions, wherein the variant maintains the serine residue corresponding to the conserved serine residue at position 82 of SEQ ID NO: 2 (ComP$_{110264}$: ENV58402.1).

37. The fusion protein of claim 27, wherein the ComP glycosylation tag fragment is covalently linked to an oligo- or polysaccharide at the serine residue corresponding to the conserved serine residue at position 82 of SEQ ID NO: 2 (ComP$_{110264}$: ENV58402.1).

38. The fusion protein of claim 37, wherein the oligo- or polysaccharide is a capsular polysaccharide produced by a bacterium from the genus *Streptococcus*.

39. The fusion protein of claim 38, wherein the capsular polysaccharide is CPS14, CPS8, CPS9V, or CPS15b.

40. The fusion protein of claim 37, wherein the oligo- or polysaccharide is produced by a bacterium from the genus *Klebsiella*.

41. The fusion protein of claim 40, wherein the polysaccharide is a *Klebsiella pneumoniae* capsular polysaccharide.

42. The fusion protein of claim 37, wherein the oligo- or polysaccharide comprises a glucose at its reducing end.

43. The fusion protein claim 37, wherein the fusion protein is covalently linked to an oligo- or polysaccharide and wherein the fusion protein is a conjugate vaccine.

44. A composition comprising the conjugate vaccine of claim 43 and an adjuvant.

45. A method of inducing a host immune response against a bacterial pathogen, the method comprising administering to a subject in need of the immune response an effective amount of the conjugate vaccine of claim 43.

46. A method of preventing or treating a bacterial disease and/or infection in a subject comprising administering to a subject in need thereof the conjugate vaccine of claim 43.

47. A method of producing a pneumococcal conjugate vaccine against pneumococcal infection, the method comprising:
(a) isolating the conjugate vaccine of claim 43; and
(b) combining the isolated conjugate vaccine with an adjuvant.

48. The fusion protein of claim 27, wherein the ComP glycosylation tag fragment comprises an amino acid sequence selected from the group consisting of VGVQEISASNATTNVATAT (SEQ ID NO: 39), TGVTQIASGASAATTNVASAQ (SEQ ID NO: 40), VGVQEINASSSTSNVATAT (SEQ ID NO: 41), AGVETIGASNKTKNVESAA (SEQ ID NO: 42), and VGVQTIAASNATKNVATAT (SEQ ID NO: 43).

49. The fusion protein of claim 27, wherein the ComP glycosylation tag fragment comprises the amino acid sequence VGVQEISASNATTNVATAT (SEQ ID NO: 39) Or TGVTQIASGASAATTNVASAQ (SEQ ID NO: 40).

50. The fusion protein of claim 49, wherein the ComP glycosylation tag fragment is covalently linked to an oligo- or polysaccharide at the serine residue corresponding to the conserved serine residue at position 82 of SEQ ID NO: 2 (ComP$_{110264}$: ENV58402.1).

51. The fusion protein claim 50, wherein the fusion protein is covalently linked to an oligo- or polysaccharide and wherein the fusion protein is a conjugate vaccine.

52. A composition comprising the conjugate vaccine of claim 51 and an adjuvant.

53. A method of inducing a host immune response against a bacterial pathogen, the method comprising administering to a subject in need of the immune response an effective amount of the conjugate vaccine of claim 51.

54. A method of preventing or treating a bacterial disease and/or infection in a subject comprising administering to a subject in need thereof the conjugate vaccine of claim 51.

55. A method of producing a pneumococcal conjugate vaccine against pneumococcal infection, the method comprising:
(a) isolating the conjugate vaccine of claim 51; and
(b) combining the isolated conjugate vaccine with an adjuvant.

\* \* \* \* \*

SEQUENCE LISTING

<160> NUMBER OF SEQ ID NOS: 47

<210> SEQ ID NO 1
<211> LENGTH: 147
<212> TYPE: PRT
<213> ORGANISM: Acinetobacter sp.

<400> SEQUENCE: 1

Met Asn Ala Gln Lys Gly Phe Thr Leu Ile Glu Leu Met Ile Val Ile
1               5                   10                  15

Ala Ile Ile Gly Ile Leu Ala Ala Ile Ala Ile Pro Ala Tyr Thr Asp
            20                  25                  30

Tyr Thr Val Arg Ala Arg Val Ser Glu Gly Leu Thr Ala Ala Ser Ser
        35                  40                  45

Met Lys Thr Thr Val Ser Glu Asn Ile Leu Asn Ala Gly Ala Leu Val
             50                  55                  60

Ala Gly Thr Pro Ser Thr Ala Gly Ser Ser Cys Val Gly Val Gln Glu
 65                  70                  75                  80

Ile Ser Ala Ser Asn Ala Thr Thr Asn Val Ala Thr Ala Thr Cys Gly
                 85                  90                  95

Ala Ser Ser Ala Gly Gln Ile Ile Val Thr Met Asp Thr Thr Lys Ala
                100                 105                 110

Lys Gly Ala Asn Ile Thr Leu Thr Pro Thr Tyr Ala Ser Gly Ala Val
                115                 120                 125

Thr Trp Lys Cys Thr Thr Thr Ser Asp Lys Lys Tyr Val Pro Ser Glu
    130                 135                 140

Cys Arg Gly
145

<210> SEQ ID NO 2
<211> LENGTH: 145
<212> TYPE: PRT
<213> ORGANISM: Acinetobacter soli

<400> SEQUENCE: 2

Met Asn Ala Gln Lys Gly Phe Thr Leu Ile Glu Leu Met Ile Val Ile
 1               5                  10                  15

Ala Ile Ile Gly Ile Leu Ala Ala Ile Ala Ile Pro Ala Tyr Thr Asp
                 20                  25                  30

Tyr Thr Val Arg Ser Arg Val Thr Glu Gly Leu Thr Thr Ala Ser Ala
                 35                  40                  45

Met Lys Ala Thr Val Ser Glu Asn Ile Met Asn Ala Gly Gly Thr Ser
             50                  55                  60

Met Pro Ser Ser Gly Asn Cys Thr Gly Val Thr Gln Ile Ala Ser Gly
 65                  70                  75                  80

Ala Ser Ala Ala Thr Thr Asn Val Ala Ser Ala Gln Cys Ser Asp Ser
                 85                  90                  95

Asp Gly Val Ile Thr Val Thr Met Thr Asp Lys Ala Lys Gly Val Ser
                100                 105                 110

Ile Lys Leu Thr Pro Ser Phe Ser Ser Thr Gly Ser Val Gly Trp Lys
                115                 120                 125

Cys Thr Thr Ser Ser Asp Lys Lys Tyr Val Pro Ser Glu Cys Arg Gly
    130                 135                 140

Thr
145

<210> SEQ ID NO 3
<211> LENGTH: 146
<212> TYPE: PRT
<213> ORGANISM: Acinetobacter soli

<400> SEQUENCE: 3

Met Asn Ala Gln Lys Gly Phe Thr Leu Ile Glu Leu Met Ile Val Ile
 1               5                  10                  15

Ala Ile Ile Gly Ile Leu Ala Ala Ile Ala Ile Pro Ala Tyr Thr Asp
                 20                  25                  30

Tyr Thr Val Arg Ala Arg Val Ser Glu Gly Leu Thr Thr Ala Ser Ala
                 35                  40                  45

Met Lys Ala Thr Val Ser Glu Asn Ile Leu Ser Ala Gly Gln Ile Val
             50                  55                  60

Thr Gly Thr Pro Ser Thr Ala Asn Ser Ser Cys Val Gly Val Gln Glu
65                  70                  75                  80

Ile Asn Ala Ser Ser Ser Thr Ser Asn Val Ala Thr Ala Thr Cys Ser
                85                  90                  95

Gly Leu Gly Val Ile Thr Val Thr Met Asp Ser Thr Lys Ala Lys Gly
            100                 105                 110

Val Asn Leu Thr Leu Thr Pro Thr Tyr Thr Thr Ser Asn Ala Val Thr
            115                 120                 125

Trp Lys Cys Thr Thr Thr Ser Asp Lys Lys Tyr Val Pro Ser Glu Cys
            130                 135                 140

Arg Asn
145

<210> SEQ ID NO 4
<211> LENGTH: 142
<212> TYPE: PRT
<213> ORGANISM: Acinetobacter radioresistens

<400> SEQUENCE: 4

Met Asn Thr Gln Lys Gly Phe Thr Leu Ile Glu Leu Met Ile Val Ile
1               5                   10                  15

Ala Ile Ile Gly Ile Leu Ala Ala Ile Ala Ile Pro Ala Tyr Thr Asp
            20                  25                  30

Tyr Thr Val Arg Ala Arg Val Thr Glu Ala Val Ser Thr Ala Ser Ser
            35                  40                  45

Met Lys Ala Thr Val Ser Glu Asn Ile Met Asn Ala Gly Gly Thr Gln
    50                  55                  60

Ile Pro Thr Ser Gly Asn Cys Val Gly Val Gln Thr Ile Ala Ala Ser
65                  70                  75                  80

Asn Ala Thr Lys Asn Val Ala Thr Ala Thr Cys Thr Asp Ser Thr Gly
                85                  90                  95

Val Ile Val Val Thr Thr Thr Pro Ala Ala Lys Ser Val Pro Leu Thr
            100                 105                 110

Leu Thr Pro Thr Tyr Thr Gly Gly Asn Val Lys Trp Ala Cys Ser Thr
            115                 120                 125

Thr Ala Asn Phe Lys Asn Tyr Val Pro Ser Glu Cys Arg Ser
            130                 135                 140

<210> SEQ ID NO 5
<211> LENGTH: 140
<212> TYPE: PRT
<213> ORGANISM: Acinetobacter puyangensis

<400> SEQUENCE: 5

Met Asn Ala Gln Lys Gly Phe Thr Leu Ile Glu Leu Met Ile Val Ile
1               5                   10                  15

Ala Ile Ile Gly Ile Leu Ala Ala Ile Ala Ile Pro Ala Tyr Thr Asp
            20                  25                  30

Tyr Thr Val Arg Ala Arg Val Thr Glu Ala Leu Thr Thr Ala Ser Ala
            35                  40                  45

Met Lys Ala Thr Val Ser Glu Asn Ile Met Ser Ala Gly Gly Thr Thr
    50                  55                  60

Ile Ala Ser Ser Ala Cys Asn Gly Val Ile Ser Ala Ser Ala Thr Thr
65                  70                  75                  80

Asn Val Ala Ser Ser Ala Cys Ser Gly Ser Gly Val Ile Ser Val Thr
                85                  90                  95

```
Thr Thr Ala Ala Ala Lys Gly Ile Val Leu Thr Leu Thr Pro Lys Tyr
            100                 105                 110

Thr Gly Gly Asn Val Ala Trp Gln Cys Thr Thr Thr Ser Gly Asp Ala
        115                 120                 125

Gln Lys Tyr Val Pro Ser Glu Cys Arg Thr Thr Ser
    130                 135                 140

<210> SEQ ID NO 6
<211> LENGTH: 150
<212> TYPE: PRT
<213> ORGANISM: Acinetobacter sp.

<400> SEQUENCE: 6

Met Asn Thr Gln Lys Gly Phe Thr Leu Ile Glu Leu Met Ile Val Ile
1               5                   10                  15

Ala Ile Ile Gly Ile Leu Ala Ala Ile Ala Ile Pro Ala Tyr Thr Asp
            20                  25                  30

Tyr Thr Val Arg Ala Lys Val Thr Glu Ala Ile Ser Thr Ala Ser Ala
        35                  40                  45

Met Lys Ala Thr Val Ser Glu Asn Leu Met Ser Ala Gly Gly Thr Ser
    50                  55                  60

Ile Val Ser Thr Asn Ala Asn Cys Ala Gly Val Glu Thr Ile Gly Ala
65                  70                  75                  80

Ser Asn Lys Thr Lys Asn Val Glu Ser Ala Ala Cys Thr Ala Ala Thr
                85                  90                  95

Gly Val Ile Leu Val Thr Thr Thr Ala Glu Ala Lys Ser Val Pro Leu
            100                 105                 110

Thr Leu Lys Pro Thr Tyr Thr Gly Ser Asn Val Gln Trp Lys Cys Gly
        115                 120                 125

Thr Thr Ala Ala Ala Phe Lys Tyr Val Pro Ser Glu Cys Arg Asn Asp
    130                 135                 140

Ser Ser Gly Thr Gly Phe
145                 150

<210> SEQ ID NO 7
<211> LENGTH: 119
<212> TYPE: PRT
<213> ORGANISM: Acinetobacter sp.

<400> SEQUENCE: 7

Ala Tyr Thr Asp Tyr Thr Val Arg Ala Arg Val Ser Glu Gly Leu Thr
1               5                   10                  15

Ala Ala Ser Ser Met Lys Thr Thr Val Ser Glu Asn Ile Leu Asn Ala
            20                  25                  30

Gly Ala Leu Val Ala Gly Thr Pro Ser Thr Ala Gly Ser Ser Cys Val
        35                  40                  45

Gly Val Gln Glu Ile Ser Ala Ser Asn Ala Thr Asn Val Ala Thr
    50                  55                  60

Ala Thr Cys Gly Ala Ser Ser Ala Gly Gln Ile Ile Val Thr Met Asp
65                  70                  75                  80

Thr Thr Lys Ala Lys Gly Ala Asn Ile Thr Leu Thr Pro Thr Tyr Ala
                85                  90                  95

Ser Gly Ala Val Thr Trp Lys Cys Thr Thr Thr Ser Asp Lys Lys Tyr
            100                 105                 110

Val Pro Ser Glu Cys Arg Gly
        115
```

```
<210> SEQ ID NO 8
<211> LENGTH: 117
<212> TYPE: PRT
<213> ORGANISM: Acinetobacter soli

<400> SEQUENCE: 8

Ala Tyr Thr Asp Tyr Thr Val Arg Ser Arg Val Thr Glu Gly Leu Thr
1               5                   10                  15

Thr Ala Ser Ala Met Lys Ala Thr Val Ser Glu Asn Ile Met Asn Ala
            20                  25                  30

Gly Gly Thr Ser Met Pro Ser Ser Gly Asn Cys Thr Gly Val Thr Gln
        35                  40                  45

Ile Ala Ser Gly Ala Ser Ala Ala Thr Thr Asn Val Ala Ser Ala Gln
    50                  55                  60

Cys Ser Asp Ser Asp Gly Val Ile Thr Val Thr Met Thr Asp Lys Ala
65                  70                  75                  80

Lys Gly Val Ser Ile Lys Leu Thr Pro Ser Phe Ser Ser Thr Gly Ser
                85                  90                  95

Val Gly Trp Lys Cys Thr Thr Ser Ser Asp Lys Lys Tyr Val Pro Ser
            100                 105                 110

Glu Cys Arg Gly Thr
        115

<210> SEQ ID NO 9
<211> LENGTH: 118
<212> TYPE: PRT
<213> ORGANISM: Acinetobacter soli

<400> SEQUENCE: 9

Ala Tyr Thr Asp Tyr Thr Val Arg Ala Arg Val Ser Glu Gly Leu Thr
1               5                   10                  15

Thr Ala Ser Ala Met Lys Ala Thr Val Ser Glu Asn Ile Leu Ser Ala
            20                  25                  30

Gly Gln Ile Val Thr Gly Thr Pro Ser Thr Ala Asn Ser Ser Cys Val
        35                  40                  45

Gly Val Gln Glu Ile Asn Ala Ser Ser Thr Ser Asn Val Ala Thr
    50                  55                  60

Ala Thr Cys Ser Gly Leu Gly Val Ile Thr Val Thr Met Asp Ser Thr
65                  70                  75                  80

Lys Ala Lys Gly Val Asn Leu Thr Leu Thr Pro Thr Tyr Thr Thr Ser
                85                  90                  95

Asn Ala Val Thr Trp Lys Cys Thr Thr Thr Ser Asp Lys Lys Tyr Val
            100                 105                 110

Pro Ser Glu Cys Arg Asn
        115

<210> SEQ ID NO 10
<211> LENGTH: 114
<212> TYPE: PRT
<213> ORGANISM: Acinetobacter radioresistens

<400> SEQUENCE: 10

Ala Tyr Thr Asp Tyr Thr Val Arg Ala Arg Val Thr Glu Ala Val Ser
1               5                   10                  15

Thr Ala Ser Ser Met Lys Ala Thr Val Ser Glu Asn Ile Met Asn Ala
            20                  25                  30
```

-continued

```
Gly Gly Thr Gln Ile Pro Thr Ser Gly Asn Cys Val Gly Val Gln Thr
            35                  40                  45

Ile Ala Ala Ser Asn Ala Thr Lys Asn Val Ala Thr Ala Thr Cys Thr
 50                  55                  60

Asp Ser Thr Gly Val Ile Val Val Thr Thr Pro Ala Ala Lys Ser
65                  70                  75                  80

Val Pro Leu Thr Leu Thr Pro Thr Tyr Thr Gly Gly Asn Val Lys Trp
                85                  90                  95

Ala Cys Ser Thr Thr Ala Asn Phe Lys Asn Tyr Val Pro Ser Glu Cys
                100                 105                 110

Arg Ser

<210> SEQ ID NO 11
<211> LENGTH: 112
<212> TYPE: PRT
<213> ORGANISM: Acinetobacter puyangensis

<400> SEQUENCE: 11

Ala Tyr Thr Asp Tyr Thr Val Arg Ala Arg Val Thr Glu Ala Leu Thr
 1               5                   10                  15

Thr Ala Ser Ala Met Lys Ala Thr Val Ser Glu Asn Ile Met Ser Ala
                20                  25                  30

Gly Gly Thr Thr Ile Ala Ser Ser Ala Cys Asn Gly Val Ile Ser Ala
            35                  40                  45

Ser Ala Thr Thr Asn Val Ala Ser Ser Ala Cys Ser Gly Ser Gly Val
 50                  55                  60

Ile Ser Val Thr Thr Thr Ala Ala Ala Lys Gly Ile Val Leu Thr Leu
65                  70                  75                  80

Thr Pro Lys Tyr Thr Gly Gly Asn Val Ala Trp Gln Cys Thr Thr Thr
                85                  90                  95

Ser Gly Asp Ala Gln Lys Tyr Val Pro Ser Glu Cys Arg Thr Thr Ser
                100                 105                 110

<210> SEQ ID NO 12
<211> LENGTH: 122
<212> TYPE: PRT
<213> ORGANISM: Acinetobacter sp.

<400> SEQUENCE: 12

Ala Tyr Thr Asp Tyr Thr Val Arg Ala Lys Val Thr Glu Ala Ile Ser
 1               5                   10                  15

Thr Ala Ser Ala Met Lys Ala Thr Val Ser Glu Asn Leu Met Ser Ala
                20                  25                  30

Gly Gly Thr Ser Ile Val Ser Thr Asn Ala Asn Cys Ala Gly Val Glu
            35                  40                  45

Thr Ile Gly Ala Ser Asn Lys Thr Lys Asn Val Glu Ser Ala Ala Cys
 50                  55                  60

Thr Ala Ala Thr Gly Val Ile Leu Val Thr Thr Thr Ala Glu Ala Lys
65                  70                  75                  80

Ser Val Pro Leu Thr Leu Lys Pro Thr Tyr Thr Gly Ser Asn Val Gln
                85                  90                  95

Trp Lys Cys Gly Thr Thr Ala Ala Phe Lys Tyr Val Pro Ser Glu
                100                 105                 110

Cys Arg Asn Asp Ser Ser Gly Thr Gly Phe
                115                 120
```

```
<210> SEQ ID NO 13
<211> LENGTH: 21
<212> TYPE: PRT
<213> ORGANISM: Unknown
<220> FEATURE:
<223> OTHER INFORMATION: Description of Unknown:
      ComP sequence

<400> SEQUENCE: 13

Cys Val Gly Val Gln Glu Ile Ser Ala Ser Asn Ala Thr Thr Asn Val
1               5                   10                  15

Ala Thr Ala Thr Cys
            20

<210> SEQ ID NO 14
<211> LENGTH: 23
<212> TYPE: PRT
<213> ORGANISM: Unknown
<220> FEATURE:
<223> OTHER INFORMATION: Description of Unknown:
      ComP sequence

<400> SEQUENCE: 14

Cys Thr Gly Val Thr Gln Ile Ala Ser Gly Ala Ser Ala Ala Thr Thr
1               5                   10                  15

Asn Val Ala Ser Ala Gln Cys
            20

<210> SEQ ID NO 15
<211> LENGTH: 21
<212> TYPE: PRT
<213> ORGANISM: Unknown
<220> FEATURE:
<223> OTHER INFORMATION: Description of Unknown:
      ComP sequence

<400> SEQUENCE: 15

Cys Val Gly Val Gln Glu Ile Asn Ala Ser Ser Ser Thr Ser Asn Val
1               5                   10                  15

Ala Thr Ala Thr Cys
            20

<210> SEQ ID NO 16
<211> LENGTH: 21
<212> TYPE: PRT
<213> ORGANISM: Unknown
<220> FEATURE:
<223> OTHER INFORMATION: Description of Unknown:
      ComP sequence

<400> SEQUENCE: 16

Cys Ala Gly Val Glu Thr Ile Gly Ala Ser Asn Lys Thr Lys Asn Val
1               5                   10                  15

Glu Ser Ala Ala Cys
            20

<210> SEQ ID NO 17
<211> LENGTH: 21
<212> TYPE: PRT
<213> ORGANISM: Unknown
<220> FEATURE:
<223> OTHER INFORMATION: Description of Unknown:
      ComP sequence

<400> SEQUENCE: 17

Cys Val Gly Val Gln Thr Ile Ala Ala Ser Asn Ala Thr Lys Asn Val
```

```
                1               5              10              15
Ala Thr Ala Thr Cys
                20

<210> SEQ ID NO 18
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Lys Lys Ile Trp Leu Ala Leu Ala Gly Leu Val Leu Ala Phe Ser
1               5                   10                  15

Ala Ser Ala Ala Gln Tyr Glu Asp Gly Lys Gln Tyr Thr Thr Leu Glu
                20                  25                  30

Lys Pro Val Ala Gly Ala Pro Gln Val Leu Glu Phe Phe Ser Phe Phe
                35                  40                  45

Cys Pro His Cys Tyr Gln Phe Glu Glu Val Leu His Ile Ser Asp Asn
            50                  55                  60

Val Lys Lys Leu Pro Glu Gly Val Lys Met Thr Lys Tyr His Val
65                  70                  75                  80

Asn Phe Met Gly Gly Asp Leu Gly Lys Asp Leu Thr Gln Ala Trp Ala
                85                  90                  95

Val Ala Met Ala Leu Gly Val Glu Asp Lys Val Thr Val Pro Leu Phe
                100                 105                 110

Glu Gly Val Gln Lys Thr Gln Thr Ile Arg Ser Ala Ser Asp Ile Arg
                115                 120                 125

Asp Val Phe Ile Asn Ala Gly Ile Lys Gly Glu Glu Tyr Asp Ala Ala
            130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
                165                 170                 175

Lys Tyr Gln Leu Asn Pro Gln Gly Met Asp Thr Ser Asn Met Asp Val
                180                 185                 190

Phe Val Gln Gln Tyr Ala Asp Thr Val Lys Tyr Leu Ser Glu Lys Lys
                195                 200                 205

Gly Gly Gly Ser Ala Tyr Thr Asp Tyr Thr Val Arg Ser Arg Val Thr
            210                 215                 220

Glu Gly Leu Thr Thr Ala Ser Ala Met Lys Ala Thr Val Ser Glu Asn
225                 230                 235                 240

Ile Met Asn Ala Gly Gly Thr Ser Met Pro Ser Ser Gly Asn Cys Thr
                245                 250                 255

Gly Val Thr Gln Ile Ala Ser Gly Ala Ser Ala Thr Thr Asn Val
                260                 265                 270

Ala Ser Ala Gln Cys Ser Asp Ser Asp Gly Val Ile Thr Val Thr Met
            275                 280                 285

Thr Asp Lys Ala Lys Gly Val Ser Ile Lys Leu Thr Pro Ser Phe Ser
            290                 295                 300

Ser Thr Gly Ser Val Gly Trp Lys Cys Thr Thr Ser Ser Asp Lys Lys
305                 310                 315                 320

Tyr Val Pro Ser Glu Cys Arg Gly Thr His His His His His
                325                 330                 335
```

<210> SEQ ID NO 19
<211> LENGTH: 519
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
            355                 360                 365
```

```
Val Arg Thr Ala Val Ile Asn Ala Ala Ser Gly Arg Gln Thr Val Asp
    370                 375                 380

Glu Ala Leu Lys Asp Ala Gln Thr Asn Ala Ala Ala Tyr Thr Asp
385                 390                 395                 400

Tyr Thr Val Arg Ser Arg Val Thr Glu Gly Leu Thr Thr Ala Ser Ala
                405                 410                 415

Met Lys Ala Thr Val Ser Glu Asn Ile Met Asn Ala Gly Gly Thr Ser
                420                 425                 430

Met Pro Ser Ser Gly Asn Cys Thr Gly Val Thr Gln Ile Ala Ser Gly
            435                 440                 445

Ala Ser Ala Ala Thr Thr Asn Val Ala Ser Ala Gln Cys Ser Asp Ser
    450                 455                 460

Asp Gly Val Ile Thr Val Thr Met Thr Asp Lys Ala Lys Gly Val Ser
465                 470                 475                 480

Ile Lys Leu Thr Pro Ser Phe Ser Ser Thr Gly Ser Val Gly Trp Lys
                485                 490                 495

Cys Thr Thr Ser Ser Asp Lys Lys Tyr Val Pro Ser Glu Cys Arg Gly
                500                 505                 510

Thr His His His His His His
            515

<210> SEQ ID NO 20
<211> LENGTH: 758
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Lys Ile Trp Leu Ala Leu Ala Gly Leu Val Leu Ala Phe Ser
1               5                   10                  15

Ala Ser Ala Ala Glu Glu Ala Phe Asp Leu Trp Asn Glu Cys Ala Lys
                20                  25                  30

Ala Cys Val Leu Asp Leu Lys Asp Gly Val Arg Ser Ser Arg Met Ser
            35                  40                  45

Val Asp Pro Ala Ile Ala Asp Thr Asn Gly Gln Gly Val Leu His Tyr
    50                  55                  60

Ser Met Val Leu Glu Gly Gly Asn Asp Ala Leu Lys Leu Ala Ile Asp
65                  70                  75                  80

Asn Ala Leu Ser Ile Thr Ser Asp Gly Leu Thr Ile Arg Leu Glu Gly
                85                  90                  95

Gly Val Glu Pro Asn Lys Pro Val Arg Tyr Ser Tyr Thr Arg Gln Ala
            100                 105                 110

Arg Gly Ser Trp Ser Leu Asn Trp Leu Val Pro Ile Gly His Glu Lys
        115                 120                 125

Pro Ser Asn Ile Lys Val Phe Ile His Glu Leu Asn Ala Gly Asn Gln
    130                 135                 140

Leu Ser His Met Ser Pro Ile Tyr Thr Ile Glu Met Gly Asp Glu Leu
145                 150                 155                 160

Leu Ala Lys Leu Ala Arg Asp Ala Thr Phe Phe Val Arg Ala His Glu
                165                 170                 175

Ser Asn Glu Met Gln Pro Thr Leu Ala Ile Ser His Ala Gly Val Ser
            180                 185                 190

Val Val Met Ala Gln Ala Gln Pro Arg Arg Glu Lys Arg Trp Ser Glu
```

```
            195                 200                 205
Trp Ala Ser Gly Lys Val Leu Cys Leu Leu Asp Pro Leu Asp Gly Val
210                 215                 220
Tyr Asn Tyr Leu Ala Gln Gln Arg Cys Asn Leu Asp Asp Thr Trp Glu
225                 230                 235                 240
Gly Lys Ile Tyr Arg Val Leu Ala Gly Asn Pro Ala Lys His Asp Leu
                    245                 250                 255
Asp Ile Lys Pro Thr Val Ile Ser His Arg Leu His Phe Pro Glu Gly
                260                 265                 270
Gly Ser Leu Ala Ala Leu Thr Ala His Gln Ala Cys His Leu Pro Leu
            275                 280                 285
Glu Thr Phe Thr Arg His Arg Gln Pro Arg Gly Trp Glu Gln Leu Glu
290                 295                 300
Gln Cys Gly Tyr Pro Val Gln Arg Leu Val Ala Leu Tyr Leu Ala Ala
305                 310                 315                 320
Arg Leu Ser Trp Asn Gln Val Asp Gln Val Ile Arg Asn Ala Leu Ala
                    325                 330                 335
Ser Pro Gly Ser Gly Gly Asp Leu Gly Glu Ala Ile Arg Glu Gln Pro
                340                 345                 350
Glu Gln Ala Arg Leu Ala Leu Thr Leu Ala Ala Ala Glu Ser Glu Arg
            355                 360                 365
Phe Val Arg Gln Gly Thr Gly Asn Asp Glu Ala Gly Ala Ala Ser Ala
370                 375                 380
Asp Val Val Ser Leu Thr Cys Pro Val Ala Gly Glu Cys Ala Gly
385                 390                 395                 400
Pro Ala Asp Ser Gly Asp Ala Leu Leu Glu Arg Asn Tyr Pro Thr Gly
                    405                 410                 415
Ala Glu Phe Leu Gly Asp Gly Asp Ile Ser Phe Ser Thr Arg Gly
                420                 425                 430
Thr Gln Asn Trp Thr Val Glu Arg Leu Leu Gln Ala His Arg Gln Leu
            435                 440                 445
Glu Glu Arg Gly Tyr Val Phe Val Gly Tyr His Gly Thr Phe Leu Glu
450                 455                 460
Ala Ala Gln Ser Ile Val Phe Gly Gly Val Arg Ala Arg Ser Gln Asp
465                 470                 475                 480
Leu Asp Ala Ile Trp Arg Gly Phe Tyr Ile Ala Gly Asp Pro Ala Leu
                    485                 490                 495
Ala Tyr Gly Tyr Ala Gln Asp Gln Glu Pro Asp Ala Arg Gly Arg Ile
                500                 505                 510
Arg Asn Gly Ala Leu Leu Arg Val Tyr Val Pro Arg Ser Ser Leu Pro
            515                 520                 525
Gly Phe Tyr Arg Thr Gly Leu Thr Leu Ala Ala Pro Glu Ala Ala Gly
530                 535                 540
Glu Val Glu Arg Leu Ile Gly His Pro Leu Pro Leu Arg Leu Asp Ala
545                 550                 555                 560
Ile Thr Gly Pro Glu Glu Gly Gly Arg Leu Thr Ile Leu Gly Trp
                    565                 570                 575
Pro Leu Ala Glu Arg Thr Val Val Ile Pro Ser Ala Ile Pro Thr Asp
                580                 585                 590
Pro Arg Asn Val Gly Gly Asp Leu Asp Pro Ser Ser Ile Pro Asp Lys
            595                 600                 605
Glu Gln Ala Ile Ser Ala Leu Pro Asp Tyr Ala Ser Gln Pro Gly Lys
610                 615                 620
```

```
Pro Pro Arg Glu Asp Leu Lys Gly Gly Gly Ser Ala Tyr Thr Asp Tyr
625                 630                 635                 640

Thr Val Arg Ser Arg Val Thr Glu Gly Leu Thr Thr Ala Ser Ala Met
            645                 650                 655

Lys Ala Thr Val Ser Glu Asn Ile Met Asn Ala Gly Thr Ser Met
        660                 665                 670

Pro Ser Ser Gly Asn Cys Thr Gly Val Thr Gln Ile Ala Ser Gly Ala
            675                 680                 685

Ser Ala Ala Thr Thr Asn Val Ala Ser Ala Gln Cys Ser Asp Ser Asp
690                 695                 700

Gly Val Ile Thr Val Thr Met Thr Asp Lys Ala Lys Gly Val Ser Ile
705                 710                 715                 720

Lys Leu Thr Pro Ser Phe Ser Ser Thr Gly Ser Val Gly Trp Lys Cys
            725                 730                 735

Thr Thr Ser Ser Asp Lys Lys Tyr Val Pro Ser Glu Cys Arg Gly Thr
            740                 745                 750

His His His His His
        755

<210> SEQ ID NO 21
<211> LENGTH: 5
<212> TYPE: PRT
<213> ORGANISM: Unknown
<220> FEATURE:
<223> OTHER INFORMATION: Description of Unknown:
      N-glycosylation bacterial sequence
<220> FEATURE:
<221> NAME/KEY: MOD_RES
<222> LOCATION: (2)..(2)
<223> OTHER INFORMATION: Any amino acid except Pro

<400> SEQUENCE: 21

Asp Xaa Asn Ser Thr
1               5

<210> SEQ ID NO 22
<211> LENGTH: 14
<212> TYPE: PRT
<213> ORGANISM: Unknown
<220> FEATURE:
<223> OTHER INFORMATION: Description of Unknown:
      Glycopeptide

<400> SEQUENCE: 22

Ile Ser Ala Ser Asn Ala Thr Thr Asn Val Ala Thr Ala Thr
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Ser
1

<210> SEQ ID NO 24
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 24

Ala Ala Ala
1

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
actggtcgac tagtagtact atatggcttt aaa                                33

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
actgctgcag ttaatattct attgaacaaa attttaac                           38

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gagaatggtt tacatactca gcgaatttgt tcttagattt aatg                    44

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cattaaatct aagaacaaat tcgctgagta tgtaaaccat tctc                    44

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggagtccaag aaattgcggc aagtaatgcc a                                  31

<210> SEQ ID NO 30
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 30
gtggcattac ttgccgcaat ttcttggact cc                                    32

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caagaaattt cagcagcgaa tgccactacg aac                                   33

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gttcgtagtg gcattcgctg ctgaaatttc ttg                                   33

<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acagatcgcg tccggcgccg cagcagcgac aacaaatgta gcgt                       44

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acgctacatt tgttgtcgct gctgcggcgc cggacgcgat ctgt                       44

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgggcgtcac acagatcgcg gccggcgcct cagcagcgac aaca                       44

<210> SEQ ID NO 36
<211> LENGTH: 44
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 36
tgttgtcgct gctgaggcgc cggccgcgat ctgtgtgacg cccg            44

<210> SEQ ID NO 37
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: V, A or not present
<220> FEATURE:
<221> NAME/KEY: MOD_RES
<222> LOCATION: (2)..(2)
<223> OTHER INFORMATION: A, G, T or not present
<220> FEATURE:
<221> NAME/KEY: MOD_RES
<222> LOCATION: (5)..(5)
<223> OTHER INFORMATION: P, S or Q
<220> FEATURE:
<221> NAME/KEY: MOD_RES
<222> LOCATION: (6)..(6)
<223> OTHER INFORMATION: S, M or I
<220> FEATURE:
<221> NAME/KEY: MOD_RES
<222> LOCATION: (7)..(7)
<223> OTHER INFORMATION: T, P or V
<220> FEATURE:
<221> NAME/KEY: MOD_RES
<222> LOCATION: (8)..(8)
<223> OTHER INFORMATION: A, S or T
<220> FEATURE:
<221> NAME/KEY: MOD_RES
<222> LOCATION: (9)..(9)
<223> OTHER INFORMATION: G, N, S or T
<220> FEATURE:
<221> NAME/KEY: MOD_RES
<222> LOCATION: (10)..(10)
<223> OTHER INFORMATION: N or not present
<220> FEATURE:
<221> NAME/KEY: MOD_RES
<222> LOCATION: (11)..(11)
<223> OTHER INFORMATION: S, G or A
<220> FEATURE:
<221> NAME/KEY: MOD_RES
<222> LOCATION: (12)..(12)
<223> OTHER INFORMATION: S or N
<220> FEATURE:
<221> NAME/KEY: MOD_RES
<222> LOCATION: (14)..(14)
<223> OTHER INFORMATION: V, T or A
<220> FEATURE:
<221> NAME/KEY: MOD_RES
<222> LOCATION: (17)..(17)
<223> OTHER INFORMATION: Q, T or E
<220> FEATURE:
<221> NAME/KEY: MOD_RES
<222> LOCATION: (18)..(18)
<223> OTHER INFORMATION: E, Q or T
<220> FEATURE:
<221> NAME/KEY: MOD_RES
<222> LOCATION: (20)..(20)
<223> OTHER INFORMATION: S, N, A or G
<220> FEATURE:
<221> NAME/KEY: MOD_RES
<222> LOCATION: (21)..(21)
<223> OTHER INFORMATION: S or not present
<220> FEATURE:
<221> NAME/KEY: MOD_RES
<222> LOCATION: (22)..(22)
<223> OTHER INFORMATION: G or not present

```
<220> FEATURE:
<221> NAME/KEY: MOD_RES
<222> LOCATION: (25)..(25)
<223> OTHER INFORMATION: N, S or A
<220> FEATURE:
<221> NAME/KEY: MOD_RES
<222> LOCATION: (26)..(26)
<223> OTHER INFORMATION: A, S or K
<220> FEATURE:
<221> NAME/KEY: MOD_RES
<222> LOCATION: (28)..(28)
<223> OTHER INFORMATION: T, S or K
<220> FEATURE:
<221> NAME/KEY: MOD_RES
<222> LOCATION: (31)..(31)
<223> OTHER INFORMATION: A or E
<220> FEATURE:
<221> NAME/KEY: MOD_RES
<222> LOCATION: (32)..(32)
<223> OTHER INFORMATION: T or S
<220> FEATURE:
<221> NAME/KEY: MOD_RES
<222> LOCATION: (34)..(34)
<223> OTHER INFORMATION: T, Q or A
<220> FEATURE:
<221> NAME/KEY: MOD_RES
<222> LOCATION: (36)..(36)
<223> OTHER INFORMATION: G, S or T
<220> FEATURE:
<221> NAME/KEY: MOD_RES
<222> LOCATION: (37)..(37)
<223> OTHER INFORMATION: A, G or D
<220> FEATURE:
<221> NAME/KEY: MOD_RES
<222> LOCATION: (38)..(38)
<223> OTHER INFORMATION: S, L or A
<220> FEATURE:
<221> NAME/KEY: MOD_RES
<222> LOCATION: (39)..(39)
<223> OTHER INFORMATION: S, G, D or T
<220> FEATURE:
<221> NAME/KEY: MOD_RES
<222> LOCATION: (40)..(40)
<223> OTHER INFORMATION: A, V or G
<220> FEATURE:
<221> NAME/KEY: MOD_RES
<222> LOCATION: (41)..(41)
<223> OTHER INFORMATION: G, I or V
<220> FEATURE:
<221> NAME/KEY: MOD_RES
<222> LOCATION: (42)..(42)
<223> OTHER INFORMATION: Q, T or I
<220> FEATURE:
<221> NAME/KEY: MOD_RES
<222> LOCATION: (43)..(43)
<223> OTHER INFORMATION: I, V, T or L
<220> FEATURE:
<221> NAME/KEY: MOD_RES
<222> LOCATION: (44)..(44)
<223> OTHER INFORMATION: I, T or V
<220> FEATURE:
<221> NAME/KEY: MOD_RES
<222> LOCATION: (45)..(45)
<223> OTHER INFORMATION: M or not present
<220> FEATURE:
<221> NAME/KEY: MOD_RES
<222> LOCATION: (46)..(46)
<223> OTHER INFORMATION: D or not present

<400> SEQUENCE: 37

Xaa Xaa Gly Thr Xaa Xaa Xaa Xaa Xaa Xaa Xaa Xaa Cys Xaa Gly Val
1               5                   10                  15

Xaa Xaa Ile Xaa Xaa Xaa Ala Ser Xaa Xaa Thr Xaa Asn Val Xaa Xaa
            20                  25                  30

Ala Xaa Cys Xaa Xaa Xaa Xaa Xaa Xaa Xaa Xaa Xaa Xaa
        35                  40                  45
```

```
<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V, T or A
<220> FEATURE:
<221> NAME/KEY: MOD_RES
<222> LOCATION: (4)..(4)
<223> OTHER INFORMATION: Q, T or E
<220> FEATURE:
<221> NAME/KEY: MOD_RES
<222> LOCATION: (5)..(5)
<223> OTHER INFORMATION: E, Q or T
<220> FEATURE:
<221> NAME/KEY: MOD_RES
<222> LOCATION: (7)..(7)
<223> OTHER INFORMATION: S, N, A or G
<220> FEATURE:
<221> NAME/KEY: MOD_RES
<222> LOCATION: (8)..(8)
<223> OTHER INFORMATION: S or not present
<220> FEATURE:
<221> NAME/KEY: MOD_RES
<222> LOCATION: (9)..(9)
<223> OTHER INFORMATION: G or not present
<220> FEATURE:
<221> NAME/KEY: MOD_RES
<222> LOCATION: (12)..(12)
<223> OTHER INFORMATION: N, S or A
<220> FEATURE:
<221> NAME/KEY: MOD_RES
<222> LOCATION: (13)..(13)
<223> OTHER INFORMATION: A, S or K
<220> FEATURE:
<221> NAME/KEY: MOD_RES
<222> LOCATION: (15)..(15)
<223> OTHER INFORMATION: T, S or K
<220> FEATURE:
<221> NAME/KEY: MOD_RES
<222> LOCATION: (18)..(18)
<223> OTHER INFORMATION: A or E
<220> FEATURE:
<221> NAME/KEY: MOD_RES
<222> LOCATION: (19)..(19)
<223> OTHER INFORMATION: T or S
<220> FEATURE:
<221> NAME/KEY: MOD_RES
<222> LOCATION: (21)..(21)
<223> OTHER INFORMATION: T, Q or A
<220> FEATURE:
<223> OTHER INFORMATION: See specification as filed for detailed
      description of substitutions and preferred embodiments

<400> SEQUENCE: 38

Xaa Gly Val Xaa Xaa Ile Xaa Xaa Xaa Ala Ser Xaa Xaa Thr Xaa Asn
1               5                   10                  15

Val Xaa Xaa Ala Xaa
            20

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39
```

Val Gly Val Gln Glu Ile Ser Ala Ser Asn Ala Thr Thr Asn Val Ala
1               5                   10                  15

Thr Ala Thr

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Gly Val Thr Gln Ile Ala Ser Gly Ala Ser Ala Ala Thr Thr Asn
1               5                   10                  15

Val Ala Ser Ala Gln
            20

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Gly Val Gln Glu Ile Asn Ala Ser Ser Ser Thr Ser Asn Val Ala
1               5                   10                  15

Thr Ala Thr

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Gly Val Glu Thr Ile Gly Ala Ser Asn Lys Thr Lys Asn Val Glu
1               5                   10                  15

Ser Ala Ala

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Gly Val Gln Thr Ile Ala Ala Ser Asn Ala Thr Lys Asn Val Ala
1               5                   10                  15

Thr Ala Thr

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asn Gly Val Ile Ser Ala Ser Ala Thr Thr Asn Val Ala Ser Ser Ala
1               5                   10                  15

<210> SEQ ID NO 45
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: V, T or A
<220> FEATURE:
<221> NAME/KEY: MOD_RES
<222> LOCATION: (5)..(5)
<223> OTHER INFORMATION: Q, T or E
<220> FEATURE:
<221> NAME/KEY: MOD_RES
<222> LOCATION: (6)..(6)
<223> OTHER INFORMATION: E, Q or T
<220> FEATURE:
<221> NAME/KEY: MOD_RES
<222> LOCATION: (8)..(8)
<223> OTHER INFORMATION: S, N, A or G
<220> FEATURE:
<221> NAME/KEY: MOD_RES
<222> LOCATION: (9)..(9)
<223> OTHER INFORMATION: S or not present
<220> FEATURE:
<221> NAME/KEY: MOD_RES
<222> LOCATION: (10)..(10)
<223> OTHER INFORMATION: G or not present
<220> FEATURE:
<221> NAME/KEY: MOD_RES
<222> LOCATION: (13)..(13)
<223> OTHER INFORMATION: N, S or A
<220> FEATURE:
<221> NAME/KEY: MOD_RES
<222> LOCATION: (14)..(14)
<223> OTHER INFORMATION: A, S or K
<220> FEATURE:
<221> NAME/KEY: MOD_RES
<222> LOCATION: (16)..(16)
<223> OTHER INFORMATION: T, S or K
<220> FEATURE:
<221> NAME/KEY: MOD_RES
<222> LOCATION: (19)..(19)
<223> OTHER INFORMATION: A or E
<220> FEATURE:
<221> NAME/KEY: MOD_RES
<222> LOCATION: (20)..(20)
<223> OTHER INFORMATION: T or S
<220> FEATURE:
<221> NAME/KEY: MOD_RES
<222> LOCATION: (22)..(22)
<223> OTHER INFORMATION: T, Q or A
<220> FEATURE:
<223> OTHER INFORMATION: See specification as filed for detailed
      description of substitutions and preferred embodiments

<400> SEQUENCE: 45

Cys Xaa Gly Val Xaa Xaa Ile Xaa Xaa Xaa Ala Ser Xaa Xaa Thr Xaa
1               5                   10                  15

Asn Val Xaa Xaa Ala Xaa Cys
            20

<210> SEQ ID NO 46
<211> LENGTH: 6
<212> TYPE: PRT
<213> ORGANISM: Artificial Sequence -continued

```
<220> FEATURE:
<223> OTHER INFORMATION: Description of Artificial Sequence: Synthetic
      6xHis tag

<400> SEQUENCE: 46

His His His His His His
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      10x His tag

<400> SEQUENCE: 47

His His His His His His His His His His
1               5                   10
```